(12) United States Patent
Musselman

(10) Patent No.: US 10,825,673 B2
(45) Date of Patent: Nov. 3, 2020

(54) APPARATUS AND METHOD FOR REDUCING MATRIX EFFECTS

(71) Applicant: IonSense Inc., Saugus, MA (US)

(72) Inventor: Brian D Musselman, Melrose, MA (US)

(73) Assignee: IonSense Inc., Saugus, MA (US)

( * ) Notice: Subject to any disclaimer, the term of this patent is extended or adjusted under 35 U.S.C. 154(b) by 0 days.

(21) Appl. No.: 16/422,339

(22) Filed: May 24, 2019

(65) Prior Publication Data

US 2019/0371592 A1    Dec. 5, 2019

Related U.S. Application Data

(60) Provisional application No. 62/679,668, filed on Jun. 1, 2018.

(51) Int. Cl.
*H01J 49/14* (2006.01)

(52) U.S. Cl.
CPC .................. *H01J 49/145* (2013.01)

(58) Field of Classification Search
CPC .................................................. H01J 49/145
See application file for complete search history.

(56) References Cited

U.S. PATENT DOCUMENTS

| | | |
|---|---|---|
| 3,633,027 A | 1/1972 | Rhyage |
| 3,957,470 A | 5/1976 | Dawes |
| 4,016,421 A | 4/1977 | Hull |

(Continued)

FOREIGN PATENT DOCUMENTS

| | | |
|---|---|---|
| DE | 102007015542 | 10/2007 |
| EP | 1434050 | 6/2004 |

(Continued)

OTHER PUBLICATIONS

The AccuTOF-DART Mass Spectrometer, Jan. 1, 2006, pp. 1-6; www.jeolusa.com/SERVICESUPPORT/ApplicationsResources/AnalyticalInstruments/Documents/Downloads/tabid/337/DMXModule/693/CommandCore_Download/Default.aspx?EntryId=171.

(Continued)

*Primary Examiner* — Nicole M Ippolito
*Assistant Examiner* — Hanway Chang
(74) *Attorney, Agent, or Firm* — Sci-Law Strategies, PC

(57) ABSTRACT

In an embodiment of the present ambient ionization experiment, the abundance of background chemicals relative to ions of interest is decreased by reducing the overall abundance of background chemicals introduced into the ionizing region. In an embodiment of the present invention, the reduction of unwanted background chemicals in the ionization region can be effected by limiting the area which the sample volume is deposited. In an embodiment of the present invention, the reduction of unwanted background chemicals in the ionization region can be effected by decreasing the duration of time that the sample is exposed to the atmospheric pressure ionization source. In an embodiment of the present invention, the reduction of unwanted background chemicals in the ionization region can be effected by limiting the sample volume. In an embodiment of the present invention dilution of the sample with water can be used to reduce the contribution of the background chemicals. In an embodiment of the present ambient ionization experiment, an ion intensifier is used to suppress ionization of background chemicals to permit more efficient ionization and detection of the molecules of interest.

20 Claims, 33 Drawing Sheets

(56) References Cited

U.S. PATENT DOCUMENTS

| | | |
|---|---|---|
| 4,144,451 A | 3/1979 | Kambara |
| 4,213,326 A | 7/1980 | Brodasky |
| 4,542,293 A | 9/1985 | Fenn |
| 4,546,253 A | 10/1985 | Tsuchiya |
| 4,654,052 A | 3/1987 | Sharp |
| 4,662,914 A | 5/1987 | Hansen |
| 4,861,988 A | 8/1989 | Henion |
| 4,941,618 A | 7/1990 | Hildebrand |
| 5,012,052 A | 4/1991 | Hayes |
| 5,055,677 A | 10/1991 | Amirav |
| 5,137,553 A | 8/1992 | Dawes |
| 5,192,865 A | 3/1993 | Zhu |
| 5,306,412 A | 4/1994 | Whitehouse |
| 5,352,892 A | 10/1994 | Mordehai |
| 5,367,163 A | 11/1994 | Otsuka |
| 5,381,008 A | 1/1995 | Tanner |
| 5,412,208 A | 5/1995 | Covey |
| 5,448,062 A | 9/1995 | Cooks |
| 5,552,599 A | 9/1996 | Giessmann |
| 5,559,326 A | 9/1996 | Goodley |
| 5,614,711 A | 3/1997 | Li |
| 5,624,537 A | 4/1997 | Turner |
| 5,684,300 A | 11/1997 | Taylor |
| 5,716,825 A | 2/1998 | Hancock |
| 5,736,741 A | 4/1998 | Bertsch |
| 5,788,166 A | 8/1998 | Valaskovic |
| 5,859,433 A | 1/1999 | Franzen |
| 5,868,322 A | 2/1999 | Loucks, Jr. |
| 5,877,495 A | 3/1999 | Takada |
| 5,889,404 A | 3/1999 | Abdel-Rahman |
| 5,959,297 A | 9/1999 | Weinberg |
| 5,997,746 A | 12/1999 | Valaskovic |
| 6,085,601 A | 7/2000 | Linker |
| 6,107,628 A | 8/2000 | Smith |
| 6,124,675 A | 9/2000 | Betrand |
| 6,188,065 B1 | 2/2001 | Takada |
| 6,190,559 B1 | 2/2001 | Valaskovic |
| 6,225,623 B1 | 5/2001 | Turner |
| 6,297,499 B1 | 10/2001 | Fenn |
| 6,335,525 B1 | 1/2002 | Takada |
| 6,359,275 B1 | 3/2002 | Bertsch |
| 6,395,183 B1 | 5/2002 | Valaskovic |
| 6,562,211 B1 | 5/2003 | Kunnecke |
| 6,583,408 B2 | 6/2003 | Smith |
| 6,600,155 B1 | 7/2003 | Andrien, Jr. |
| 6,646,256 B2 | 11/2003 | Gourley |
| 6,649,907 B2 | 11/2003 | Ebeling |
| 6,670,608 B1 | 12/2003 | Taylor |
| 6,690,006 B2 | 2/2004 | Valaskovic |
| 6,713,757 B2 | 3/2004 | Tanner |
| 6,717,139 B2 | 4/2004 | Taniguchi |
| 6,723,985 B2 | 4/2004 | Schultz |
| 6,744,041 B2 | 6/2004 | Sheehan |
| 6,744,046 B2 | 6/2004 | Valaskovic |
| 6,753,523 B1 | 6/2004 | Whitehouse |
| 6,784,424 B1 | 8/2004 | Willoughby |
| 6,794,642 B2 | 9/2004 | Bateman |
| 6,803,565 B2 | 10/2004 | Smith |
| 6,806,468 B2 | 10/2004 | Laiko |
| 6,818,889 B1 | 11/2004 | Sheehan |
| 6,861,647 B2 | 3/2005 | Reilly |
| 6,875,980 B2 | 4/2005 | Bateman |
| 6,878,930 B1 | 4/2005 | Willoughby |
| 6,888,132 B1 | 5/2005 | Sheehan |
| 6,914,243 B2 | 7/2005 | Sheehan |
| 6,943,347 B1 | 9/2005 | Willoughby |
| 6,949,739 B2 | 9/2005 | Franzen |
| 6,949,740 B1 | 9/2005 | Sheehan |
| 6,949,741 B2 | 9/2005 | Cody |
| 6,956,205 B2 | 10/2005 | Park |
| 6,977,372 B2 | 12/2005 | Valaskovic |
| 6,979,816 B2 | 12/2005 | Tang |
| 6,987,264 B1 | 1/2006 | Whitehouse |
| 6,992,299 B2 | 1/2006 | Lee |
| 7,015,466 B2 | 3/2006 | Takats |
| 7,019,289 B2 | 3/2006 | Wang |
| 7,034,292 B1 | 4/2006 | Whitehouse |
| 7,041,972 B2 | 5/2006 | Bajic |
| 7,049,584 B1 | 5/2006 | Whitehouse |
| 7,053,368 B2 | 5/2006 | Thakur |
| 7,064,317 B2 | 6/2006 | McLuckey |
| 7,071,464 B2 | 7/2006 | Reinhold |
| 7,081,618 B2 | 7/2006 | Laprade |
| 7,081,621 B1 | 7/2006 | Willoughby |
| 7,095,019 B1 | 8/2006 | Sheehan |
| 7,098,452 B2 | 8/2006 | Schneider |
| 7,112,785 B2 | 9/2006 | Laramee |
| 7,138,626 B1 | 11/2006 | Karpetsky |
| 7,157,698 B2 | 1/2007 | Makarov |
| 7,161,145 B2 | 1/2007 | Oser |
| 7,196,525 B2 | 3/2007 | Sparkman |
| 7,247,495 B2 | 7/2007 | Amirav |
| 7,253,406 B1 | 8/2007 | Sheehan |
| 7,332,345 B2 | 2/2008 | Darrach |
| 7,423,261 B2 | 9/2008 | Truche |
| 7,429,731 B1 | 9/2008 | Karpetsky |
| 7,462,826 B2 | 12/2008 | Schneider |
| 7,544,933 B2 | 6/2009 | Cooks |
| 7,569,812 B1 | 8/2009 | Karpetsky |
| 7,582,864 B2 | 9/2009 | Verentchikov |
| 7,700,913 B2 | 4/2010 | Musselman |
| 7,705,297 B2 | 4/2010 | Musselman |
| 7,714,281 B2 | 5/2010 | Musselman |
| 7,772,546 B2 | 8/2010 | Jackson |
| 7,777,181 B2 | 8/2010 | Musselman |
| 7,815,484 B2 | 10/2010 | Kriman |
| 7,858,926 B1 | 12/2010 | Whitehouse |
| 7,893,408 B2 | 2/2011 | Hieftje |
| 7,915,579 B2 | 3/2011 | Chen |
| 7,923,681 B2 | 4/2011 | Collings |
| 7,928,364 B2 | 4/2011 | Musselman |
| 7,929,138 B1 | 4/2011 | Webb |
| 7,982,183 B2 | 7/2011 | Marakov |
| 7,982,185 B2 | 7/2011 | Whitehouse |
| 8,003,935 B2 | 8/2011 | Robinson |
| 8,026,477 B2 | 9/2011 | Musselman |
| 8,044,346 B2 | 10/2011 | Kostiainen |
| RE43,078 E | 1/2012 | Cody |
| 8,101,910 B2 | 1/2012 | Loboda |
| 8,207,497 B2 | 6/2012 | Musselman |
| 8,217,341 B2 | 7/2012 | Musselman |
| 8,242,459 B2 | 8/2012 | Sun |
| 8,278,619 B2 | 10/2012 | Makarov |
| 8,304,718 B2 | 11/2012 | Ouyang |
| 8,308,339 B2 | 11/2012 | Karpetsky |
| 8,334,507 B1 | 12/2012 | Whitehouse |
| 8,362,418 B2 | 1/2013 | Xu |
| 8,410,431 B2 | 4/2013 | Ouyang |
| 8,410,452 B2 | 4/2013 | Koenig |
| 8,421,005 B2 | 4/2013 | Musselman |
| 8,440,965 B2 | 5/2013 | Musselman |
| 8,481,922 B2 | 7/2013 | Musselman |
| 8,497,474 B2 | 7/2013 | Musselman |
| 8,519,354 B2 | 8/2013 | Charipar |
| 8,525,109 B2 | 9/2013 | Musselman |
| 8,563,945 B2 | 10/2013 | Musselman |
| RE44,603 E | 11/2013 | Cody |
| 8,592,756 B2 | 11/2013 | Ouyang |
| 8,592,758 B1 | 11/2013 | Nilles |
| 8,604,423 B2 | 12/2013 | Enke |
| 8,648,295 B2 | 2/2014 | Enke |
| 8,664,000 B2 | 3/2014 | Yang |
| 8,686,351 B2 | 4/2014 | Ouyang |
| 8,704,167 B2 | 4/2014 | Cooks |
| 8,710,437 B2 | 4/2014 | Cooks |
| 8,729,496 B2 | 5/2014 | Musselman |
| 8,754,365 B2 | 6/2014 | Krechmer |
| 8,766,178 B2 | 7/2014 | Ouyang |
| 8,803,085 B2 | 8/2014 | Ouyang |
| 8,816,275 B2 | 8/2014 | Ouyang |
| 8,822,949 B2 | 9/2014 | Krechmer |
| 8,853,627 B2 | 10/2014 | Ouyang |
| 8,859,956 B2 | 10/2014 | Ouyang |
| 8,859,957 B2 | 10/2014 | Ouyang |

(56) References Cited

U.S. PATENT DOCUMENTS

| | | |
|---|---|---|
| 8,859,958 B2 | 10/2014 | Ouyang |
| 8,859,959 B2 | 10/2014 | Ouyang |
| 8,859,986 B2 | 10/2014 | Cooks |
| 8,890,063 B2 | 11/2014 | Ouyang |
| 8,895,916 B2 | 11/2014 | Musselman |
| 8,895,918 B2 | 11/2014 | Cooks |
| 8,901,488 B1 | 12/2014 | Musselman |
| 8,927,926 B2 | 1/2015 | Shimada |
| 8,932,875 B2 | 1/2015 | Cooks |
| 8,933,398 B2 | 1/2015 | Ouyang |
| 8,937,288 B1 | 1/2015 | Cooks |
| 8,963,079 B2 | 2/2015 | Ouyang |
| 8,963,101 B2 | 2/2015 | Krechmer |
| 9,024,254 B2 | 5/2015 | Cooks |
| 9,064,674 B2 | 6/2015 | Ouyang |
| 9,105,435 B1 | 8/2015 | Musselman |
| 9,116,154 B2 | 8/2015 | Ouyang |
| 9,159,540 B2 | 10/2015 | Ouyang |
| 9,165,752 B2 | 10/2015 | Cooks |
| 9,224,587 B2 | 12/2015 | Krechmer |
| 9,230,792 B2 | 2/2016 | Cooks |
| 9,337,007 B2 | 5/2016 | Musselman |
| 9,390,899 B2 | 7/2016 | Musselman |
| 9,484,195 B2 | 11/2016 | Ouyang |
| 9,500,630 B2 | 11/2016 | Cooks |
| 9,514,923 B2 | 12/2016 | Krechmer |
| 9,538,945 B2 | 1/2017 | Cooks |
| 9,546,979 B2 | 1/2017 | Cooks |
| 9,548,192 B2 | 1/2017 | Cooks |
| 9,551,079 B2 | 1/2017 | Cooks |
| 9,558,926 B2 | 1/2017 | Musselman |
| 9,607,306 B2 | 3/2017 | Hieftje |
| RE46,366 E | 4/2017 | Cody |
| 9,620,344 B2 | 4/2017 | Cooks |
| 9,633,827 B2 | 4/2017 | Musselman |
| 9,700,251 B2 | 7/2017 | Cooks |
| 9,704,700 B2 | 7/2017 | Cooks |
| 9,719,181 B2 | 8/2017 | Cooks |
| 9,733,228 B2 | 8/2017 | Cooks |
| 9,824,875 B2 | 11/2017 | Musselman |
| 9,941,105 B2 | 4/2018 | Cooks |
| 9,960,029 B2 | 5/2018 | Krechmer |
| 10,004,440 B2 | 6/2018 | Cooks |
| 10,008,374 B2 | 6/2018 | Ouyang |
| 10,014,169 B2 | 7/2018 | Cooks |
| 10,056,243 B2 | 8/2018 | Musselman |
| 10,079,140 B2 | 9/2018 | Cooks |
| 10,088,461 B2 | 10/2018 | Cooks |
| 10,090,142 B2 | 10/2018 | Musselman |
| 10,113,242 B2 | 10/2018 | Cooks |
| 10,134,575 B2 | 11/2018 | Krechmer |
| 10,283,340 B2 | 5/2019 | Musselman |
| 10,395,911 B2 | 8/2019 | Cooks |
| 10,395,913 B2 | 8/2019 | Cooks |
| 10,553,417 B2 | 2/2020 | Musselman |
| 10,636,640 B2 | 4/2020 | Musselman |
| 10,643,833 B2 | 5/2020 | Krechmer |
| 10,643,834 B2 | 5/2020 | Musselman |
| 10,679,839 B2 | 6/2020 | Musselman |
| 2002/0121596 A1 | 9/2002 | Laiko |
| 2002/0121598 A1 | 9/2002 | Park |
| 2002/0162967 A1 | 11/2002 | Atkinson |
| 2002/0185593 A1 | 12/2002 | Doring |
| 2002/0185595 A1 | 12/2002 | Smith |
| 2002/0185606 A1 | 12/2002 | Smith |
| 2003/0052268 A1 | 3/2003 | Doroshenko |
| 2004/0094706 A1 | 5/2004 | Covey |
| 2004/0129876 A1 | 7/2004 | Franzen |
| 2004/0159784 A1 | 8/2004 | Doroshenko |
| 2005/0230635 A1 | 10/2005 | Takats |
| 2005/0236374 A1 | 10/2005 | Blankenship |
| 2006/0266941 A1 | 11/2006 | Vestal |
| 2007/0114389 A1 | 5/2007 | Karpetsky |
| 2007/0228271 A1 | 10/2007 | Truche |
| 2008/0156985 A1 | 7/2008 | Venter |
| 2008/0202915 A1 | 8/2008 | Hieftje |
| 2008/0217254 A1 | 9/2008 | Anderson |
| 2009/0090197 A1 | 4/2009 | Finlay |
| 2009/0090858 A1 | 4/2009 | Musselman |
| 2010/0078550 A1 | 4/2010 | Wiseman |
| 2010/0140468 A1 | 6/2010 | Musselman |
| 2011/0215798 A1 | 9/2011 | Beer |
| 2012/0006983 A1 | 1/2012 | Cody |
| 2012/0068063 A1 | 3/2012 | Fernandez |
| 2012/0145890 A1 | 6/2012 | Goodlett |
| 2012/0208004 A1 | 8/2012 | Wolcott |
| 2012/0223226 A1 | 9/2012 | Rafferty |
| 2012/0312980 A1 | 12/2012 | Whitehouse |
| 2012/0322683 A1 | 12/2012 | Liu |
| 2013/0020482 A1 | 1/2013 | Enke |
| 2013/0037710 A1 | 2/2013 | Wu |
| 2013/0092832 A1 | 4/2013 | Enke |
| 2013/0273552 A1 | 10/2013 | Ohashi |
| 2013/0284915 A1 | 10/2013 | Shimada |
| 2013/0299688 A1 | 11/2013 | Balogh |
| 2014/0024822 A1 | 1/2014 | Connolly |
| 2015/0364310 A1 | 12/2015 | Musselman |
| 2016/0314956 A1 | 10/2016 | Cooks |
| 2017/0082604 A1 | 3/2017 | Ouyang |
| 2017/0084438 A1 | 3/2017 | Cooks |
| 2017/0103879 A1 | 4/2017 | Cooks |
| 2017/0130352 A1 | 5/2017 | Cooks |
| 2017/0135613 A1 | 5/2017 | Cooks |
| 2017/0148622 A1 | 5/2017 | Musselman |
| 2017/0154761 A1 | 6/2017 | Ouyang |
| 2017/0168032 A1 | 6/2017 | Cooks |
| 2017/0221695 A1 | 8/2017 | Cooks |
| 2017/0229299 A1 | 8/2017 | Musselman |
| 2017/0248547 A1 | 8/2017 | Campbell |
| 2017/0248607 A1 | 8/2017 | Cooks |
| 2017/0273605 A1 | 9/2017 | Cooks |
| 2017/0287690 A1 | 10/2017 | Cooks |
| 2017/0309462 A1 | 10/2017 | Cooks |
| 2017/0335477 A1 | 11/2017 | Cooks |
| 2017/0343526 A1 | 11/2017 | Cooks |
| 2017/0349547 A1 | 12/2017 | Cooks |
| 2018/0017535 A1 | 1/2018 | Cooks |
| 2018/0024108 A1 | 1/2018 | Cooks |
| 2018/0033603 A1 | 2/2018 | Cooks |
| 2018/0040464 A1 | 2/2018 | Cooks |
| 2018/0043327 A1 | 2/2018 | Cooks |
| 2018/0047552 A1 | 2/2018 | Cooks |
| 2018/0061620 A1 | 3/2018 | Cooks |
| 2018/0076015 A1 | 3/2018 | Musselman |
| 2018/0188273 A1 | 7/2018 | Cooks |
| 2018/0204712 A1 | 7/2018 | Cooks |
| 2018/0247804 A1 | 8/2018 | Shelley |
| 2018/0275118 A1 | 9/2018 | Cooks |
| 2018/0279927 A1 | 10/2018 | Cooks |
| 2018/0286651 A1 | 10/2018 | Ouyang |
| 2018/0330934 A1 | 11/2018 | Cooks |
| 2019/0206668 A1 | 7/2019 | Cooks |
| 2019/0219555 A1 | 7/2019 | Cooks |
| 2019/0237315 A1 | 8/2019 | Cooks |
| 2019/0371592 A1 | 12/2019 | Musselman |
| 2020/0020516 A1 | 1/2020 | Cooks |
| 2020/0110010 A1 | 4/2020 | Pawliszyn |
| 2020/0121229 A1 | 4/2020 | Cooks |

FOREIGN PATENT DOCUMENTS

| | | |
|---|---|---|
| GB | 2263578 | 7/1993 |
| JP | 50-106694 | 8/1975 |
| JP | 51-120288 | 10/1976 |
| JP | 52-91494 | 8/1977 |
| JP | 60-41748 | 3/1985 |
| JP | 2003185635 | 7/2003 |
| JP | 2003222574 | 8/2003 |
| JP | 2005-150027 | 6/2005 |
| JP | 2007525677 | 6/2007 |
| JP | 2009539114 | 11/2009 |
| WO | WO03025973 | 3/2003 |
| WO | WO03081205 | 10/2003 |
| WO | WO2004068131 | 8/2004 |

(56) References Cited

FOREIGN PATENT DOCUMENTS

| WO | WO2005094389 | 10/2005 |
| --- | --- | --- |
| WO | WO2008054393 | 5/2008 |
| WO | WO2008082603 | 7/2008 |
| WO | WO2015195599 | 12/2015 |
| WO | WO2016145041 | 9/2016 |
| WO | WO2017040359 | 3/2017 |
| WO | WO2017053911 | 3/2017 |
| WO | WO2017070478 | 4/2017 |
| WO | WO2017079193 | 5/2017 |
| WO | WO2017127670 | 7/2017 |
| WO | WO2017132444 | 8/2017 |
| WO | WO2017180871 | 10/2017 |
| WO | WO2018175713 | 9/2018 |

OTHER PUBLICATIONS

Cody, R.B. et al., "Versatile New Ion Source for the Analysis of Materials in Open Air under Ambient Conditions" Anal. Chem., 2005, 77, 2297-2302.

Cooks, R.G. et al., "Ambient Mass Spectrometry", Science, 2006, 311, 1566-1570.

Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.

Garimella, S. et al., "Gas-flow assisted ion transfer for mass spectrometry", J. Mass Spectrom. 2012, 17, 201-207.

Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.

Haddad, R., et al., "Easy Ambient Sonic-Spray Ionization Mass Spectrometry Combined with Thin-Layer Chromatography," *Analytical Chemistry*, vol. 80, No. 8, Apr. 15, 2008, pp. 2744-2750.

Harris, Glenn A. et al., Ambient Sampling/Ionization Mass Spectrometry: Applications and Current Trends, Apr. 15, 2011, Anal. Chem. 2011, 83, pp. 4508-4538.

Harris, Glenn A. et al., Simulations and Experimental Investigation of Atmospheric Transport in an Ambient Metastable-Induced Chemical Ionization Source, Anal. Chem. 2009, 81, pp. 322-329.

Hill, C.A. et al., "A pulsed corona discharge switchable high resolution ion mobility spectrometer-mass spectrometer", Analyst, 2003, 128, pp. 55-60.

Hiraoka, K. et al., "Atmospheric-Pressure Penning Ionization Mass Spectrometry", Rapid Commun. Mass Spectrom., 18, 2004, pp. 2323-2330.

McLuckey, S.A. et al., "Atmospheric Sampling Glow Discharge Ionization Source for the Determination of Trace Organic Compounds in Ambient Air", Anal. Chem., 60, 1988, pp. 2220-2227.

Otsuka, K. et al., "An Interface for Liquid Chromatograph/Liquid Ionization Mass Spectrometer", Analytical Sciences, Oct. 1988, vol. 4, pp. 467-472.

Takáts et al., "Mass Spectrometry Sampling Under Ambient Conditions with Desorption Electrospray Ionization," Science, vol. 306, No. 5695, Oct. 15, 2004, pp. 471-473.

Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.

Ifa et al., Ambient Ionization Mass Spectrometry for Cancer Diagnosis and Surgical Margin Evaluation, Clinical Chem., (2016) 62, 111-123.

Yang et al., Argon Direct Analysis in Real Time Mass Spectrometry in Conjunction with Makeup Solvents: A Method for Analysis of Labile Compounds, Anal Chem., (2013) 83, 1305-1309.

Yu et al., Bioanalysis without Sample Cleanup or Chromatography: The Evaluation and Initial Implementation of Direct Analysis in Real Time Ionization Mass Spectrometry for the Quantification of Drugs in Biological Matrixes, Anal Chem., (2009) 81, 193-202.

Zang et al., Comparison of Ambient and Atmospheric Pressure Ion Sources for Cystic Fibrosis Exhaled Breath Condensate Ion Mobility-Mass Spectrometry Metabolomics, J. Am. Soc. Mass Spectrom., (2017) 28, 1489-1496.

Zhang et al., Will Ambient Ionization Mass Spectrometry Become an Integral Technology in the Operating Room of the Future?, Clinical Chem., (2016) 62, 1172-1174.

Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.

International Search Report, Application No. PCT/US2007/63006, dated Feb. 5, 2008, 8 pages.

Extended European Search Report, Application No. 07757665.0 PCT/US2007/063006 dated Jan. 7, 2010, 8 pages.

Article 94(3) European Communication, Application No. 07757665.0 PCT/US2007/063006, dated Mar. 14, 2012, 9 pages.

International Search Report, Application No. PCT/US2007/69823, dated Feb. 15, 2008, 8 pages.

Extended European Search Report, Application No. 07797812.0 PCT/US2007/069823, dated Apr. 4, 2010, 9 pages.

Article 94(3) European Communication, Application No. 07797812.0 PCT/US2007/069823, dated Jul. 27, 2012, 9 pages.

International Search Report, Application No. PCT/US2007/69821, dated Feb. 7, 2008.

Extended European Search Report, Application No. 07797811.2 PCT/US2007/069821, dated Mar. 25, 2010, 9 pages.

European Summons, Application No. 07797811.2 PCT/US2007/069821, Feb. 18, 2013, 8 pages.

International Search Report, Application No. PCT/US2007/81439, dated Mar. 20, 2008, 9 pages.

Extended European Search Report, Application No. 07844307.4 PCT/US2007/081439, dated Apr. 14, 2010, 12 pages.

Japanese Office Action, Application No. 2008-558459 PCT/US2007/063006, dated Jan. 19, 2012, 4 pages.

Unofficial Translation of Japanese Office Action, Application No. 2008-558459 PCT/US2007/063006, dated Jan. 19, 2012, 5 pages.

Chinese Office Action, Application No. 200780015974.5 PCT/US2007/063006, dated Feb. 2, 2012, 5 pages.

Chinese Office Action, Application No. 200780015974.5 PCT/US2007/063006, dated Sep. 25, 2012, 8 pages.

Chinese Office Action, Application No. 200780015974.5 PCT/US2007/063006, dated Dec. 26, 2012, 7 pages.

International Search Report, Application No. PCT/US2012/000061, dated Aug. 6, 2013, 8 pages.

Oral Proceedings European Communication, Application No. 07757665.0 PCT/US2007/063006, dated Sep. 3, 2013, 5 pages.

Korean Patent Application 7024130/2008 Office Action, dated Jun. 29, 2013, 3 pages.

Korean Patent Application 7024130/2008 Office Action, translation, dated Jun. 29, 2013, 3 pages.

Article 94(3) European Communication, Application No. 07797811.2 PCT/US2007/069821, dated Feb. 2, 2012, 8 pages.

Summons Application No. 07797811.2 PCT/US2007/069821, Feb. 18, 2013, 10 pages.

Chinese Office Action, Application No. 201280003101.3, PCT/US12/00061, dated Jan. 22, 2016, 3 pages.

Translation of Chinese Office Action, Application No. 201280003101.3, PCT/US12/00061, dated Jan. 22, 2016, 18 pages.

Japanese Office Action, Application No. 2013552527, PCT/US12/00061, dated Jan. 22, 2016, 3 pages.

Translation of Japanese Office Action, Application No. 2013552527, PCT/US12/00061, dated Jan. 22, 2016, 4 pages.

Extended European Search Report, Application No. 12742544.5, PCT/US20012/0000061, dated Sep. 12, 2017, 9 pages.

Form 1224, Preliminary amendment, EP Application No. 12742544.5, PCT/US2001/0000061, dated Mar. 22, 2018, 7 pages.

Amended Claims, EP Application No. 12742544.5, PCT/US20012/0000061, Mar. 22, 2018, 3 pages.

Gibbins, J.R., 'Variable Heating Rate Wire Mesh Pyrolysis Apparatus' Rev. Sci. Instr. 60 (1989) pp. 1129-1139.

Korean Patent Application, Application No. 10-2013-7008108, Notice of Final Rejection, dated Jun. 7, 2018, 2 pages.

(56) References Cited

OTHER PUBLICATIONS

Korean Patent Application, Application No. 10-2013-7008108, Notice of Final Rejection, dated Sep. 5, 2018, 6 pages.
Translation of Korean Patent Application, Application No. 10-2013-7008108, Notice of Final Rejection, dated Sep. 5, 2018, 5 pages.
Korean Patent Application, Application No. 10-2013-7008108, Response to Notice of Final Rejection, Amendment dated Oct. 31, 2018, 3 pages.
Machine Translation of Amendment, Response to Notice of Final Rejection in Korean Patent Application, Application No. 10-2013-7008108, dated Oct. 31, 2018, 2 pages.
Korean Patent Application, Application No. 10-2013-7008108, Response to Notice of Final Rejection, Argument dated Oct. 31, 2018, 12 pages.
Machine Translation of Argument, Response to Notice of Final Rejection in Korean Patent Application, Application No. 10-2013-7008108, dated Oct. 31, 2018, 27 pages.
International Search Report, Application No. PCT/US19/34041, dated Nov. 1, 2019, 4 pages.

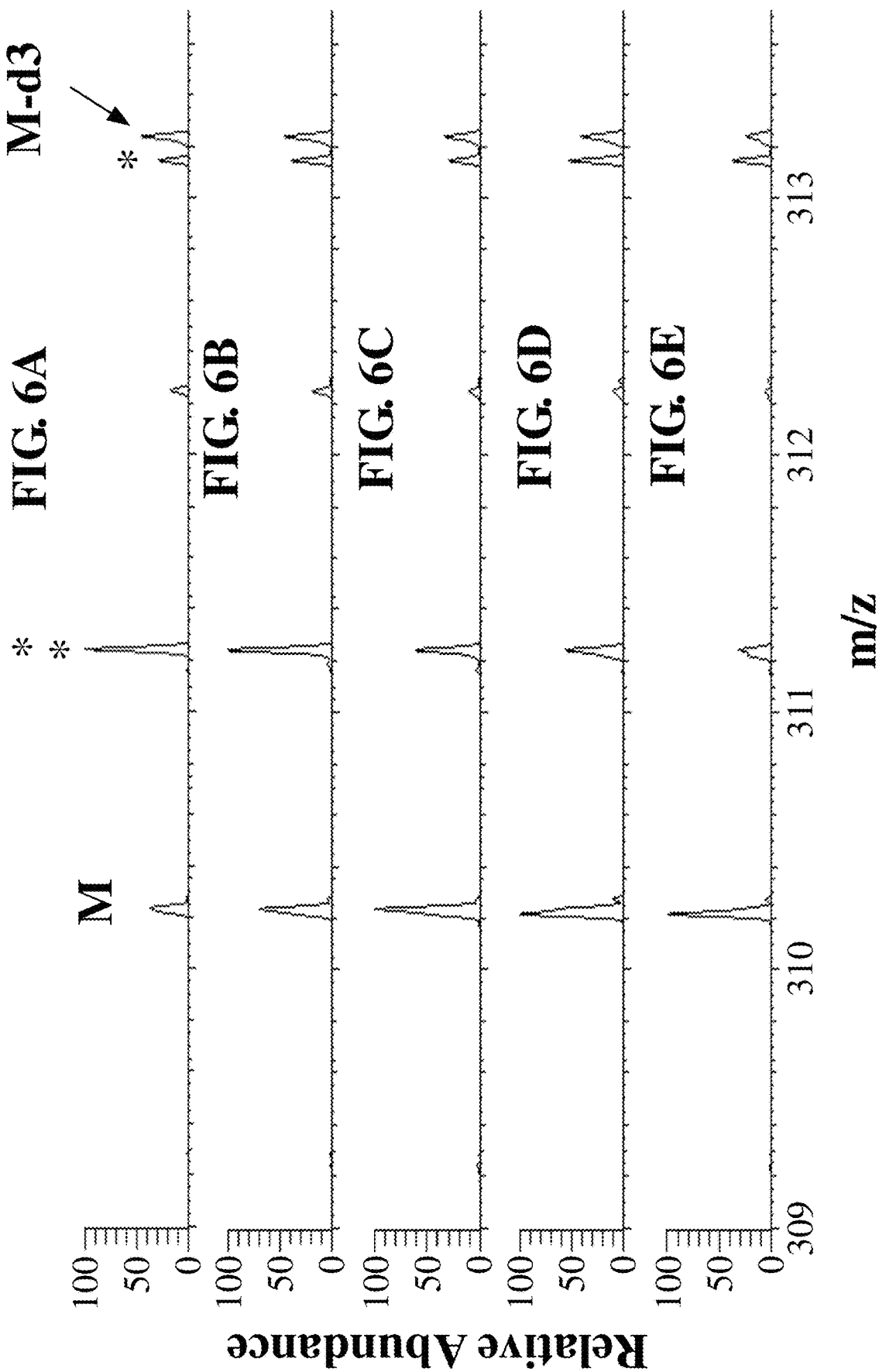

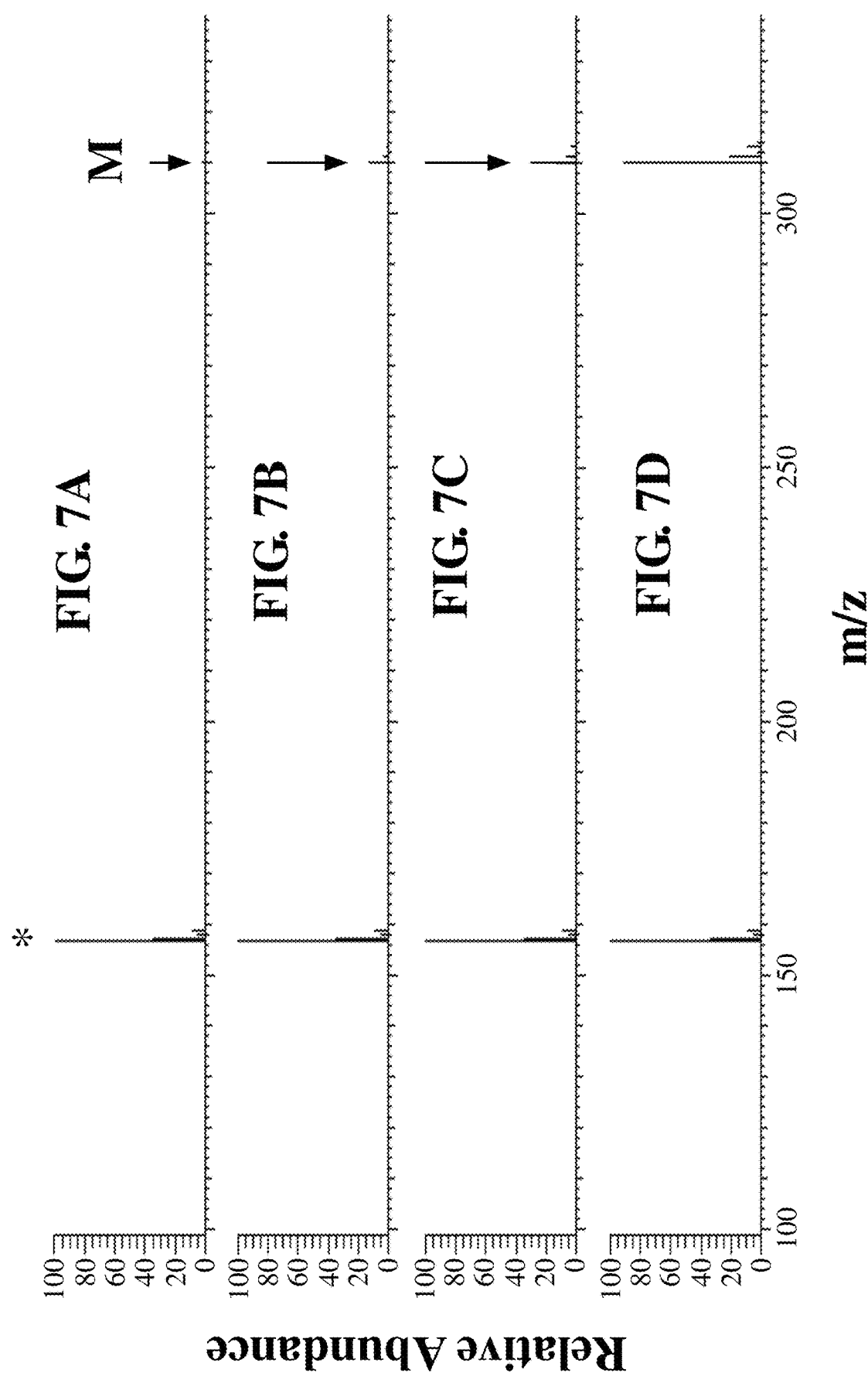

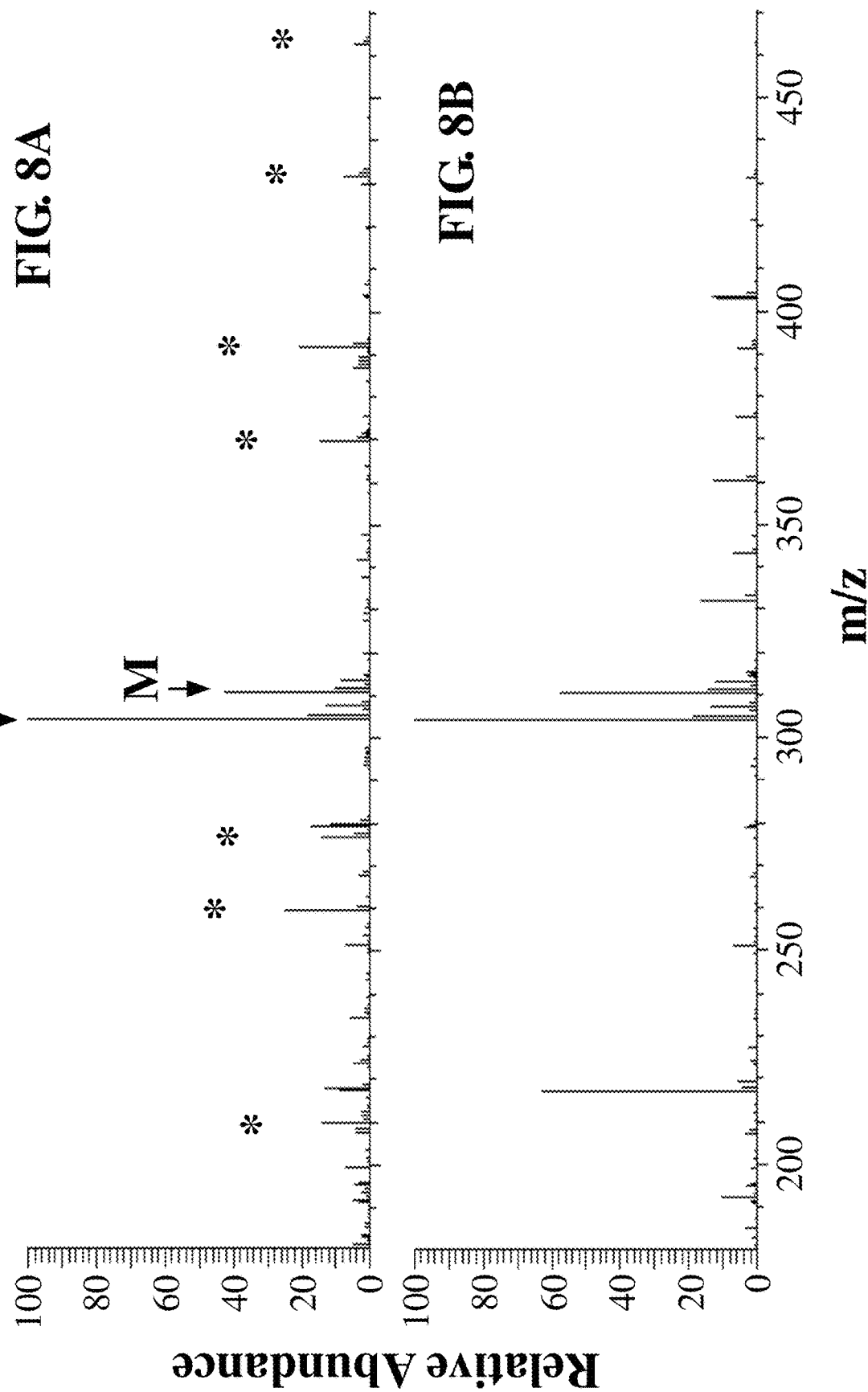

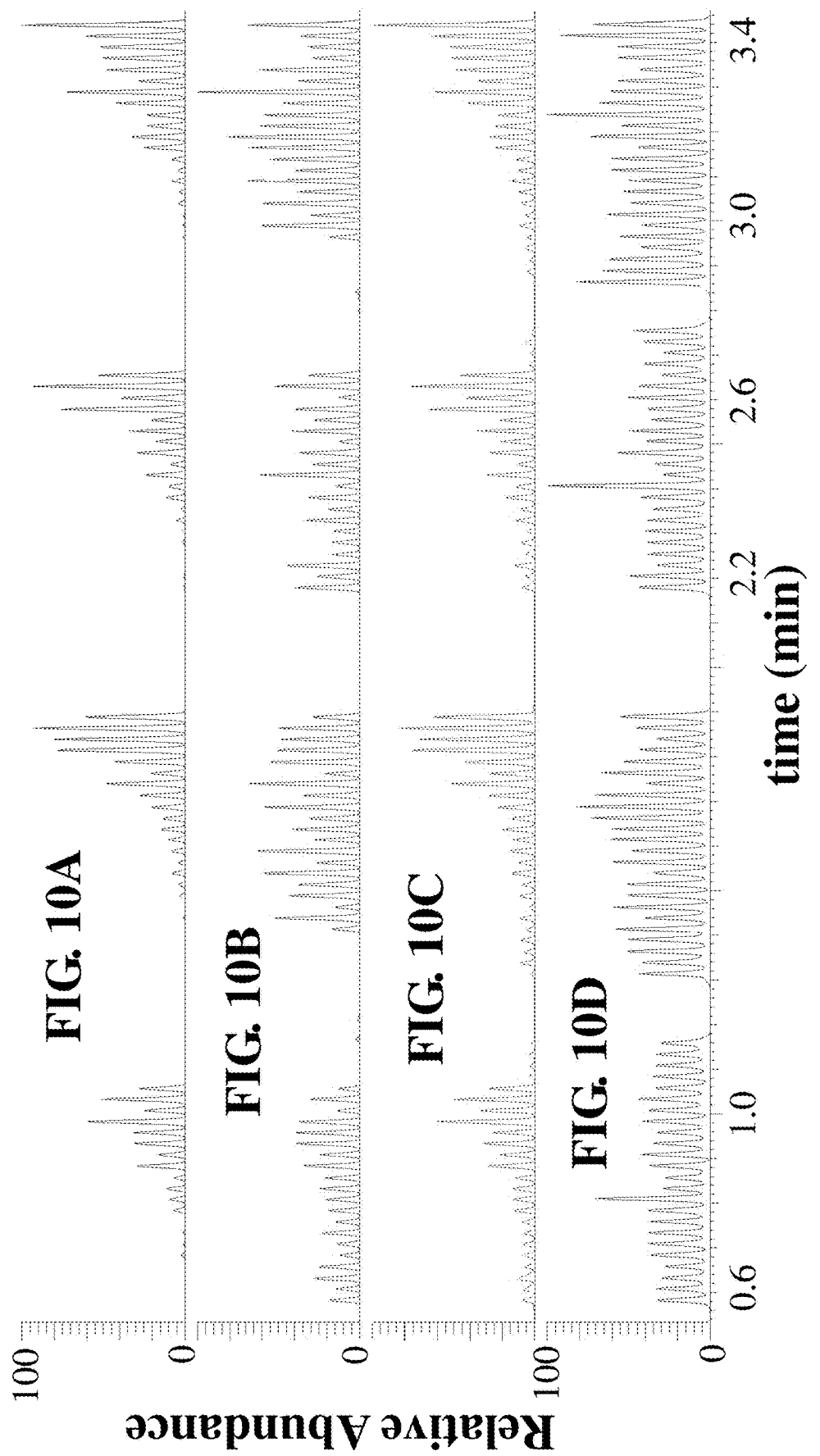

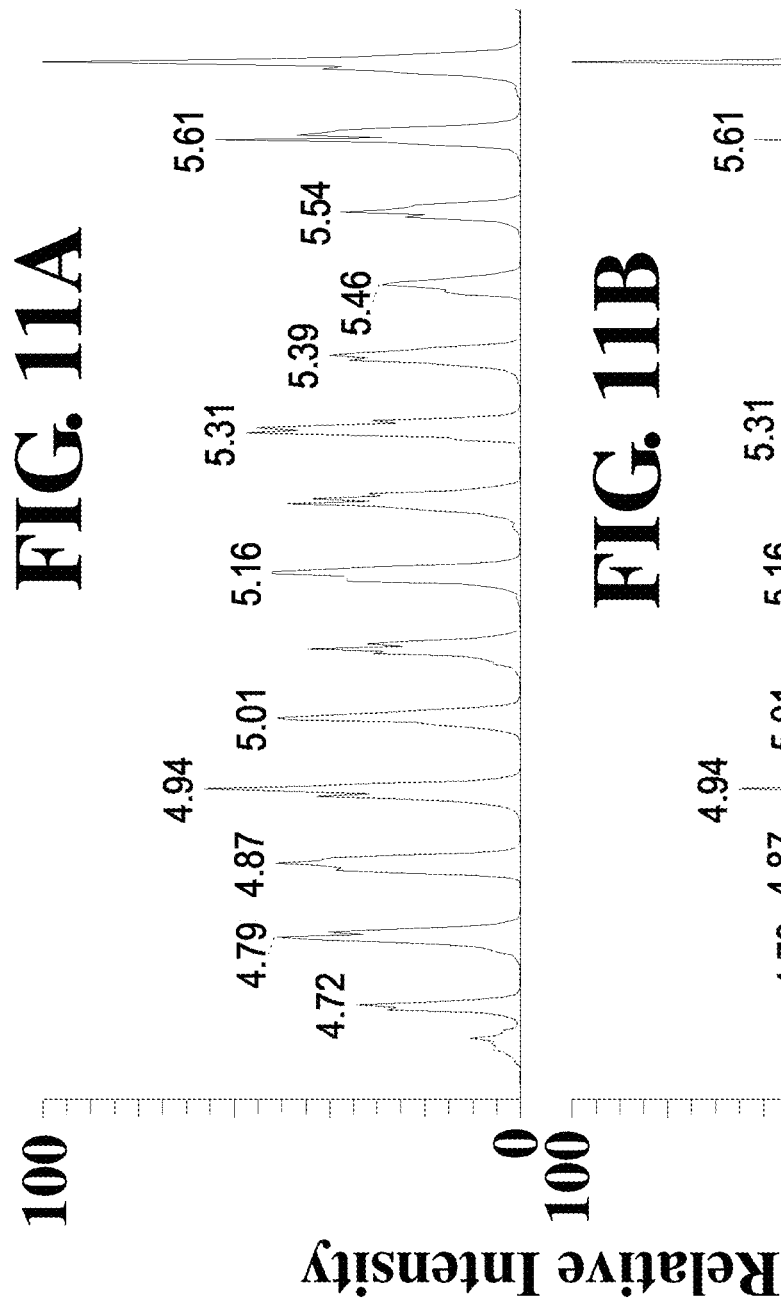

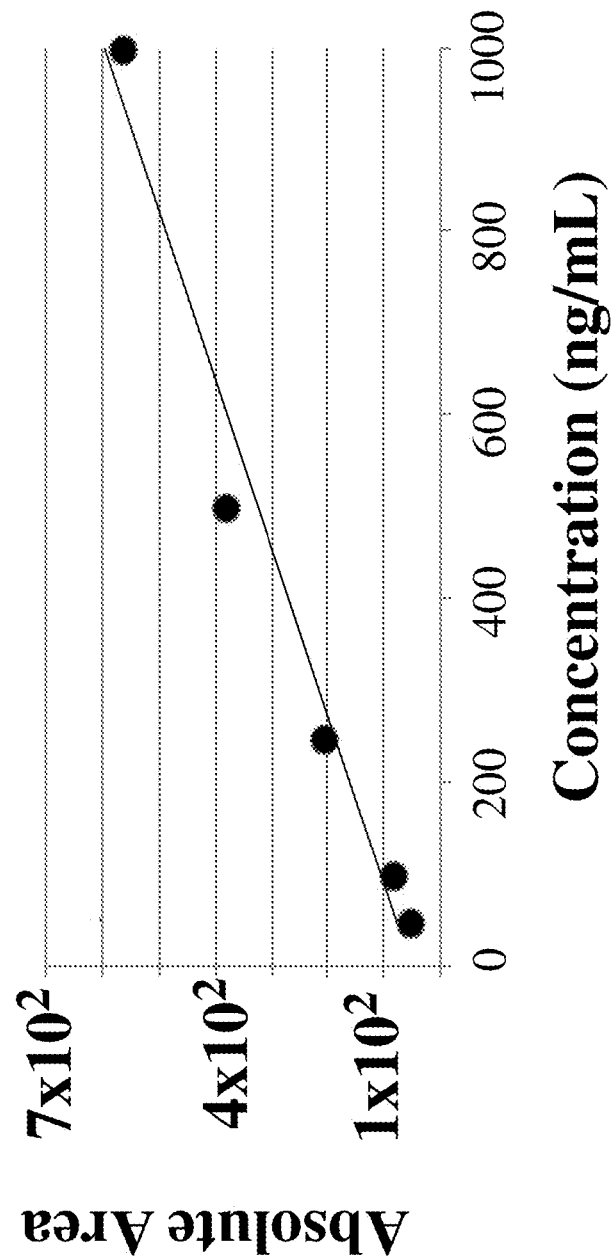

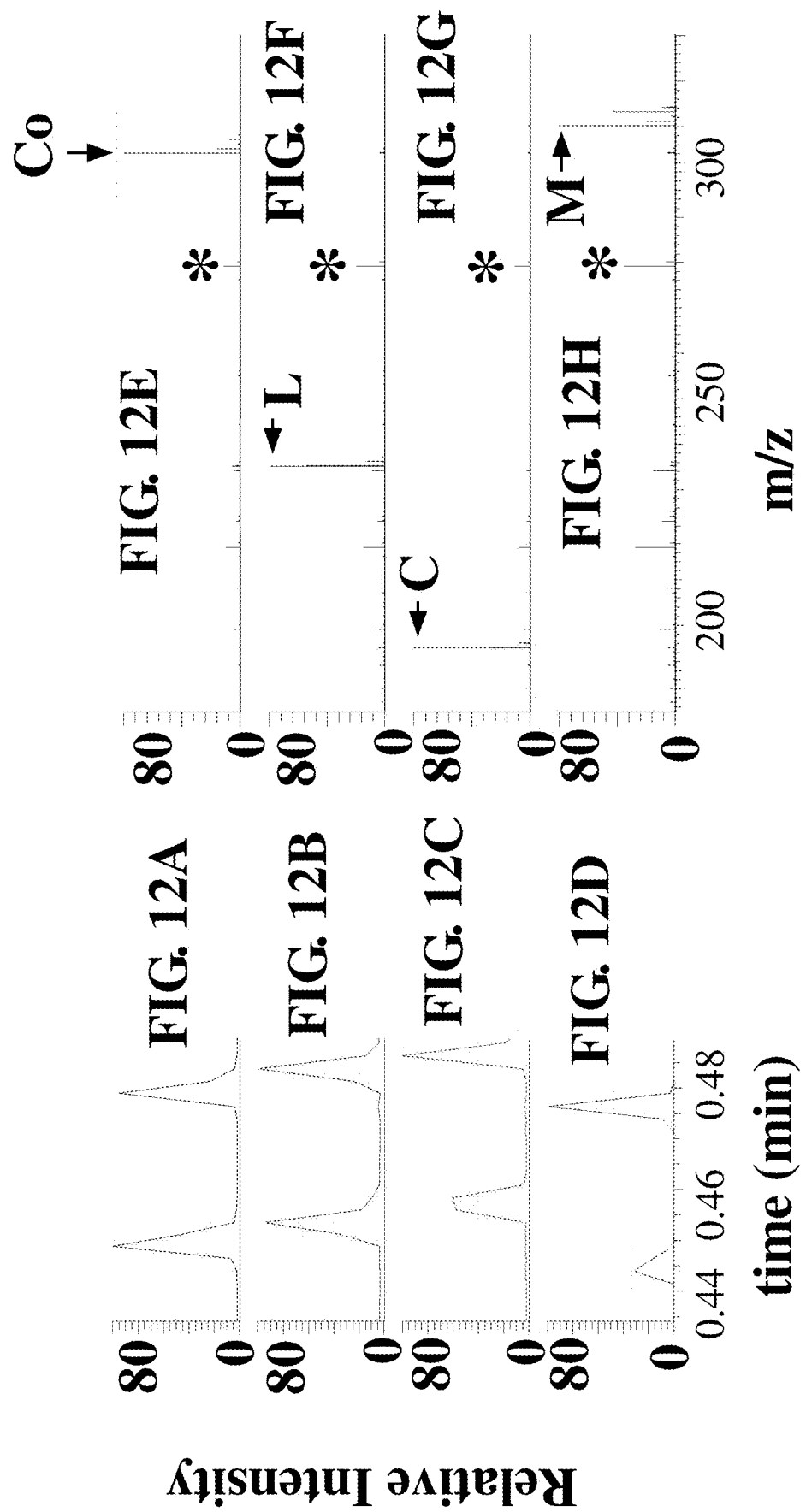

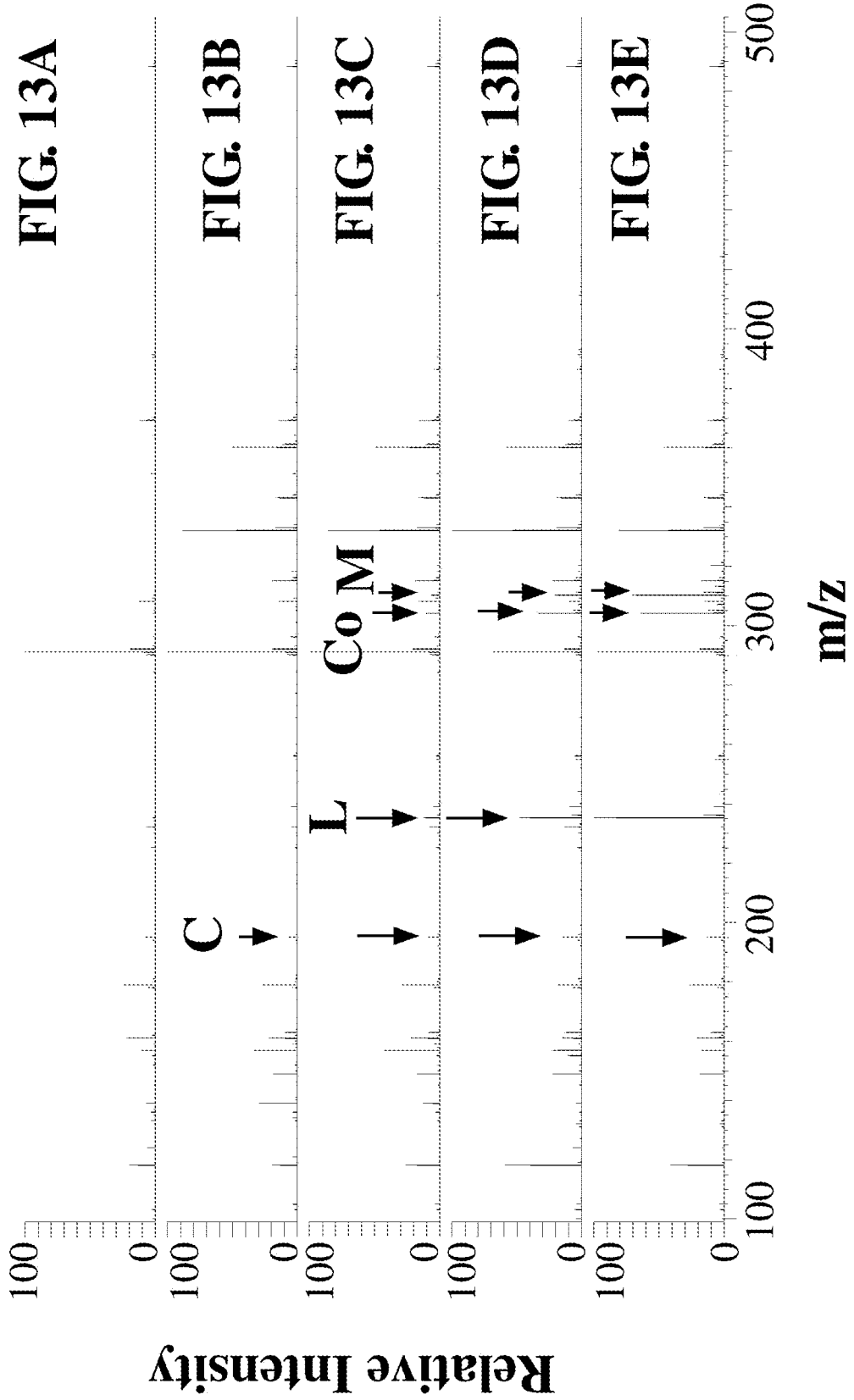

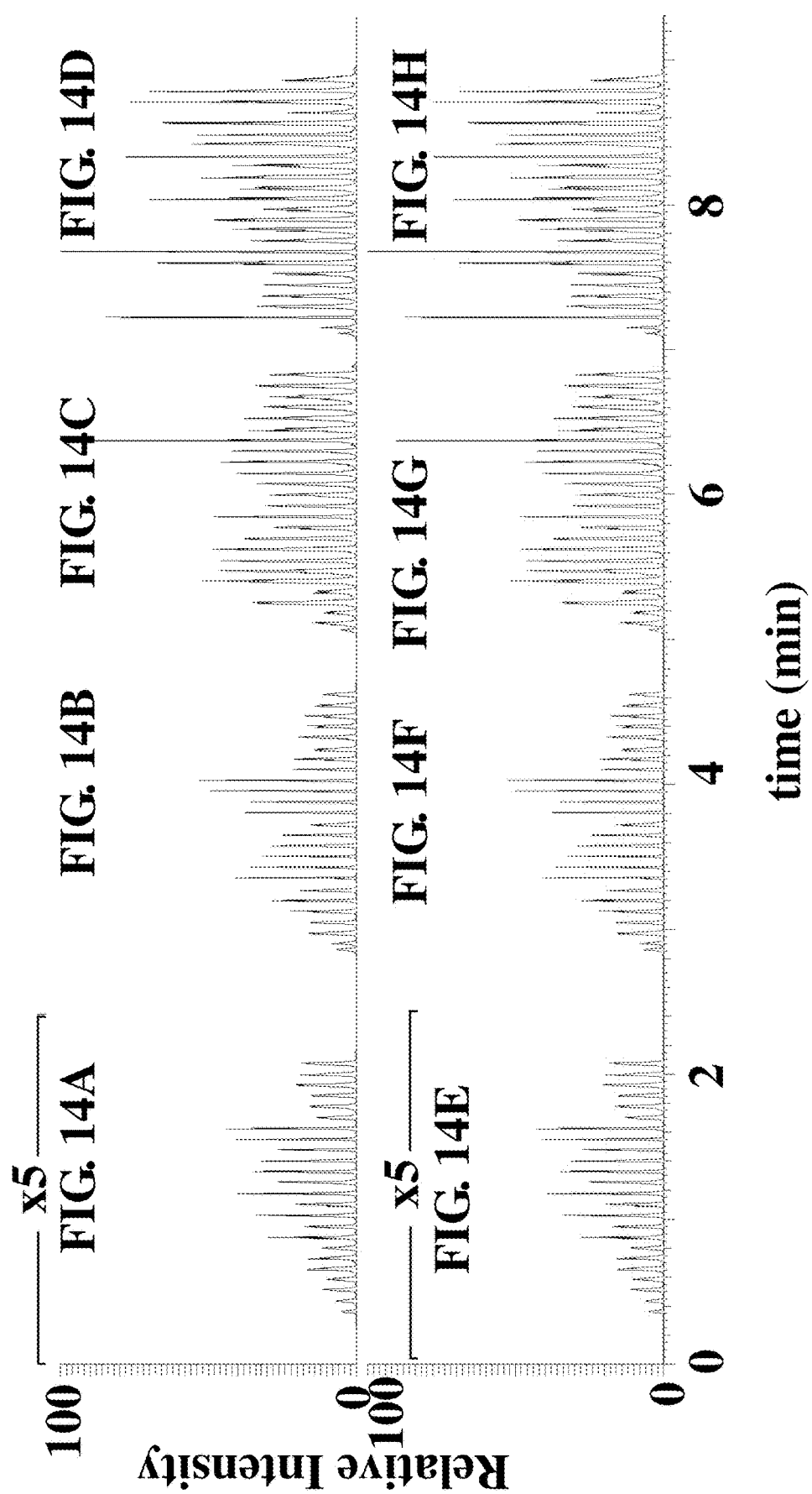

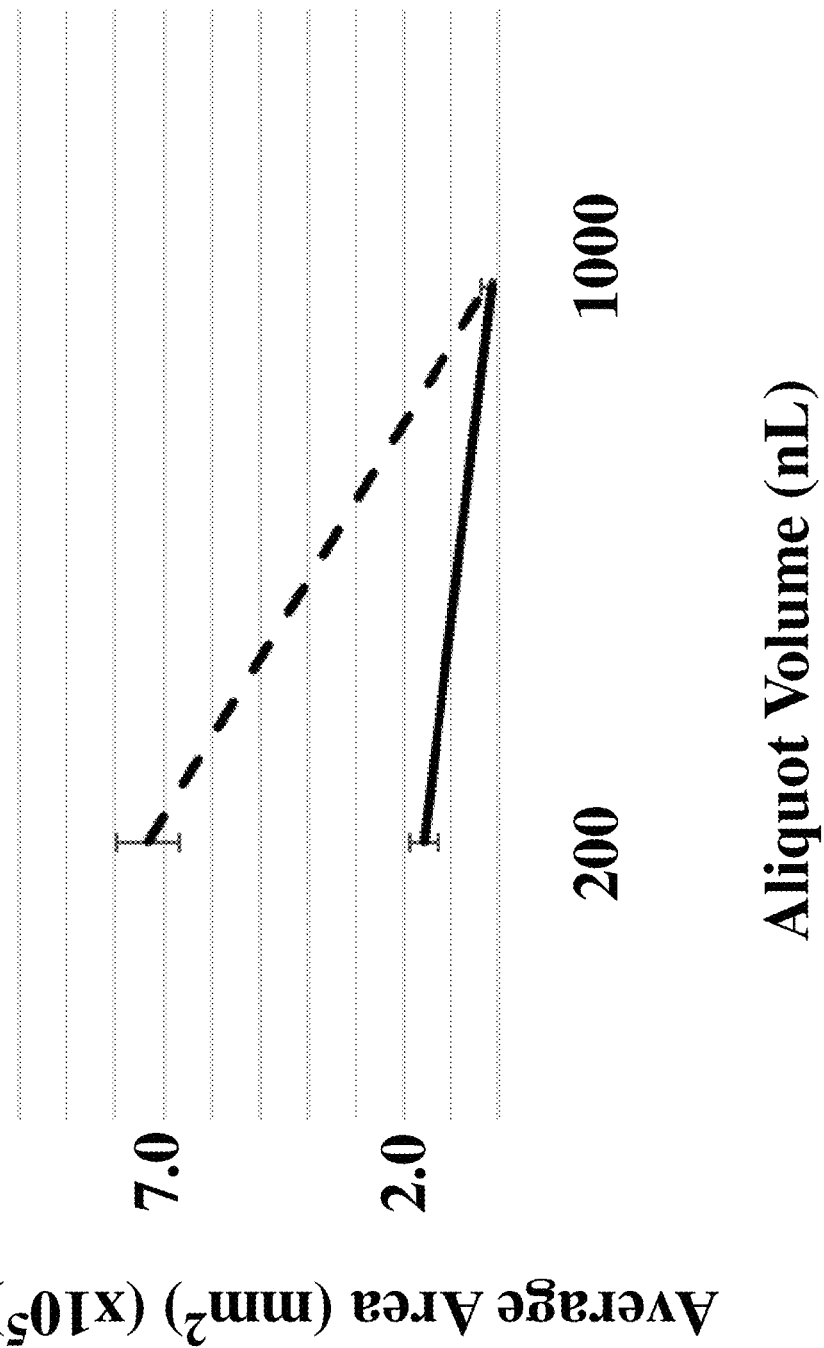

APPARATUS AND METHOD FOR REDUCING MATRIX EFFECTS

PRIORITY

This application claims priority to the U.S. Provisional Patent Application No. 62/679,668 entitled "APPARATUS AND METHOD FOR REDUCING MATRIX EFFECTS", by inventor Brian D. Musselman, filed Jun. 1, 2018, which is incorporated herein by reference in its entirety and for all purposes.

FIELD OF THE INVENTION

The present invention relates to methods and devices for chemical analysis of molecules being ionized in ambient atmosphere where matrix effects are common.

BACKGROUND OF THE INVENTION

Analysis of molecules of interest at ambient atmosphere in a laboratory or field setting can be accomplished using an ionizing gas to convert the molecules of interest to ions and directing or evacuating the ions into a spectrometer. However, the ambient atmosphere in a laboratory or field setting can contain many 'background chemicals' that can also be detected. These background chemicals can vary based on the local environment. For example, trace chemicals present in the atmosphere of a laboratory might contain solvents, dust particles, aerosols, counter-ions, and chemicals being used for synthesis or extractions. Further, the background can include chemicals from human, animal, bacterial, viral or fungi activity including from the presence of the spectrometer operator/scientist including breath, perfume, fragrances, mouthwash, cosmetics, perspiration, flatulence, bacterial gasses, and bacterial odors. The presence of any one or more of these can lead to the generation of a persistent background. When the background becomes too abundant the process of ambient ionization and ion detection of molecules of interest can become inefficient in that the molecules of interest cannot be detected or are detected at such low abundance that they are obscured from detection by the detection of the background chemicals.

Trace chemicals present in the sample of interest can also be considered as background chemicals since they are present in the ionizing region but are not of interest. These include chemicals originating from the sample container, solvent residues, chemicals that are normally present but not important to characterization of the sample, and chemicals that might be introduced into the air surrounding the ionization gas including those from human activity such as solvents, or from other nearby analytical endeavors. For example, in a sample of urine the metabolite creatinine, a chemical waste product produced by muscle metabolism, is easily ionized and detected using a spectrometer. The kidneys filter creatinine and other waste products including urea out of circulating blood allowing them to be removed from the body through urination, see TABLE III and FIG. 4A (which show the species observed in the positive ionization mode) DART® mass spectra of urine. Thus both of these compounds (creatinine and urea) are present as background chemicals during analysis of fluids from human origin (see TABLE IV which shows species observed in the positive ionization mode DART mass spectra of saliva). Further, urea itself is difficult to extract from urine which is why the analysis of drugs of abuse in workplace drug testing from urine is normally undertaken using chromatographic material to separate urea from the molecules of interest. The chromatographic material delays passage of the larger drug molecules while allowing the urea to be directed to waste. In the absence of the urea the larger drug molecules are ionized in the ambient atmosphere and after entering the spectrometer are easily detected.

Solvent effects can also contribute to background chemicals e.g. solvents used to dissolve samples such as dimethyl sulfoxide (DMSO), and chemicals added to samples to facilitate pH change or buffering that ionize might also contribute to the background.

In theory and practice eliminating background chemicals prior to the ambient ionization reduces the background chemical ions, i.e., the chemical noise, permitting the ionization of molecules of interest to be detected.

SUMMARY OF THE INVENTION

In an embodiment of the present invention in an ambient ionization experiment, limiting the abundance of background chemicals present in the ionization region prior to desorption ionization of sample into that region, decreases the suppression of ions of interest. In an embodiment of the present invention, the reduction of unwanted chemicals in the ionization region can be effected by limiting the sample volume. In an embodiment of the present invention in the ambient ionization experiment, if the background chemical molecules are reduced, then it is only necessary to ionize more efficiently than or as efficiently as the remaining background chemical molecules. In an embodiment of the present invention in the ambient ionization experiment, dilution of the sample with a solvent which does not compete with the ionization of the molecules of interest, such as water can be used to reduce the contribution of the background chemicals and thereby increase the sensitivity of detection of molecules of interest. In an embodiment of the present invention in the ambient ionization experiment, the addition of a volume of background chemical to suppress ionization of other background chemicals permits more efficient ionization and detection of molecules of interest. In an embodiment of the present invention in the ambient ionization experiment, adding a specific background chemical differs from the addition of dopant chemicals which increase overall ionization. The method has implication for plasma-based ambient ionization with spectrometers including mass and ion mobility spectroscopy systems.

BRIEF DESCRIPTION OF THE DRAWINGS

All DART measurements were carried out at 250° C. unless otherwise specified. All Mosquito spotting was carried out in serpentine mode. All mass spectrometry was carried out on a THERMO SCIENFIC™ Q-EXACTIVE™ mass spectrometer. Various embodiments of the present invention will be described in detail based on the following Figures, where:

FIG. 6A is a positive partial (309-314 Da) DART API mass spectrum from the analysis of 200 nL of urine to which 50, nanograms/milliLiter (ng/mL) of methadone (top) and 200 ng/mL of methadone-d3 as an internal standard are applied to a mesh, according to an embodiment of the invention;

FIG. 6B is a positive partial (309-314 Da) DART API mass spectrum from the analysis of 200 nL urine sample to which 100 ng/mL of methadone (top) and 200 ng/mL of methadone-d3 as an internal standard are applied to a mesh, according to an embodiment of the invention;

FIG. 6C is a positive partial (309-314 Da) DART API mass spectrum from the analysis of 200 nL urine sample to which 250 ng/mL of methadone (top) and 200 ng/mL of methadone-d3 as an internal standard are applied to a mesh, according to an embodiment of the invention;

FIG. 6D is a positive partial (309-314 Da) DART API mass spectrum from the analysis of 200 nL urine sample to which 500 and 1000 ng/mL of methadone (top) and 200 ng/mL of methadone-d3 as an internal standard are applied to a mesh, according to an embodiment of the invention;

FIG. 6E is a positive partial (309-314 Da) DART API mass spectrum from the analysis of 200 nL urine sample to which 1000 ng/mL of methadone (top) and 200 ng/mL of methadone-d3 as an internal standard are applied to a mesh, according to an embodiment of the invention;

FIG. 7A is a positive DART API mass spectrum (100-350 Da) of 2000 nL volume of 0.002 mg of methadone dissolved in DMSO, are applied to a mesh, according to an embodiment of the invention;

FIG. 7B is a positive DART API mass spectrum (100-350 Da) of 2000 nL volume of 0.01 mg of methadone dissolved in DMSO, are applied to a mesh, according to an embodiment of the invention;

FIG. 7C is a positive DART API mass spectrum (100-350 Da) of 2000 nL volume of 0.02 mg of methadone dissolved in DMSO, are applied to a mesh, according to an embodiment of the invention;

FIG. 7D is a positive DART API mass spectrum (100-350 Da) of 2000 nL volume of 40 µg of methadone dissolved in DMSO, are applied to a mesh, according to an embodiment of the invention;

FIG. 8A is a positive DART API n mass spectrum (180-470 Da) of 1000 nL of urine spiked with a mixture of 500 pg of methadone and 500 pg cocaine and spotted by a Mosquito onto a QUICKSTRIP®, according to an embodiment of the invention;

FIG. 8B is a positive DART API mass spectrum (180-470 Da) of 1000 nL deposited made up of 50% urine with 50% DMSO and spiked with a mixture of 250 pg of methadone and 250 pg cocaine and spotted by a Mosquito onto a QuickStrip, according to an embodiment of the invention;

FIG. 10A is an Extracted Ion Chromatogram (EIC) showing the intensity of the cocaine (m/z 304) intact species generated using direct analysis by a positive DART API of urine samples (the urine samples were doped with a mixture of varying concentrations of cocaine, varying concentrations of methadone, a constant concentration of cocaine-d3, and a constant concentration of methadone-d3) spotted by a Mosquito onto a QuickStrip, according to an embodiment of the invention;

FIG. 10B is an EIC showing the intensity of the cocaine-d3 (m/z 307) intact species generated using direct analysis by a positive DART API of urine samples (the urine samples were doped with a mixture of varying concentrations of cocaine, varying concentrations of methadone, a constant concentration of cocaine-d3, and a constant concentration of methadone-d3) spotted by a Mosquito onto a QuickStrip, according to an embodiment of the invention;

FIG. 10C is an EIC showing the intensity of the methadone (m/z 310) intact species generated using direct analysis by a positive DART API of urine samples (the urine samples were doped with a mixture of varying concentrations of cocaine, varying concentrations of methadone, a constant concentration of cocaine-d3, and a constant concentration of methadone-d3) spotted by a Mosquito onto a QuickStrip, according to an embodiment of the invention;

FIG. 10D is an EIC showing the intensity of the urea tetramer (m/z 241) intact species generated using direct analysis by a positive DART API of urine samples (the urine samples were doped with a mixture of varying concentrations of cocaine, varying concentrations of methadone, a constant concentration of cocaine-d3, and a constant concentration of methadone-d3) spotted by a Mosquito onto a QuickStrip, according to an embodiment of the invention;

Figure 11D:
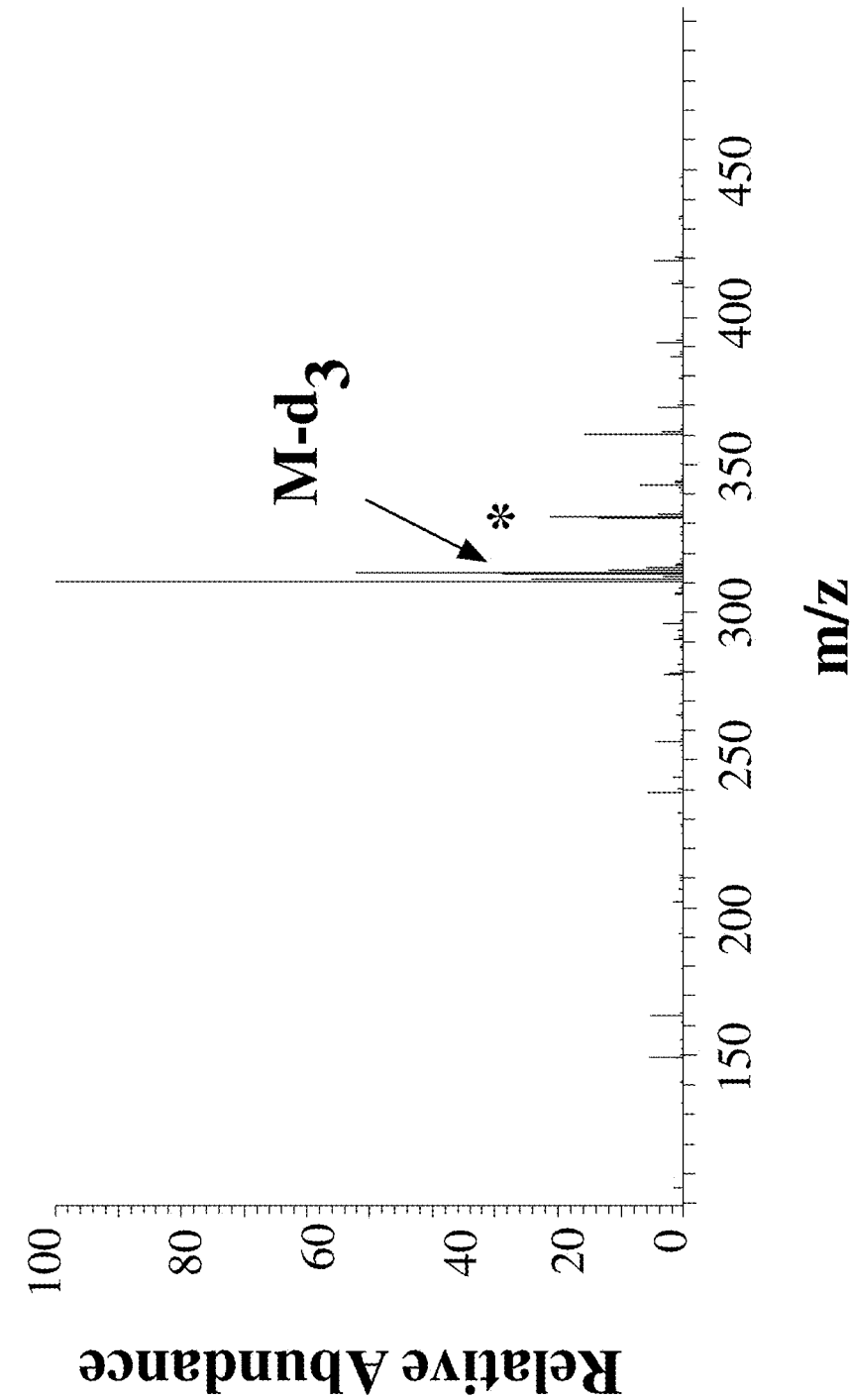
Figure 15A:
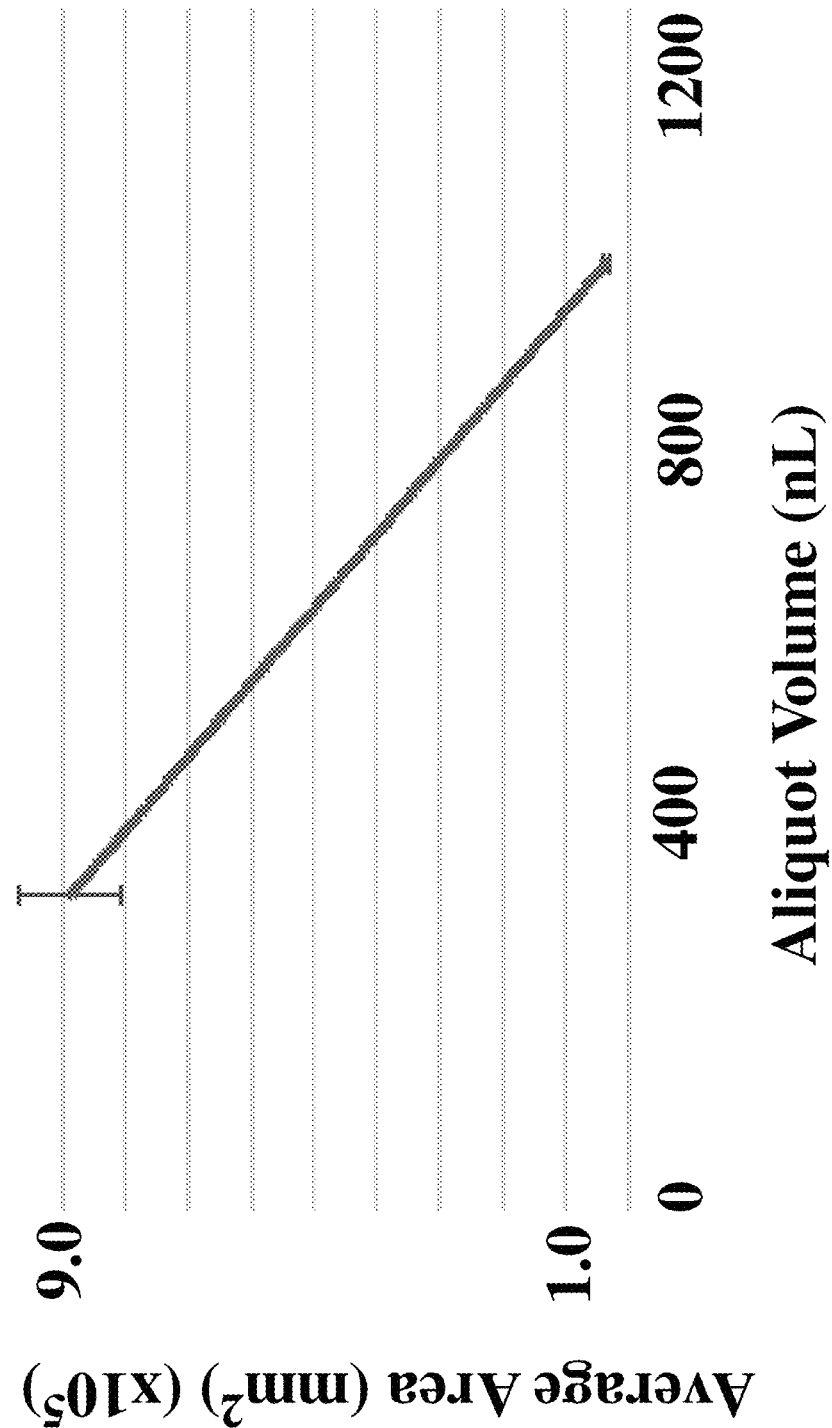
Figure 15B:
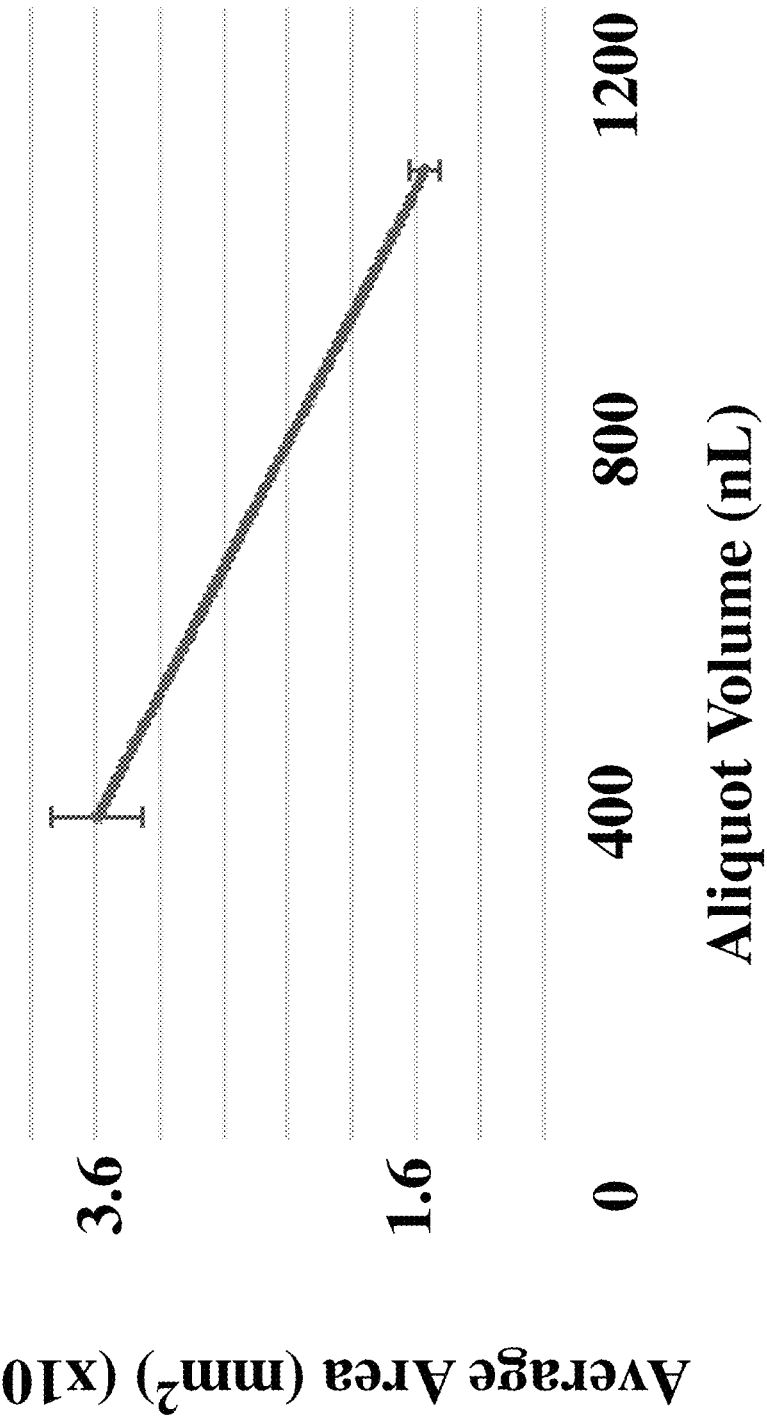
Figure 16A:
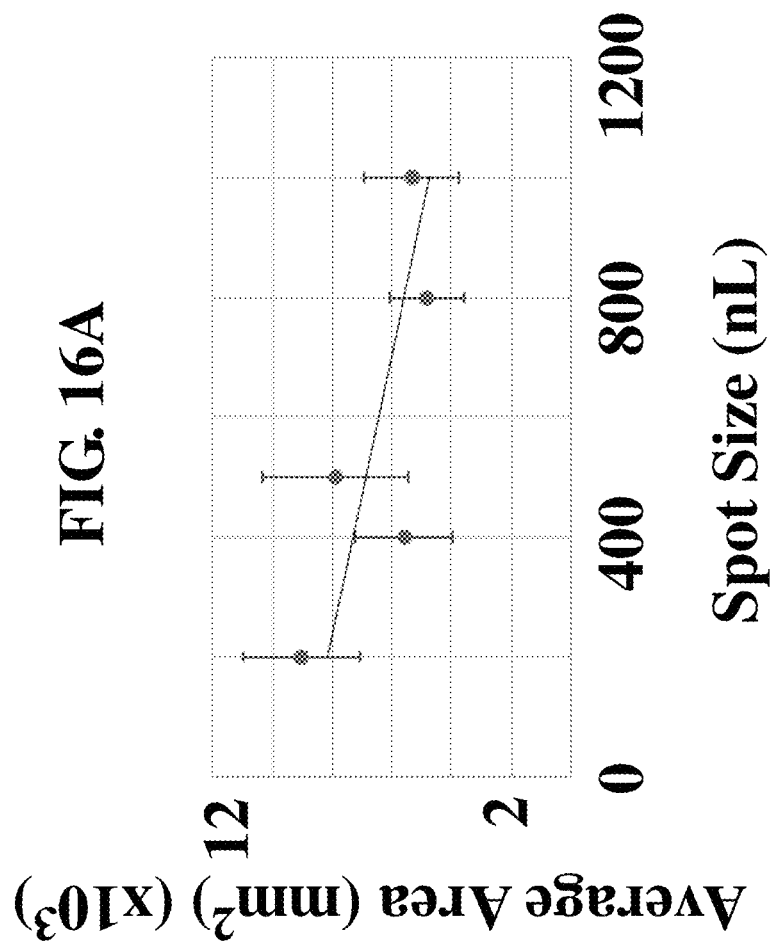
Figure 16B:
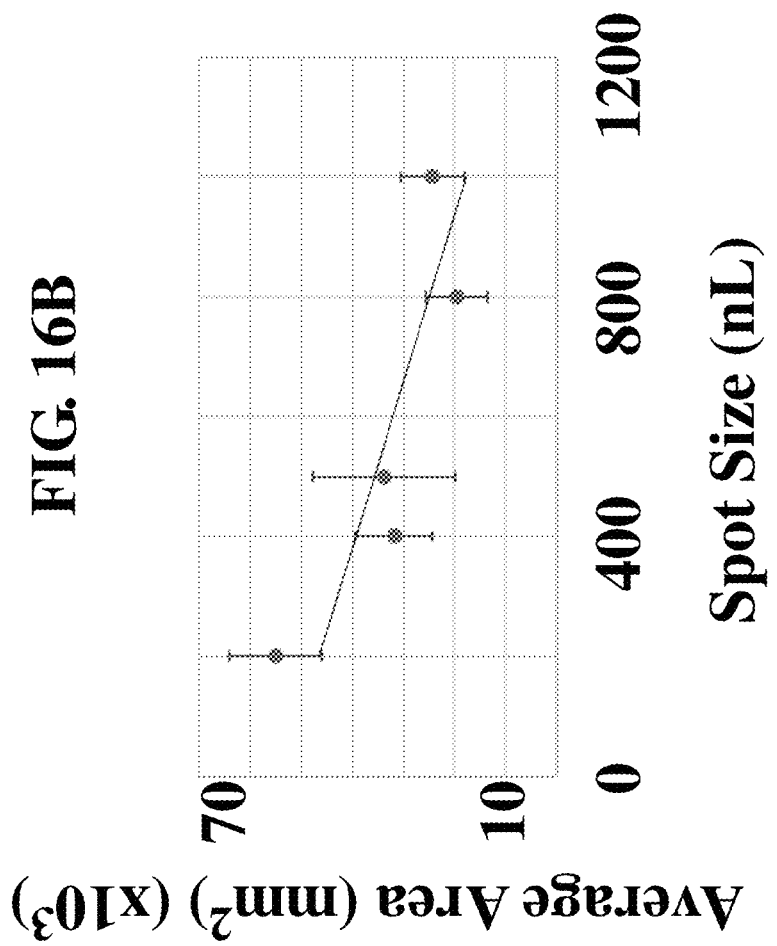
Figure 17A:
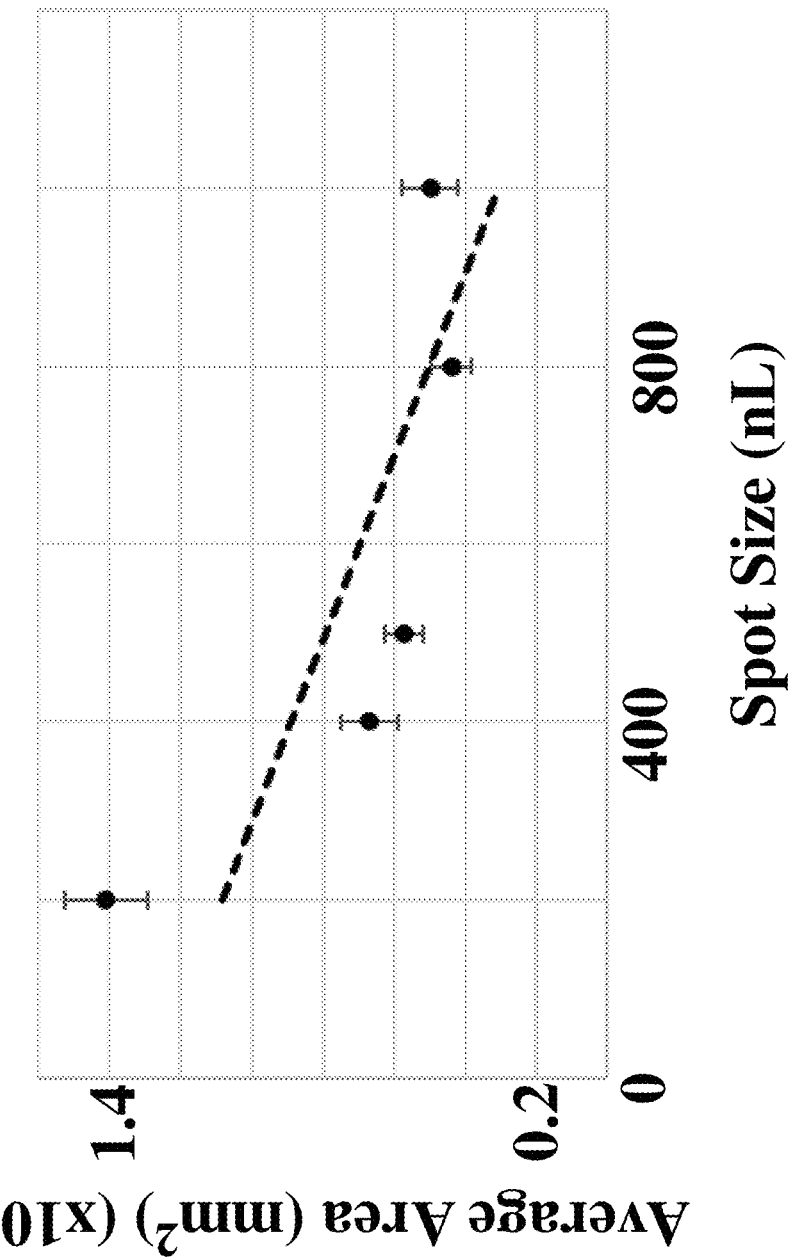
Figure 17B:
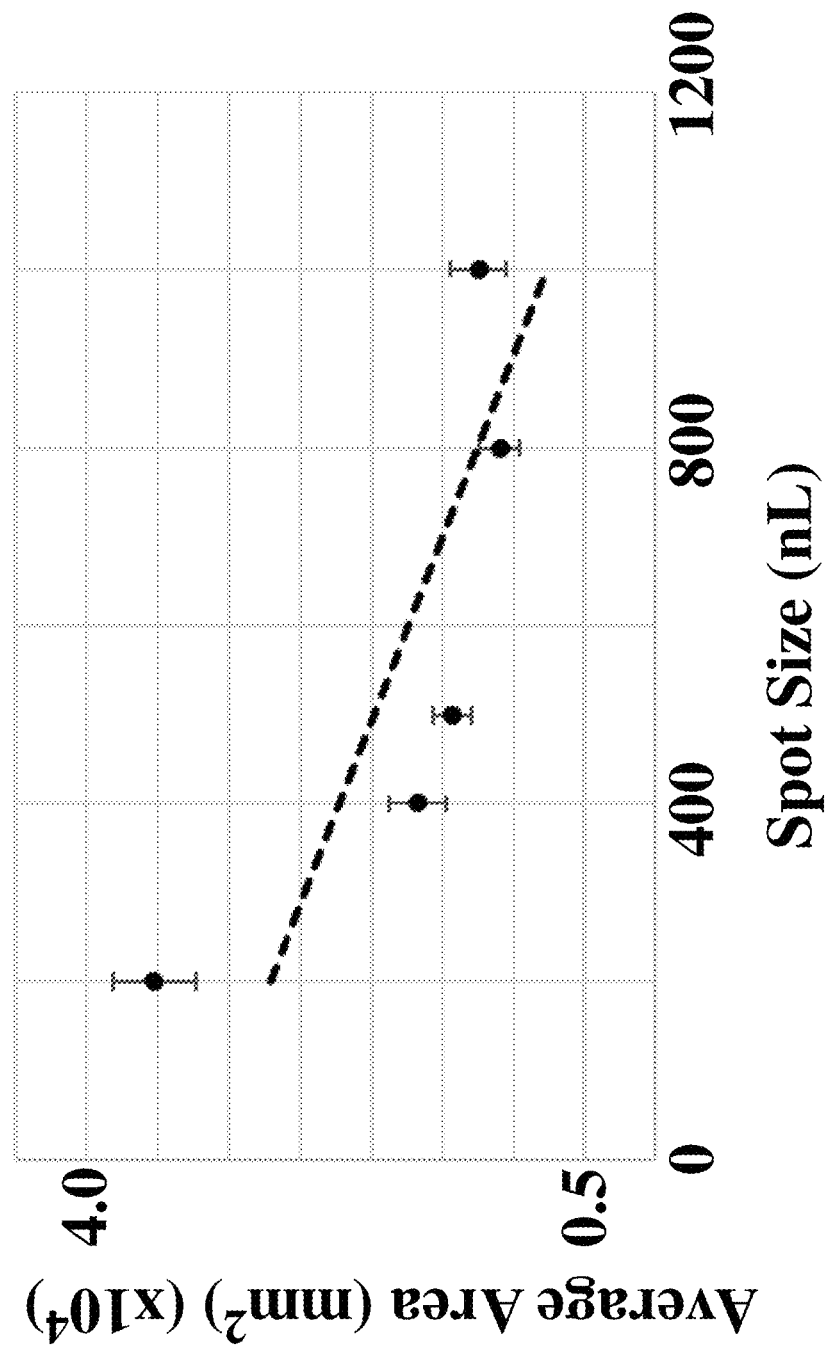
Figure 17C:
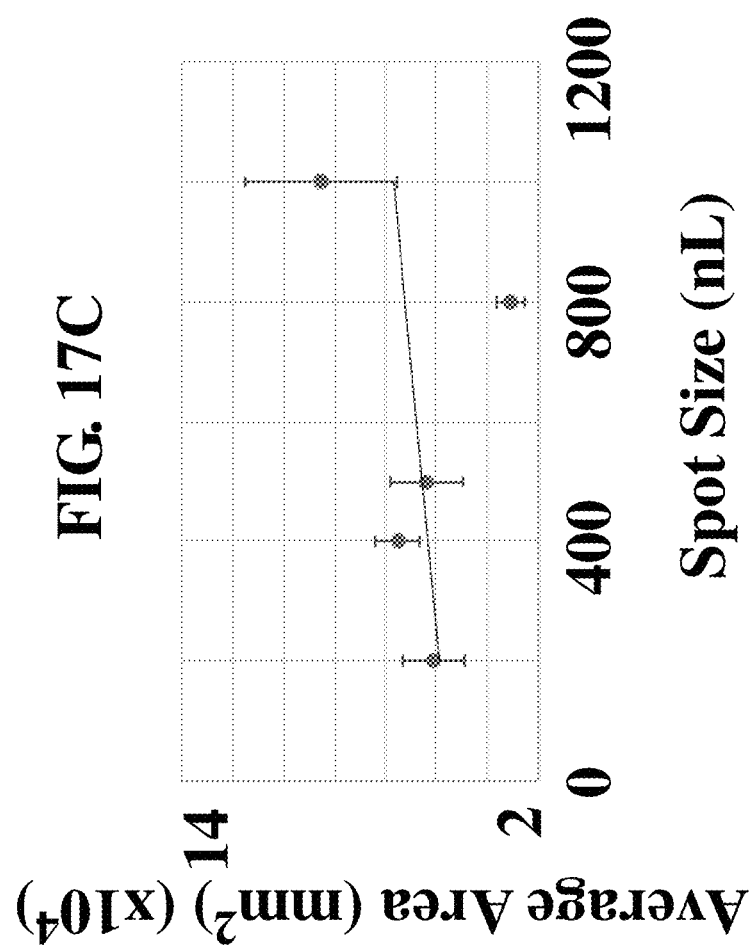
Figure 18B:
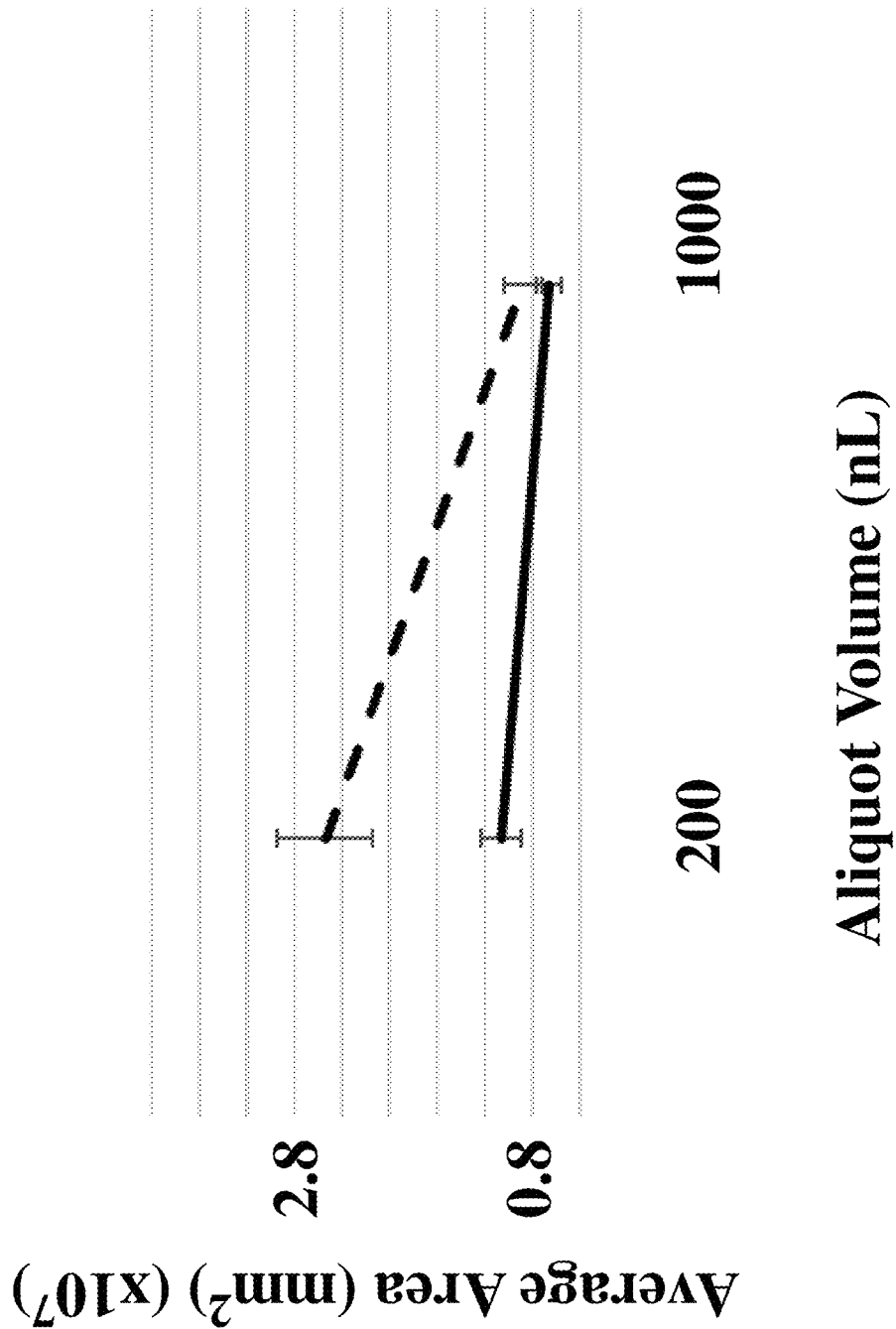

FIG. 11A is an EIC trace showing the intensity of the methadone (m/z 310) intact species generated in positive ionization mode with DART API of 200 nL samples of urine doped with methadone (1 pg/nL) and methadone-d$_3$ (0.5 pg/nL) in 80% deionized water spotted by a Mosquito onto a QuickStrip, according to an embodiment of the invention;

FIG. 11B is an EIC trace showing the intensity of the methadone-d$_3$ (m/z 313) intact species generated in positive ionization mode with DART API of 200 nL samples of urine doped with methadone (1 pg/nL) and methadone-d$_3$ (0.5 pg/nL) in 80% deionized water spotted by a Mosquito onto a QuickStrip, according to an embodiment of the invention;

FIG. 11C is a standard calibration curve plot showing the intensity of the methadone (m/z 310) intact ion species analyzed by a positive DART API versus concentration of methadone in 200 nL urine samples (urine samples were doped with varying concentrations of methadone and a constant concentration of methadone-d$_3$) spotted by a Mosquito onto a QuickStrip, according to an embodiment of the invention;

FIG. 11D is a positive DART API mass spectrum of a 200 nL urine sample containing a mixture of methadone (200 pg) and methadone-d$_3$ (50 pg) spotted by a Mosquito onto a QuickStrip, according to an embodiment of the invention;

FIG. 12A is an EIC trace showing the intensity of the cocaine (m/z 304) intact species generated in positive ionization mode with DART API of 200 nL urine sample doped with cocaine (1 ng/nL) in 50% methanol 50% deionized water spotted by a Mosquito onto a QuickStrip, according to an embodiment of the invention;

FIG. 12B is an EIC trace showing the intensity of the lidocaine (m/z 235) intact species generated in positive ionization mode with DART API of 200 nL urine sample doped with lidocaine (1 ng/nL) in 50% methanol 50% deionized water spotted by a Mosquito onto a QuickStrip, according to an embodiment of the invention;

FIG. 12C is an EIC trace showing the intensity of the caffeine (m/z 195) intact species generated in positive ionization mode with DART API of 200 nL urine sample doped with caffeine (1 ng/nL) in 50% methanol 50% deionized water spotted by a Mosquito onto a QuickStrip, according to an embodiment of the invention;

FIG. 12D is an EIC trace showing the intensity of the methadone (m/z 310) intact species generated in positive ionization mode with DART API of 200 nL urine sample doped with methadone (1 ng/nL) and methadone-d$_3$ (1 ng/nL) in 50% methanol 50% deionized water spotted by a Mosquito onto a QuickStrip, according to an embodiment of the invention;

FIG. 12E is a positive DART API mass spectrum of the 200 nL urine sample doped with a mixture of cocaine (1 ng/nL) in 50% methanol 50% deionized water spotted by a Mosquito onto a QuickStrip used to generate FIG. 12A, according to an embodiment of the invention;

FIG. 12F is a positive DART API mass spectrum of the 200 nL urine sample doped with a mixture of lidocaine (1 ng/nL) in 50% methanol 50% deionized water spotted by a Mosquito onto a QuickStrip used to generate FIG. 12B, according to an embodiment of the invention;

FIG. 12G is a positive DART API mass spectrum of the 200 nL urine sample doped with caffeine (1 ng/nL) in 50% methanol 50% deionized water spotted by a Mosquito onto a QuickStrip used to generate FIG. 12C, according to an embodiment of the invention;

FIG. 12H is a positive DART API mass spectrum of the 200 nL urine sample doped with methadone (1 ng/nL) and methadone-d3 in 50% methanol 50% deionized water spotted by a Mosquito onto a QuickStrip used to generate FIG. 12D, according to an embodiment of the invention;

FIG. 13A is a positive DART API mass spectrum of the 200 nL saliva sample doped with caffeine (50 ng/mL), lidocaine (50 ng/mL), cocaine (50 ng/mL), methadone (50 ng/mL) and methadone-d$_3$ (250 ng/mL) in 90% deionized water spotted by a Mosquito onto a QuickStrip, according to an embodiment of the invention;

FIG. 13B is a positive DART API mass spectrum of the 200 nL saliva sample doped with caffeine (100 ng/mL), lidocaine (100 ng/mL), cocaine (100 ng/mL), methadone (100 ng/mL) and methadone-d$_3$ (250 ng/mL) in 90% deionized water spotted by a Mosquito onto a QuickStrip, according to an embodiment of the invention;

FIG. 13C is a positive DART API mass spectrum of the 200 nL saliva sample doped with caffeine (250 ng/mL), lidocaine (250 ng/mL), cocaine (250 ng/mL), methadone (250 ng/mL) and methadone-d$_3$ (250 ng/mL) in 90% deionized water spotted by a Mosquito onto a QuickStrip, according to an embodiment of the invention;

FIG. 13D is a positive DART API mass spectrum of the 200 nL saliva sample doped with caffeine (500 ng/mL), lidocaine (500 ng/mL), cocaine (500 ng/mL), methadone (500 ng/mL) and methadone-d$_3$ (250 ng/mL) in 90% deionized water spotted by a Mosquito onto a QuickStrip, according to an embodiment of the invention;

FIG. 13E is a positive DART API mass spectrum of the 200 nL saliva sample doped with caffeine (1,000 ng/mL), lidocaine (1,000 ng/mL), cocaine (1,000 ng/mL), methadone (1,000 ng/mL) and methadone-d$_3$ (250 ng/mL) in 90% deionized water spotted by a Mosquito onto a QuickStrip, according to an embodiment of the invention;

FIG. 14A is an EIC trace showing the intensity of m/z 310 methadone intact species generated in positive ionization mode with DART API of 200 nL of a sample containing 2,000 ng/mL methadone and 1,000 ng/mL methadone-d3 in 100% DMSO spotted by a Mosquito on a QuickStrip, according to an embodiment of the invention;

FIG. 14B is an EIC trace showing the intensity of m/z 310 methadone intact species generated in positive ionization mode with DART API of 200 nL of a sample containing 10,000 ng/mL methadone and 5,000 ng/mL methadone-d3 in 100% DMSO spotted by a Mosquito on a QuickStrip, according to an embodiment of the invention;

FIG. 14C is an EIC trace showing the intensity of m/z 310 methadone intact species generated in positive ionization mode with DART API of 200 nL of a sample containing 20,000 ng/mL methadone and 10,000 ng/mL methadone-d3 in 100% DMSO spotted by a Mosquito on a QuickStrip, according to an embodiment of the invention;

FIG. 14D is an EIC trace showing the intensity of m/z 310 methadone intact species generated in positive ionization mode with DART API of 200 nL of a sample containing 40,000 ng/mL methadone and 20,000 ng/mL methadone-d3 in 100% DMSO spotted by a Mosquito on a QuickStrip, according to an embodiment of the invention;

FIG. 14E is an EIC trace showing the intensity of m/z 313 methadone-d3 intact species generated in positive ionization mode with DART API of 200 nL of a sample containing 2,000 ng/mL methadone and 1,000 ng/mL methadone-d3 in 100% DMSO spotted by a Mosquito on a QuickStrip, according to an embodiment of the invention;

FIG. 14F is an EIC trace showing the intensity of m/z 313 methadone-d3 intact species generated in positive ionization mode with DART API of 200 nL of a sample containing 10,000 ng/mL methadone and 5,000 ng/mL methadone-d3 in 100% DMSO spotted by a Mosquito on a QuickStrip, according to an embodiment of the invention;

FIG. 14G is an EIC trace showing the intensity of m/z 313 methadone-d3 intact species generated in positive ionization mode with DART API of 200 nL of a sample containing 20,000 ng/mL methadone and 10,000 ng/mL methadone-d3 in 100% DMSO spotted by a Mosquito on a QuickStrip, according to an embodiment of the invention;

FIG. 14H is an EIC trace showing the intensity of m/z 313 methadone-d3 intact species generated in positive ionization mode with DART API of 200 nL of a sample containing 40,000 ng/mL methadone and 20,000 ng/mL methadone-d3 in 100% DMSO spotted by a Mosquito on a QuickStrip, according to an embodiment of the invention;

FIG. 15A is a plot showing the relationship between the aliquot volume and intensity of the codeine ion species, when urine doped with codeine is spotted by a Mosquito on a QuickStrip, according to an embodiment of the invention;

FIG. 15B is a plot showing the relationship between the aliquot volume and intensity of the methadone ion species, when urine doped with methadone is spotted by a Mosquito on a QuickStrip, according to an embodiment of the invention;

FIG. 16A is a plot showing the relationship between the aliquot volume and area of the spot for heroin in synthetic urine spiked with heroin and codeine spotted by a Mosquito on a QuickStrip, according to an embodiment of the invention;

FIG. 16B is a plot showing the relationship between the aliquot volume and area of the spot for codeine in synthetic urine spiked with heroin and codeine spotted by a Mosquito on a QuickStrip, according to an embodiment of the invention;

FIG. 17A is a plot showing the relationship between the aliquot volume and area of the spot for heroin in synthetic urine spiked with heroin, codeine and methamphetamine spotted by a Mosquito on a QuickStrip, according to an embodiment of the invention;

FIG. 17B is a plot showing the relationship between the aliquot volume and area of the spot for codeine in synthetic urine spiked with heroin, codeine and methamphetamine spotted by a Mosquito on a QuickStrip, according to an embodiment of the invention;

FIG. 17C is a plot showing the relationship between the aliquot volume and area of the spot for methamphetamine in synthetic urine spiked with heroin, codeine and methamphetamine spotted by a Mosquito on a QuickStrip, according to an embodiment of the invention;

FIG. 18A is a plot showing the relationship between the aliquot volume and intensity of the codeine ion species, when urine doped with codeine is spotted by a Mosquito on a QuickStrip is analyzed at (–) 1 mm/s or ( - - - ) 3 mm/s, according to an embodiment of the invention;

FIG. 18B is a plot showing the relationship between the aliquot volume and intensity of the methadone ion species, when urine doped with methadone is spotted by a Mosquito on a QuickStrip is analyzed at (–) 1 mm/s or ( - - - ) 3 mm/s, according to an embodiment of the invention;

DETAILED DESCRIPTION OF THE INVENTION

Abbreviations include:
AISM=atmospheric ionization sorbent material; API=atmospheric pressure ionization; AS=analyte species; DART=direct analysis real time; DESI=desorption electrospray ionization; DMS=differential mobility spectrometer; ESI=electrospray ionization; GIS=gas ion separator; IMS=ion mobility spectrometer; MS=mass spectrometry; RS=reactive species.

Definitions of certain terms that are used hereinafter include:

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term Gas-Ion Separator (GIS) will be used to refer to a device which separates ions from one or both neutral molecules and neutral atoms allowing the pre-concentration and transfer of the ions to an analysis system. The term 'inlet tube' will be used to refer to the low vacuum side of a GIS. The term 'outlet tube' will be used to refer to the high vacuum side of the GIS. In various embodiments of the invention, the contained tube can be an inlet tube. Active ionization refers to the process where an atmospheric analyzer not utilizing a radioactive nucleus can be used to ionize analyte ions. A capacitive surface is a surface capable of being charged with a potential. A surface is capable of being charged with a potential, if a potential applied to the surface remains for the typical duration time of an experiment, where the potential at the surface is greater than 50% of the potential applied to the surface. A vacuum of atmospheric pressure is approximately 760 torr. Here, 'approximately' encompasses a range of pressures from below $10^1$ atmosphere=$7.6 \times 10^3$ torr to $10^{-1}$ atmosphere=$7.6 \times 10^1$ torr. A vacuum of below $10^{-3}$ torr would constitute a high vacuum. Here, 'approximately' encompasses a range of pressures from below $5 \times 10^{-3}$ torr to $5 \times 10^{-6}$ torr. A vacuum of below $10^{-6}$ torr would constitute a very high vacuum. Here, 'approximately' encompasses a range of pressures from below $5 \times 10^{-6}$ torr to $5 \times 10^{-9}$ torr. In the following, the phrase 'high vacuum' encompasses high vacuum and very high vacuum.

The word 'contact' is used to refer to any process by which molecules of a sample in one or more of the gas, liquid and solid phases becomes adsorbed, absorbed or chemically bound to a surface.

A grid becomes 'coated' with a substrate when a process results in substrate molecules becoming adsorbed, absorbed or chemically bound to a surface. A grid can be coated when beads are adsorbed, absorbed or chemically bound to the grid. A grid can be coated when nano-beads are adsorbed, absorbed or chemically bound to the grid.

A filament means one or more of a loop of wire, a segment of wire, a metal ribbon, a metal strand or an un-insulated wire, animal string, paper, perforated paper, fiber, cloth, silica, fused silica, plastic, plastic foam, polymer, Teflon, polymer impregnated Teflon, cellulose and hydrophobic support material coated and impregnated filaments. In various embodiments of the invention, a filament has a diameter of approximately 50 microns to approximately 2 mm. In measuring the diameter of a filament, approximately indicates plus or minus twenty (20) percent. In an embodiment of the invention, the length of the filament is approximately 1 mm to approximately 25 mm. In measuring the length of a filament, approximately indicates plus or minus twenty (20) percent.

The term 'orientation' means the position of a mesh with respect to another section if mesh or with respect to a grid or a sample holder. In an embodiment of the invention, the mesh, the grid, or the sample holder can be mounted on an X-Y translation stage to enable precise orientation of the samples spotted on the mesh relative to the ionizing species. The controlling electronics and the stepper motor drivers, for the X-Y stages, can be mounted directly onto a box housing the X-Y translation stage, while the microcontroller that controls the orientation can be separately mounted.

The term 'proximity' means the position of a mesh or an area on the mesh with respect to another mesh or other area on the mesh.

The term 'registration' means when an area of a mesh (e.g., the proximal area) lines up with the mesh to deliver the heat from the mesh to the proximal area of the tine.

The term 'contacting' means the coming together or touching of objects or surfaces such as the sampling of a surface with an area of a mesh.

The shape of a mesh can be a cylinder, an elliptical cylinder, a long square block, a long rectangular block or a long thin surface.

The term 'hole' refers to a hollow space in an otherwise solid object, with an opening allowing light and/or particles to pass through the otherwise solid object. A hole can be circular, ellipsoid, pear shaped, a slit, or polygonal (including triangular, square, rectangular, pentagonal, hexagonal, heptagonal, and the like).

A first sorbent material is adapted to collect a first sample molecule when the first sorbent material is chemically attractive to a chemical characteristic of the first sample molecule. For example a long chain (C18) aliphatic species present in the sorbent material will be attractive to bind hydrophobic molecules in the presence of a non-hydrophobic phase. In contrast, a short chain (C4) aliphatic species present in the sorbent material will be attractive to bind less hydrophobic molecules in the presence of a non-hydrophobic phase.

A metal comprises one or more elements consisting of lithium, beryllium, boron, carbon, nitrogen, oxygen, sodium, magnesium, aluminum, silicon, phosphorous, sulfur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium. Thus a metal includes for example, a nickel titanium alloy known as nitinol or a chromium iron alloy used to make stainless steel.

A plastic comprises one or more of polystyrene, high impact polystyrene, polypropylene, polycarbonate, low density polyethylene, high density polyethylene, polypropylene, acrylonitrile butadiene styrene, polyphenyl ether alloyed with high impact polystyrene, expanded polystyrene, polyphenylene ether and polystyrene impregnated with pentane, a blend of polyphenylene ether and polystyrene impregnated with pentane or polyethylene and polypropylene.

A polymer comprises a material synthesized from one or more reagents selected from the group comprising of styrene, propylene, carbonate, ethylene, acrylonitrile, butadiene, vinyl chloride, vinyl fluoride, ethylene terephthalate, terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylamine diamine (hexane-1,6-diamine), pentamethylene diamine, methylethanolamine, trimethylamine, aziridine, piperidine, N-methylpiperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and or a blend of two or more materials synthesized from the polymerization of these reagents.

A plastic foam is a polymer or plastic in which a gaseous bubble is trapped including polyurethane, expanded polystyrene, phenolic foam, XPS foam and quantum foam.

A 'mesh' means one or more of two or more connected filaments, two or more connected strings, foam, a grid, perforated paper, screens, paper screens, plastic screens, fiber screens, cloth screens, polymer screens, silica screens, TEFLON® (polytetrafluoroethylene (PVDF)) screens, polymer impregnated Teflon screens, and cellulose screens. In various embodiments of the invention, a mesh includes one or more of three or more connected filaments, three or more connected strings, mesh, foam, a grid, perforated paper, screens, plastic screens, fiber screens, cloth, and polymer screens. In an embodiment of the invention, a mesh can have approximately 10 filaments per mm. In another embodiment of the invention, a mesh can have approximately 20 filaments per mm. In an additional embodiment of the invention, a mesh can have approximately 30 filaments per mm. In an alternative embodiment of the invention, a mesh can have approximately 100 filaments per mm. In designing the number of filaments per mm, approximately indicates plus or minus twenty (20) percent.

A 'substratum' is a polymer, a metal, and or a plastic.

A 'grid' is a substratum in which either gaps, spaces or holes have been punched or otherwise introduced into the substratum or in which a window or section has been cut out or otherwise removed from the substratum and a mesh has been inserted into the removed window or section. In an embodiment of the invention, the grid can have a thickness between a lower limit of approximately 1 micron and an upper limit of approximately 1 cm. In this range, approximately means plus or minus twenty (20) percent.

The phrase a 'biological matrix' means a biological fluid (e.g., urine, milk, semen, and saliva), a biological liquid (e.g., blood, lymph, synovial fluid and the like), a part thereof (e.g. serum) or a biological tissue (e.g. muscle, epithelial, bone, nerve, cartilage and the like).

The phrase a 'matrix molecule' means a species derived from a biological matrix.

The phrase a 'molecule of interest' or 'analyte' means any naturally occurring species (e.g., caffeine, cocaine, tetra hydro cannabinol), or synthetic molecules that have been introduced to the biological system e.g., pharmaceutical drugs (e.g., lidocaine, methadone, sildenafil, Lipitor, enalapril and derivatives thereof), and recreational drugs (e.g., morphine, heroin, methamphetamine, and the like and derivatives thereof).

The phase 'introduced contaminant' means a chemical that becomes associated with a sample during sample preparation and/or sample analysis. An introduced contaminant can be airborne or present in or on surfaces that the sample is in contact. For example, perfumes and deodorants can be associated with and analyzed during sample analysis. Alternatively, phthalates present in plastic tubes used to handle samples can leach out of the plastic tube into the sample and thereby be introduced into the sample.

The phrase 'background chemical' means a 'matrix molecule' and/or an 'introduced contaminant'.

The phrase an 'ion suppressor molecule' means a background chemical which suppresses ionization of a molecule of interest and/or generates a background ion which ionizes to the detriment of detection of a molecule of interest.

The phrase 'background ion' refers to an ion formed from a background chemical. The background ion can include the molecule itself, an adduct of the molecule, a fragment of the molecule or combinations thereof.

The phrase 'matrix effect' refers to the reduction in ionization of a molecule of interest due to the presence of a background ion. A matrix effect is caused when a background chemical suppresses ionization of a molecule of interest and/or a background ion ionizes to the detriment of a molecule of interest. Without wishing to be bound by theory, in the former case it is believed that the molecule of interest is not ionized by the presence of the background chemical. In the latter case, the resulting mass spectrum is dominated by a background ion to the detriment of the analysis of the molecule of interest. The background ion can be suppressing and/or masking the ionization of a molecule of interest.

The phrase 'analysis volume' refers to the aliquot of sample that is analyzed, for example applied to a mesh for analysis.

The phrase an 'ion intensifier' means a chemical that inhibits the matrix effect.

DART

DART is another API method suitable for the analysis of analytes. Various embodiments of DART API are described in U.S. Pat. No. 7,112,785 to Laramee (hereinafter referred to as the '785 patent) which is herein expressly incorporated by reference in its entirety and for all purposes. The '785 patent is directed to desorption ionization of molecules from surfaces, liquids and vapor using a carrier gas containing reactive species (RS). The DART API can use a large volume of carrier gas, e.g., helium is suitable although other inert gases that can generate RS can be used.

Nitrogen DART

An API can ionize analyte molecules without the use of solvents to dissolve the analyte. The ionization occurs directly from solids and liquids. Molecules present in the gas phase can also be ionized by the reactive species exiting the API. In an embodiment of the invention, the reactive species utilized can be excited nitrogen atoms or molecules. In an embodiment of the invention, the reactive species can produce long lived metastable species to impact the analyte molecules at atmospheric pressure and, e.g., to affect ionization.

The recent commercialization of a DART API with increased capability for functioning with naturally abundant nitrogen as the metastable carrier gas is a significant advance. This can enable the utilization of the DART API in more diverse climates, and with minimal requirement for compressed gases or any liquids commonly used with alternative atmospheric ionization systems. In an embodiment of the invention, processing of ambient air to remove the oxygen can be accomplished by placing a tube containing an oxygen scavenger in the path of gas flow from the air to the inlet of the DART API. An oxygen absorbent (see U.S. Pat. No. 4,127,503 to Yoshikawa et al., which is incorporated by reference in its entirety and for all purposes) such as a mixture of finely divided moist $Fe_2O_3$ and KCl can be used to reduce the level of oxygen present in an air stream. In an alternative embodiment of the invention, a process for separating air by cryogenic distillation (U.S. Pat. No. 7,219,514 to Gamier et al., which is incorporated by reference in its entirety and for all purposes) using an apparatus comprising a medium-pressure column and a low-pressure column that are thermally coupled, where a quantity of compressed and purified air is cooled in an exchange line down to a cryogenic temperature and is sent at least partly to the medium-pressure column, and a nitrogen-enriched stream is sent from the medium-pressure column to the low-pressure column and the nitrogen-enriched stream can be withdrawn from the low-pressure column. In another embodiment of the invention, an oxygen absorbent can be used in combination with cryogenic distillation to further reduce the level of oxygen present in the nitrogen-enriched stream or more efficiently reduce the level of oxygen. An API therefore can be an ideal device for sampling of confined spaces into which introduction of solvents to mix with analytes might create an unstable chemical condition.

Gas-Ion Separator (GIS)

In various embodiments of the invention, devices and methods for transferring analyte ions desorbed from the sorbent surface using an atmospheric analyzer into the inlet of a mass spectrometer can utilize a Gas-Ion Separator (GIS). Embodiments of this invention include devices and methods for collecting and transferring analyte ions and/or other analyte species formed within a carrier to the inlet of a mass spectrometer.

In an embodiment of the invention, one or both the inlet and the outlet GIS tubing can be made of one or more materials selected from the group consisting of stainless steel, non-magnetic stainless steel, steel, titanium, metal, flexible metal, ceramic, silica glass, plastic and flexible plastic. In an embodiment of the invention, the GIS tubing can range in length from 10 millimeters to 10 meters. In an embodiment of the invention, the GIS tubing can be made of non-woven materials. In an embodiment of the invention, the GIS tubing can be made from one or more woven materials.

In various embodiments of the invention, a GIS comprising two or more co-axial tubes with a gap between the tubes and a vacuum applied in the gap region is used to allow large volumes of carrier gas to be sampled. In various embodiments of the invention, a GIS is made up of an inlet tube and an outlet tube. In an embodiment of the invention, the proximal end of the inlet tube is closest to the sorbent surface and the distal end of the inlet tube can be some distance away from the proximal end where a vacuum can be applied. In various embodiments of the invention, the proximal end of the outlet tube is adjacent the distal end of the inlet tube and the distal end of the outlet tube enters the spectroscopy system.

Ninety Degree GIS

Relying upon the commercial high speed X-Y plate moving components available and the imbedded software for X-Y control it is possible to enable precise orientation of QuickStrip mesh samples to allow accurate deposition of samples for DART API analysis of those samples. Previously the QuickStrip mesh was transferred to a cassette carrier which had been connected to a limited performance robotic arm to facilitate rapid positioning of samples in front of the DART ionization source that permitted positioning of the mesh in an X-Z configuration relative to the source and the API inlet of the mass detector. The X-Z positioner proved suitable for larger volume samples of 2000-5000 nL in volume. However with the use of robotic sample depositions, allows systems to deposit sub-microliter volumes of sample onto the mesh. In these situations, the positioner was not sufficiently accurate to reliably orient each of the successive samples in a row or column with respect to the DART ionizer. To address the deficiencies of the low performance robotics, a prototype Ninety Degree GIS component has been designed. The Ninety Degree GIS allows direct DART API analysis from higher performance robotics without the requirement for moving the sample from the sample deposition robot. The Ninety Degree GIS can be combined with an extended X-Y plate with a holder that allows movement of the samples deposited onto the Quick-Strip mesh through the desorption ionization region located at the distal end of the DART source such that the sample deposited onto the front side of the mesh can be vaporized and ionized in close proximity to the proximal end of the GIS positioned at the back side of the mesh. Rapid and reproducible desorption is facilitated even for ultralow volume samples where the samples transit the ionizing region under the control of the more accurate robotic system used to deposit the sample onto the mesh with great positional accuracy. Accordingly, the extended X-Y plate holder enables the combination of DART direct ionizing species at the front side of the plate. The Ninety Degree GIS is used to transfer the ionized species formed into the API region of the mass detector using a tube or flexible tube with an approximately ninety (90) degree turn. The Ninety Degree GIS eliminates the step of manually repositioning the QuickStrip mesh post-sample deposition. In various embodiments of the invention, the Ninety Degree GIS component can transfer ions with an angle range of approximately eighty (80) to one hundred (100) degrees, where approximately means plus or minus ten (10) degrees.

Front Facing DART

By positioning the DART API source at an angle of approximately thirty (30)-sixty (60) degrees to the face of the X-Y plate after sample preparation, it is possible to ionize the sample and extract the analyte ions in a standard mass spectrometer (or optionally through a standard GIS). In this range approximately means or means ten (10) degrees. Relying upon the commercial high speed X-Y plate moving components available and the imbedded software for X-Y control it is possible to enable precise orientation of QuickStrip mesh samples to allow DART API analysis of the samples.

Spot Size

Depending on the distance between the source of the ionizing species and the mesh the spot size of the ionizing species impacted the mesh will vary. A cap with a cap hole through which the ionizing species emanates can be used to restrict the spot size at the mesh. The dimensions of the cap and the cap hole can be chosen to adjust the spot size of the ionizing species at the mesh. The cap can extend a distance (117) between a lower limit of approximately 0.1 mm and an upper limit of approximately 20.0 mm (e.g. 0.2, 0.3, 0.4, and the like up to 19.5, 19.6, 19.7, 19.8, 19.9 mm), where approximately in this range means plus or minus twenty (20) percent. In various embodiments of the invention, the distance (117) can be continuously adjustable to optimize scan speed depending on a number of factors including for example the number of samples to be analyzed. The cap hole (119) can have a variety of shapes, including ovoid, elliptical, rectangular, square and circular. A circular cap hole (119) can have a diameter between a lower limit of approximately 0.1 mm and an upper limit of approximately 10.0 mm (e.g. 0.2, 0.3, 0.4, and the like up to 9.5, 9.6, 9.7, 9.8, 9.9 mm), where approximately in this range means plus or minus twenty (20) percent. For non-circular shaped cap holes (119) the largest extent of the opening in the cap hole can be between a lower limit of approximately 0.1 mm and an upper limit of approximately 10.0 mm (e.g. 0.2, 0.3, 0.4, and the like up to 9.5, 9.6, 9.7, 9.8, 9.9 mm), where approximately in this range means plus or minus twenty (20) percent. In various embodiments of the invention, the cap hole (119) can be continuously adjustable to optimize spot size and spatial resolution, thereby allowing selection of appropriate scan speeds without contamination or artefacts.

Figure 2:
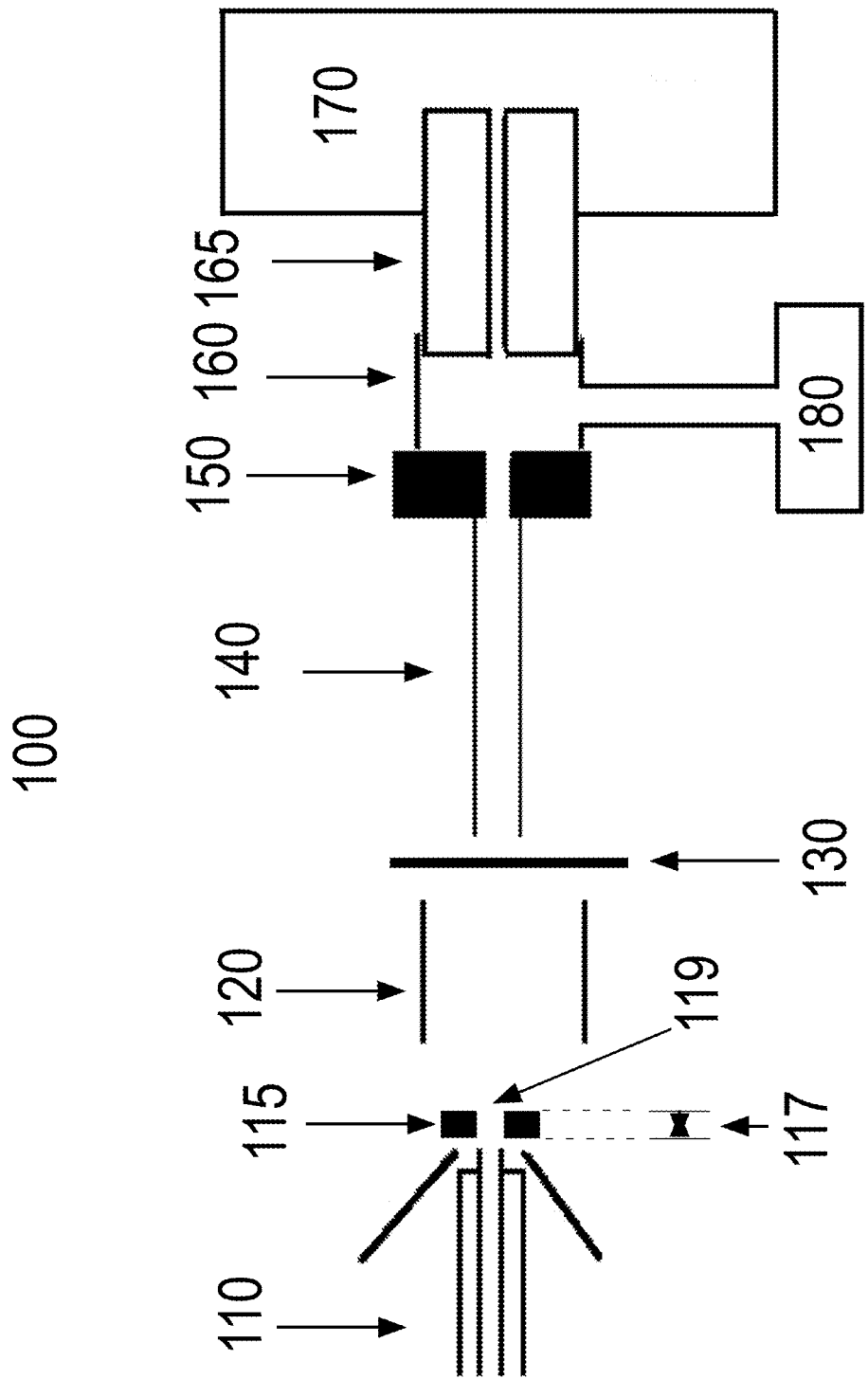
FIG. 2 is a schematic diagram of a sample applied to a mesh or grid inserted into the ionizing volume of the spectrometer.

In an embodiment of the present invention, as shown in FIG. 2, the distance between the distal end of the DART source with a 0.5 mm cap (115), to the mesh (130) (where the filaments making up the mesh were spaced 74/inch or 0.34 mm apart) was approximately 1.5 mm. In this configuration, it was possible to analyze spots that were 2.25 mm apart (i.e., from an adjacent sample) without any observation of species from the adjacent sample (i.e., without any cross contamination). Accordingly, in an embodiment of the present invention, the spatial resolution is approximately 1 mm. The cap (115) extends approximately 2.0 mm (117), where the cap hole (119) is approximately 0.5 mm in diameter. In this range, approximately means plus or minus twenty (20) percent.

API

The process of API involves the initial action of ionizing a gas by an electrical discharge. In plasma-based API, the electrical discharge of inert gases such as nitrogen, argon and helium lead to the formation of ionized gas molecules, atoms, and metastable molecules and atoms. These charged and energetic particles exit the ionization source where they interact with the molecules in air including background chemicals. Ions are formed during that interaction. Those ions are usually (i) intact protonated or deprotonated molecules such as $NO^+$, $O_2^-$, $H_3O^+$, (ii) clusters of water molecules with one proton, and (iii) ions derived from the molecules present in the ambient air including background chemicals. API becomes an analytical tool when those protonated water molecules interact with analytes present in the air resulting in transfer of the proton to the analyte. The analyte can enter the ionizing gas by introduction of the analyte as a gas, liquid or solid, positioned in the path of the products of the electrical discharge of the gas. Two forms of API are Atmospheric Pressure Chemical Ionization (APCI) using an electrical discharge between a high voltage needle and a surface to which the sample has been applied, and Direct Analysis in Real Time (DART) using an electrical discharge and heated gas which desorbs the sample from a surface into the atmosphere. In absence of a sample, the molecules present in the ambient air become ionized and when detected generate a mass spectrum.

In many cases the purposeful introduction of a sample into the ionizing gas results in formation of an ion that is easily measured by using a spectrometer positioned in close proximity to the site of the API.

In the case of biological samples certain molecules present possess very high proton affinity meaning that their purposeful introduction into the ionizing gas results in their ionization and formation of ionized dimers containing two of the molecules and a proton. High proton affinity molecule can also combine with another molecule or some closely related molecule forming a mixed dimer or tetramer in the protonated form. The affinity for these molecules for protons prohibits the use of the ionizing method as an analytical method since other molecule of interest in the sample cannot remain un-ionized and are thus not detected using a spectrometer positioned in close proximity to the site of the API. In the API experiments the domination of the resulting spectra by one molecule or collection of high proton affinity molecules is commonly identified as an experiment where the matrix effect is present.

In theory, during ambient ionization the analyte or molecule of interest may not be detected when the sample being analyzed contains background ions that ionize more efficiently than the analyte. The detection of the molecule of interest is compromised as the character of the background chemicals becomes more competitive. Without wishing to be bound by theory, it is believed that as the affinity of the background chemical for the ionizing gas increases, the detection of the molecule of interest becomes compromised decreasing the efficiency of detection of the molecule of interest. This is a manifestation of the 'matrix effect', a condition in API that can prevent use of the method for analysis. There are a number of background chemicals that cause matrix effects in specific circumstances. For example, the presence of urea in urine and nicotinamide in tobacco products are examples where the background chemicals dominate the spectra produced to the point where they prohibit reliable detection of other chemicals in the sample.

In an embodiment of the invention, reducing the analysis volume can be used to reduce the ambient ionization background and thereby improve the detection and quantitation of molecules of interest in samples. That is, while background chemicals often prohibit detection of the molecules of interest, the matrix effect can be observed to be reduced by reducing the analysis volume.

A matrix effect generally often needs to be eliminated in order for an experiment to be successful. In an embodiment of the invention reduction of the matrix effect is enabled by reducing the sample volume. Without wishing to be bound by theory, it is believed that reducing the sample volume results in a smaller area available for vaporization into the gas phase where ionization occurs. In an alternative embodiment of the invention reduction of the matrix effect is enabled by addition of an ion intensifier reagent. Without wishing to be bound by theory, it is believed that the ion intensifier neutralizes the matrix molecules present in the biological matrix prior to the analysis.

Figure 3A:
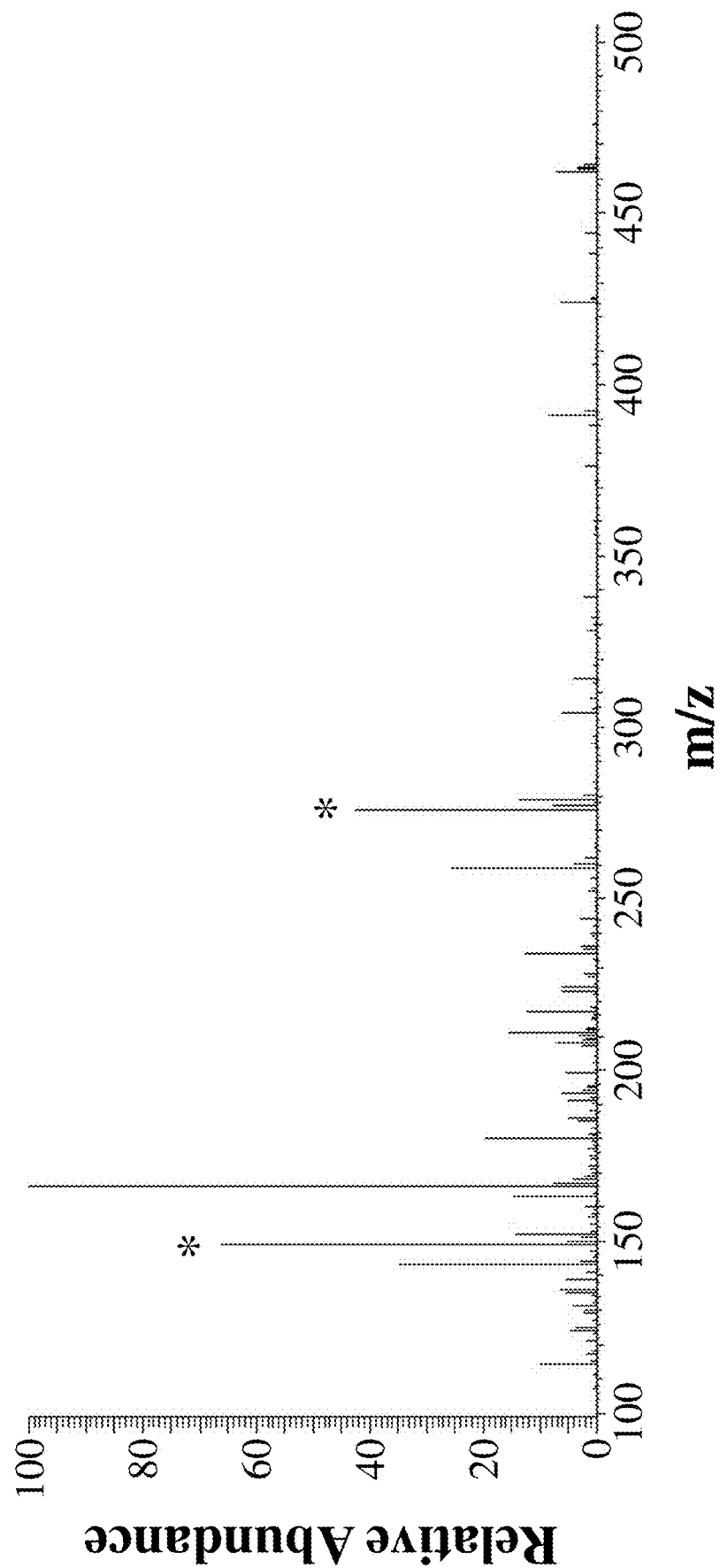
FIG. 3A is a positive DART API mass spectrum (100-500 Da) of a mesh in air without a sample present on the mesh.
Figure 3B:
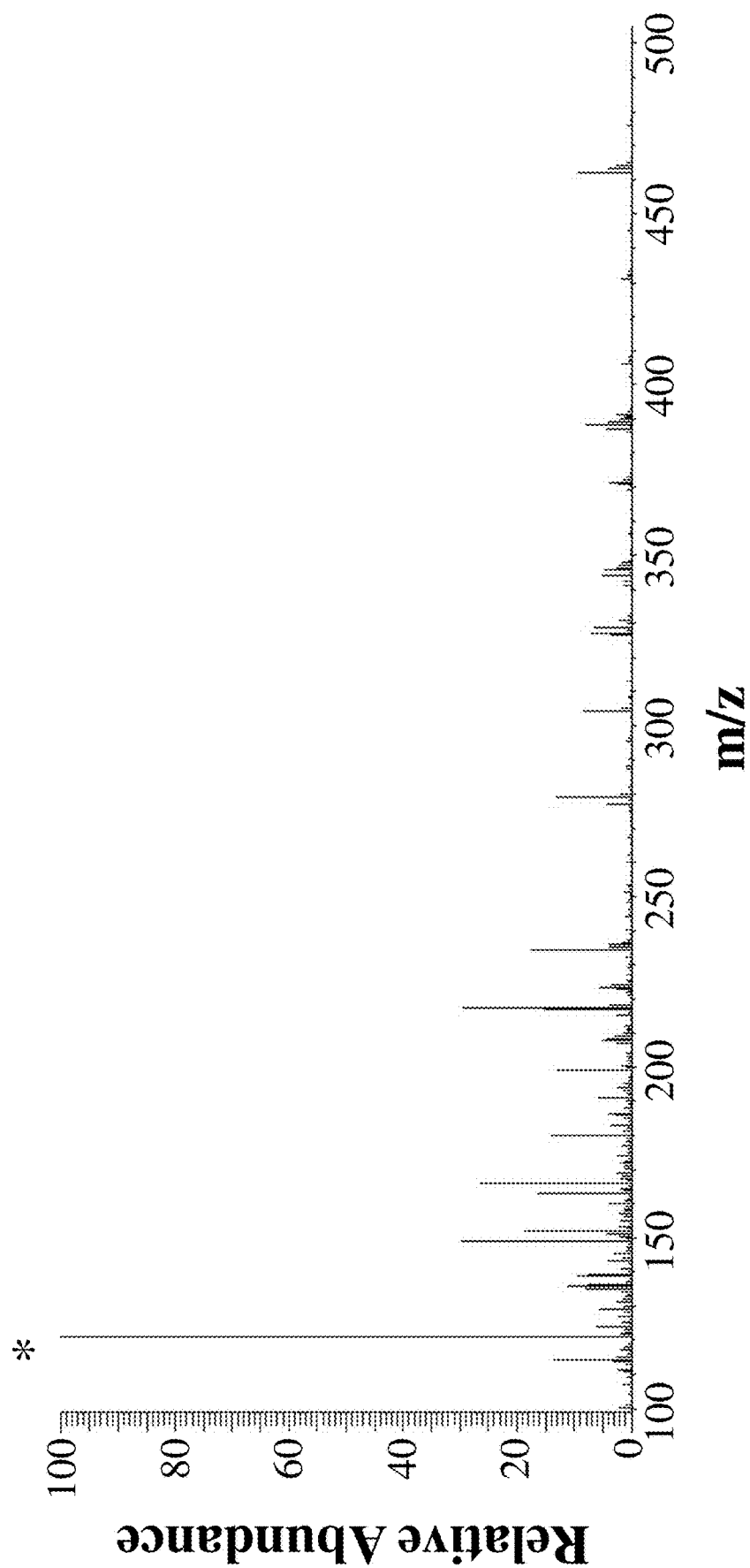
FIG. 3B is a positive DART API mass spectrum (100-500 Da) of a mesh with a volume of urine applied.
Figure 3C:
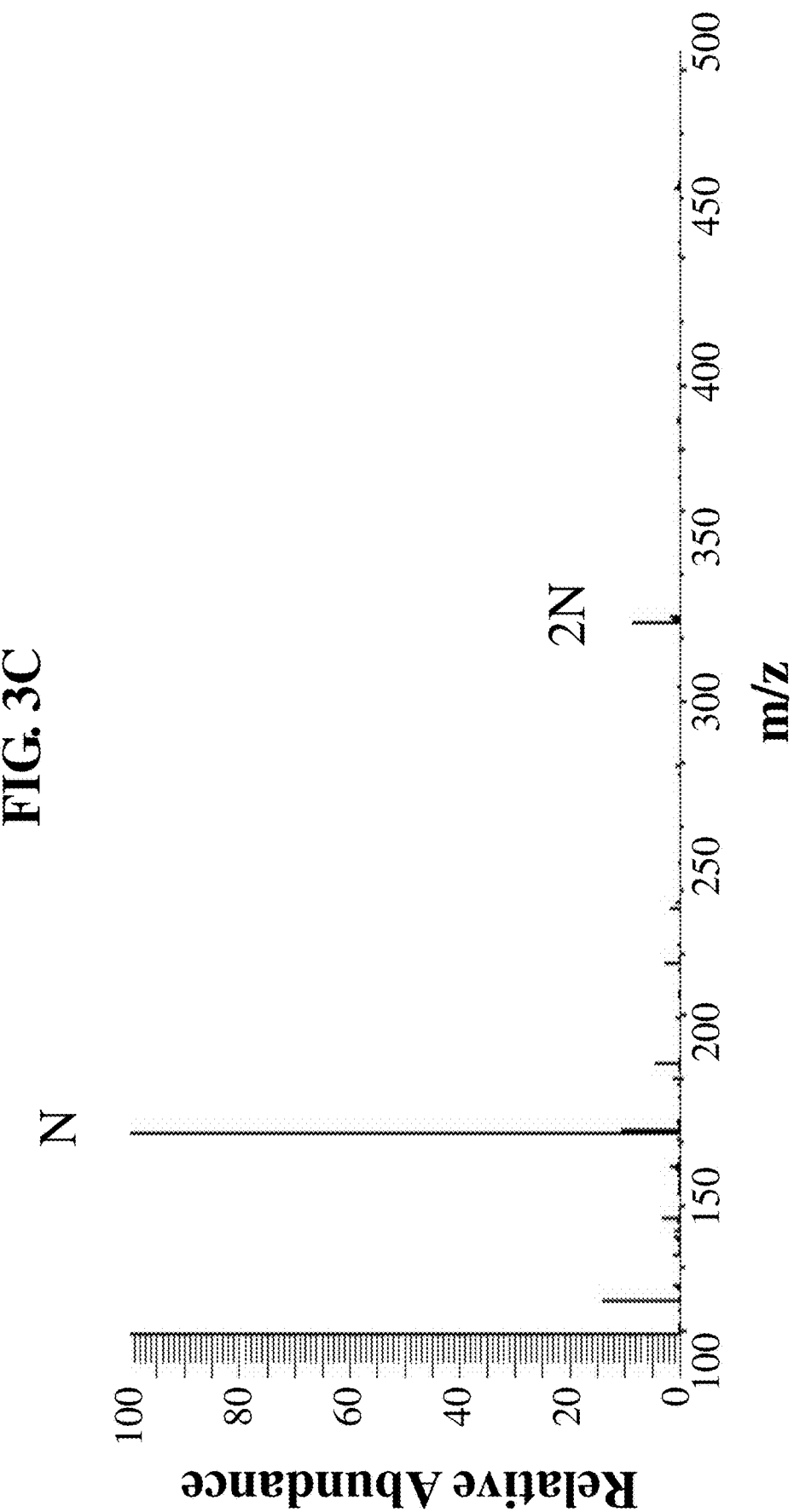
FIG. 3C is a positive DART API mass spectrum (100-500 Da) of a mesh with no sample present on the mesh in an e-cigarette vapor.

FIG. 2 shows an API source (110) where the ionizing gas exits the distal end of the source through a cap (115) and interacts with molecules present in the ambient atmosphere which result in the production of ions. The ions and neutral gases are drawn from the ionizing region (120) surrounding the sample applied to a surface (130) to the spectrometer (170) by the action of a vacuum applied to the proximal end of a transfer tube (140) to which a vacuum has been applied at the distal end (150), either by the spectrometer (170) or an external vacuum pump (180). In an embodiment of the invention, the gas containing ions enter a gas ion separator at its proximal end of the transfer tube (140) and travel towards the entrance of the entrance region (160) containing the spectrometer inlet tube (165) and there drawn into the spectrometer (170) by either the vacuum of the spectrometer (170) or a combination of that vacuum and the vacuum of an external pump (180). The volume of gas containing ions passing through the spectrometer inlet tube (165) into the volume of the spectrometer (170) can be analyzed to permit detection and characterization of the ions. The mass spectrum generated from a mesh with no sample applied to the mesh in an air atmosphere is shown in FIG. 3A. The spectrum is dominated by ions generated from low mass molecules present in the atmosphere and persistent organic molecules from the production of plastics and other chemicals, where ions are present at m/z 149.12 (marked with asterisk), 166.14, 259.19 and 276.22 (marked with asterisk). In an experimental test, introduction of a sample involves either directing a gas of interest, or positioning of a sample of interest on a surface (130) which is then positioned in the ionization region (120) between the source (110) and spectrometer (170) and which typically results in an immediate change in the appearance of the spectra as shown in FIG. 3B which shows the ambient ionization mass spectrum of a sample of urine. The interaction of ionizing gas with molecules from the urine sample results in the sample related molecules being protonated making them suitable for detection while the molecules originally present in air that had been detected in the absence of the sample are no longer are the predominant species. The most abundant ion detected is the protonated urea-dimer, at m/z 121.07 (marked with asterisk). Other ions observed are at m/z 149.12, 166.14, 180.16, 217.18, 234.21, 279.16, and 462.15). FIG. 3C shows the ambient ionization mass spectrum of a mesh (130) with no sample applied to the mesh (130) in an e-cigarette atmosphere. The dominant ions observed are attributed to nicotinamide at m/z 163.12 (marked with an 'N') and 325.24 (marked with '2N'). Few other ions are detected due to the matrix effects, due to the effect of the nicotinamide which is readily ionized.

Reduction in Sample Volume

Figure 4A:
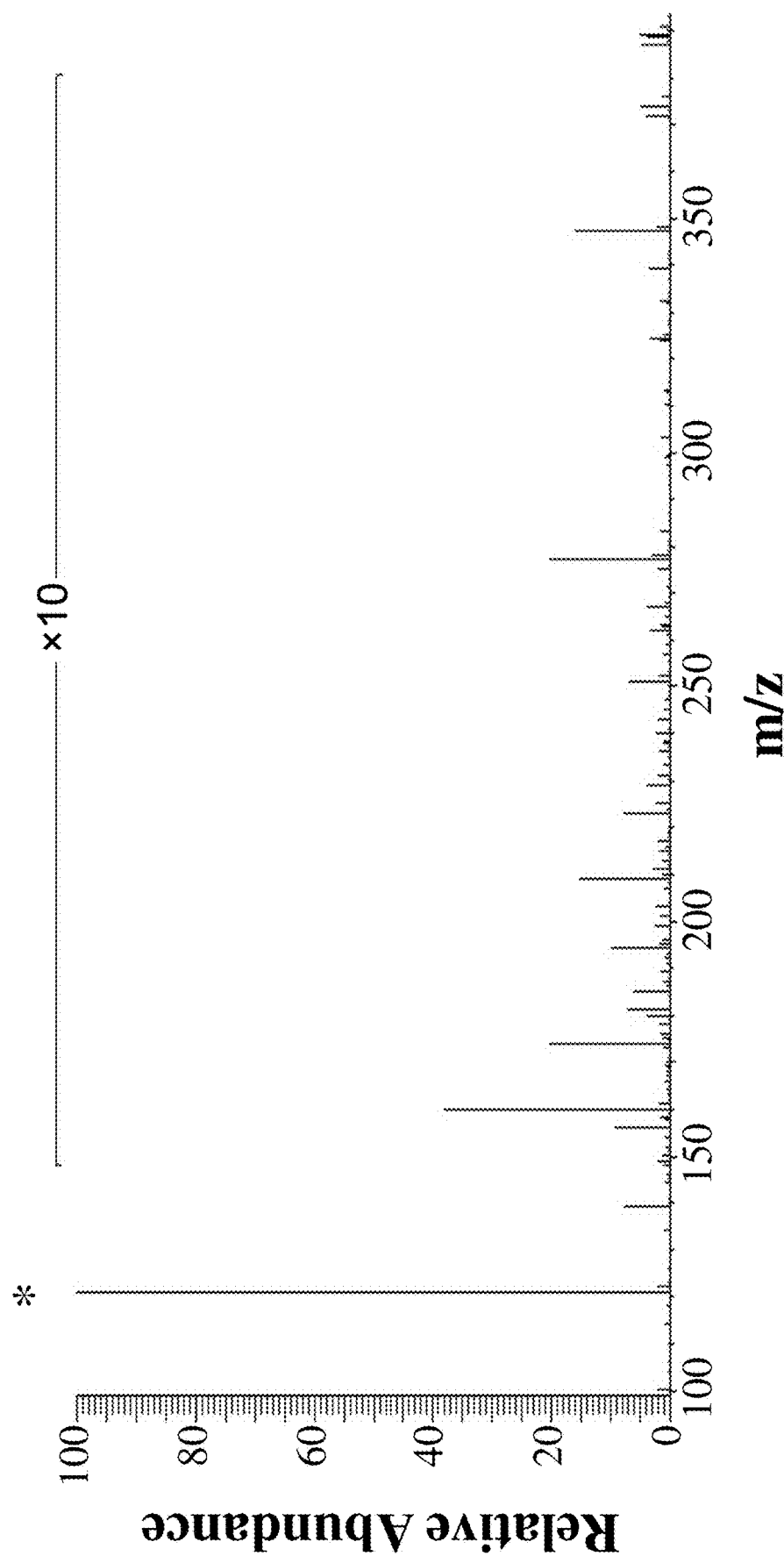
FIG. 4A is a positive DART API mass spectrum (100-380 Da) of 2000 nanoLiter (nL) volume of urine applied to a mesh, according to an embodiment of the invention.
Figure 4B:
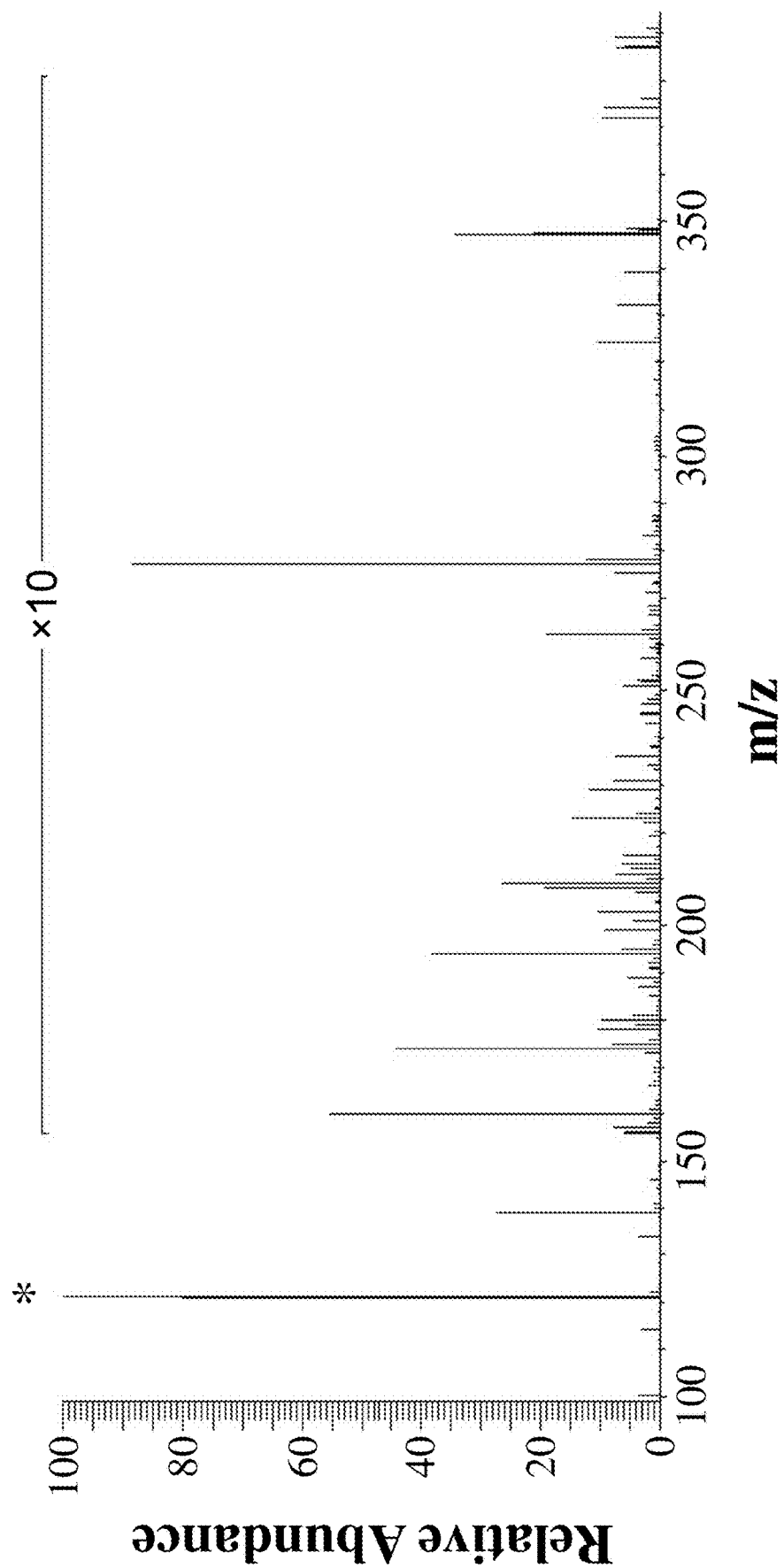
FIG. 4B is a positive DART API mass spectrum (100-380 Da) of 1000 nL volume of urine applied to a mesh, according to an embodiment of the invention.
Figure 4C:
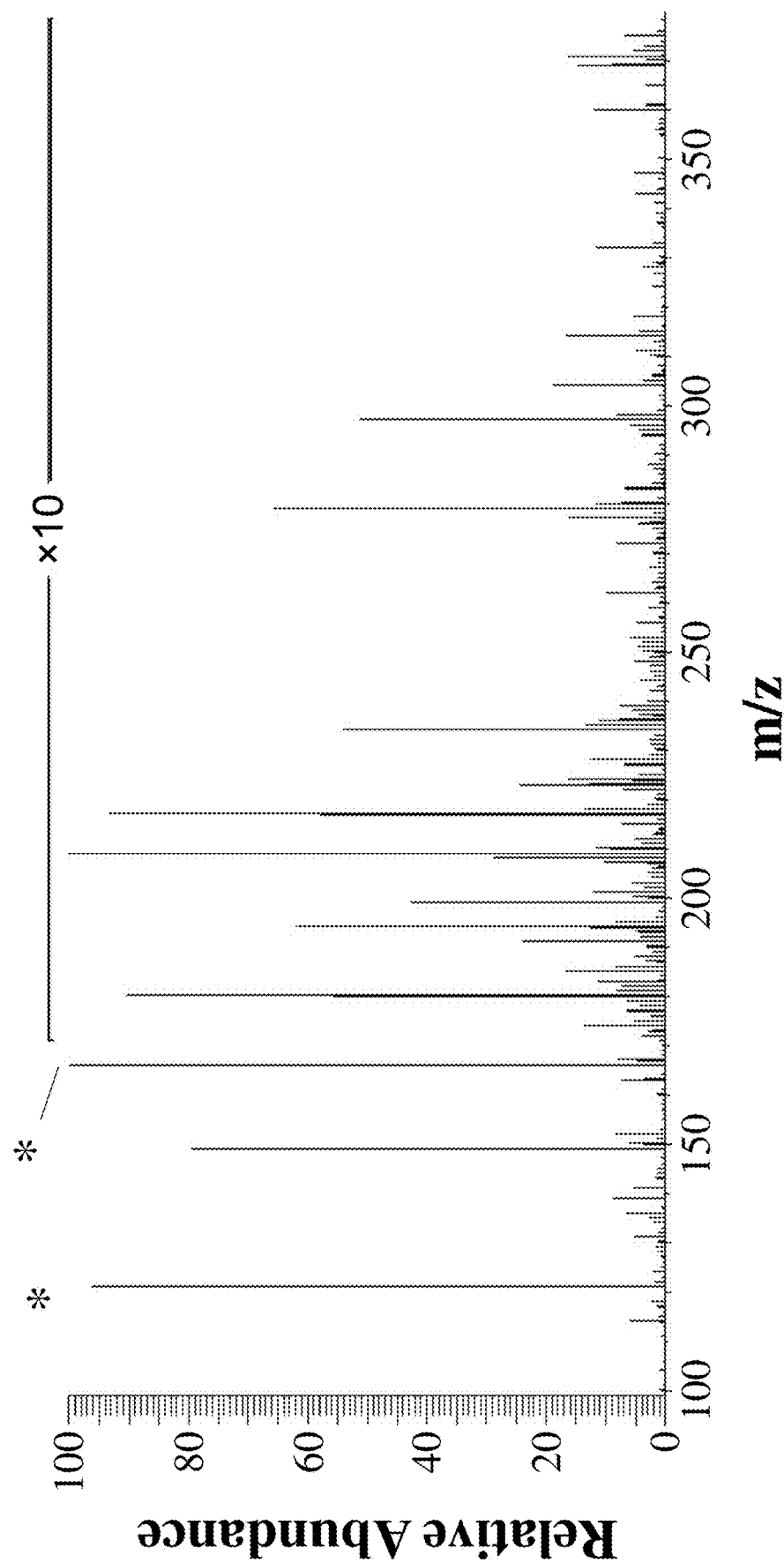
FIG. 4C is a positive DART API mass spectrum (100-380 Da) of 200 nL volume of urine applied to a mesh, according to an embodiment of the invention.

Previously it has been observed that matrix related molecules form and influence the results of analysis of a sample in a biological matrix. Analysis of a 2,000 nL volume of urine is shown in FIG. 4A. The relative abundance of the protonated dimer of urea (indicated with an asterisk (*)) at m/z 121.07 dwarfs the other ions. Therefore, in FIG. 4 the mass range above 150 Da is magnified by a factor of 10× as shown. FIG. 4A shows ions observed include the protonated dimer of urea (*) at m/z 121.07, as well as sample related ions at 160.11, 174.12, 209.15, 223.16, 277.21, 324.22, and 347.25. In this experiment the urine is pipetted onto the surface of a wire mesh (see 130 in FIG. 2). A moving stage can be employed to pass a sample through the ionizing region in an atmospheric ionization source. In FIG. 4A, the wire mesh is used to position the urine sample in a holder fixed to the moving stage which was adjusted to a speed of 5 mm/second, resulting in the sample passing through the ionization region in 0.8 seconds. Analysis of a 1,000 nL volume of urine is shown in FIG. 4B. In FIG. 4B those metabolites and analytes can be visualized and their identity can be determined based on their observed mass to charge (m/z) values. FIG. 4B shows other ions observed at m/z 160.11, 174.12, 194.17, 209.15, 223.16, 277.21, 324.22, 347.25 and 374.06. Comparison of FIG. 4A and FIG. 4B reveals that the relative abundance of the ionized metabolites relative to the dimer of urea is greater in the lower volume sample (FIG. 4B). This reduction in metabolite related ions (see FIG. 4A) is attributed to the increase in the absolute amount of area present in the higher volume sample. These data are shown for purposes of describing the dominance of the matrix effect generated in the experiment where urea, a biological waste product, is known to inhibit ionization of other molecules present in the sample as it competes with those molecules for the ionizing species present in the desorption region. In an embodiment of the experiment, analysis of a smaller volume of sample applied to the mesh is shown to permit detection of metabolites with greater signal-to-noise. As an example the analysis of 200 nL of urine, using the same sampling system and analysis parameters generates the ambient mass spectrum in FIG. 4C. FIG. 4C shows that while the protonated urea dimer ions and another background related ion are observed at m/z 121.07 and 166.14 respectively (indicated with an asterisk), the relative abundance of many biologically important metabolites is increased unexpectedly despite their absolute quantity being less. Thus reducing the sample volume increases the sensitivity for those non-matrix related ions permitting their detection. An excellent effect was observed by reducing the sample volume to increase the sensitivity. An advantageous effect was found by reducing the sample volume to increase the sensitivity. According to Beer's law, the concentration of a chemical is directly proportional to the absorbance of a solution. As applied to the analysis undertaken here, the concentration of the matrix molecules and important metabolites as well as drugs present in the urine sample remained constant in all samples. Therefore, the intensity of the biologically important molecules ions should not have increase. Surprisingly, in comparison with the results of analysis of 2000 nL and 1000 nL samples (FIG. 4A and FIG. 4B) respectively, the relative abundance of nearly all ions except for the urea dimer ion have increased as the sample volume decreased thus permitting detection and characterization of more molecules of interest despite using less sample.

In an embodiment of the present invention, a volume of sample is pipetted onto a wire mesh (see 130 in FIG. 2) in preparation for its analysis. The experiment utilizes a heated gas exiting the distal end of an ambient ionization source to effect thermal desorption. Interaction of the heated ionizing gas results in the desorption of sample related molecules as a function of their vapor pressure with very volatile, higher vapor pressure substances, entering the gas phase quickly while lower vapor pressure molecules persist on the sample surface longer and often require a higher temperature gas to desorb from the surface into the ionizing gas. Thus the temperature of the heated gas can sometimes be used to mitigate matrix effects by vaporizing the background chemicals causing the matrix effect faster than the lower vapor pressure molecules of interest. Unfortunately, in the case of urine, the urea and creatinine are observed to persist with the sample desorbing over a wide range of desorbing gas temperature and thus changing the desorption gas temperature does not eliminate the matrix suppression when operating in the normal temperature range of the experiment between room temperature and 400 degrees Celsius.

Example 1

A MOSQUITO® robot (TTP Labtech, Cambridge, UK) was used to deposit ninety six (96) samples onto a first QUICK-STRIP® (IonSense Inc., Saugus, Mass.) wire mesh screen using a 96 well format (eight (8) rows by twelve (12) columns). The 96 positions were divided into four sections of 24 positions to allow four (4) separate analyses (each of the four (4) separate analyses was made up of two (2) rows of 12). In row 1, positions 1-4, 1000 nL of a urine sample containing no added cocaine, a 250 ng/mL solution of cocaine-d3 and no added methadone were deposited; in row 1 positions 5-8, 1000 nL of a urine sample doped with a mixture of a 50 ng/mL solution of cocaine, a 250 ng/mL solution of cocaine-d3 and a 50 ng/mL solution of methadone were deposited; in row 1 positions 9-12, 1000 nL of a urine sample doped with a mixture of a 100 ng/mL solution of cocaine, a 100 ng/mL solution of cocaine-d3 and a 100 ng/mL solution of methadone were deposited; in row 2 positions 1-4, 1000 nL of a urine sample doped with a mixture of a 250 ng/mL solution of cocaine, a 250 ng/mL solution of cocaine-d3 and a 250 ng/mL solution of methadone were deposited; in row 2 positions 5-8, 1000 nL of a urine sample doped with a mixture of a 500 ng/mL solution of cocaine, a 500 ng/mL solution of cocaine-d3 and a 500 ng/mL solution of methadone were deposited; and in row 2 positions 9-12, 1000 nL of a urine sample doped with a mixture of a 1000 ng/mL solution of cocaine, a 1000 ng/mL solution of cocaine-d3 and a 1000 ng/mL solution of methadone were deposited.

The first QuickStrip was analyzed with a DART API source operated with helium as the ionizing gas set to a temperature of 350° C. for generating precursor ion of the drugs of abuse. A narrow-bore (1 mm) exit cap was used to limit the desorption area. The linear rail speed was set to 2.5 mm/sec which resulted in desorption of a sample every 2 seconds. FIG. 10A shows the Extracted Ion Chromatogram (EIC) of the cocaine (m/z 304) intact species. The EIC show significant variations in absolute intensity. FIG. 10B shows the EIC showing the intensity of the cocaine-d3 (m/z 307) intact species. Although the EIC for cocaine (FIG. 10A) show significant variations in absolute intensity, the labelled cocaine internal standard (cocaine-d3) closely mimic the variations in absolute intensity, thereby permitting normalization. FIG. 10C shows an EIC showing the intensity of the methadone (m/z 310) intact species. Because the urea tetramer was observed in the mass spectra, FIG. 10D shows an EIC showing the intensity of the urea tetramer (m/z 241) intact species. The urea-tetramer data suggests it might also be utilized for normalization.

Example 2

The Mosquito robot was used to deposit one hundred and twenty (120) samples onto a second QuickStrip wire mesh screen using a 384 well format (16 rows by 24 columns). The internal standards (500 ng/mL) were mixed with the drug of interest in urine. Dilutions were made in urine. The hundred and twenty (120) positions were divided into five (5) sections of twenty four (24) positions to allow five (5) concentrations to be analyzed. In row 1, positions 1-24, 1,000 nL of a urine sample doped with a mixture of a 50 ng/mL cocaine, 500 ng/mL cocaine-d3, 50 ng/mL methadone and a 500 ng/mL methadone-d3 were deposited; in row 2, positions 1-24, 1,000 nL of a urine sample doped with a mixture of a 100 ng/mL cocaine, 500 ng/mL cocaine-d3, 100 ng/mL methadone and a 500 ng/mL methadone-d3 were deposited; in row 3, positions 1-24, 1,000 nL of a urine sample doped with a mixture of a 250 ng/mL cocaine, 500 ng/mL cocaine-d3, 250 ng/mL methadone and a 500 ng/mL methadone-d3 were deposited; in row 4, positions 1-24, 1,000 nL of a urine sample doped with a mixture of a 500 ng/mL cocaine, 500 ng/mL cocaine-d3, 500 ng/mL methadone and a 500 ng/mL methadone-d3 were deposited; and in row 5, positions 1-24, 1,000 nL of a urine sample doped with a mixture of a 1,000 ng/mL cocaine, 500 ng/mL cocaine-d3, 1,000 ng/mL methadone and a 500 ng/mL methadone-d3 were depo sited.

Figure 9A:
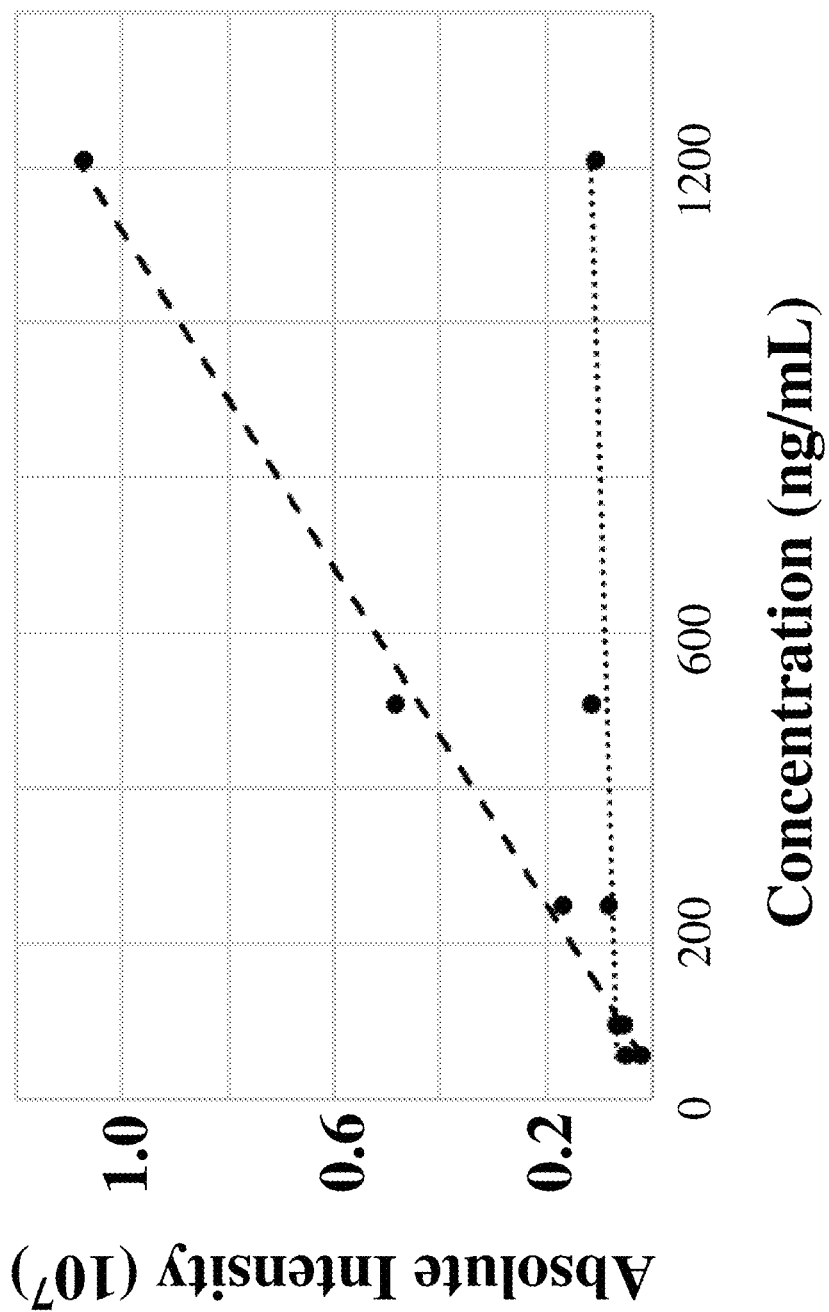
FIG. 9A is a standard calibration curve plot showing the intensity of the methadone (m/z 310) versus concentration in 200 nL urine (the urine sample was doped with a mixture of varying concentrations of cocaine, varying concentrations of methadone, a constant amount of cocaine-d3 and a constant amount of methadone-d3) spotted by a Mosquito onto a QuickStrip and analyzed by a positive DART API, according to an embodiment of the invention.
Figure 9B:
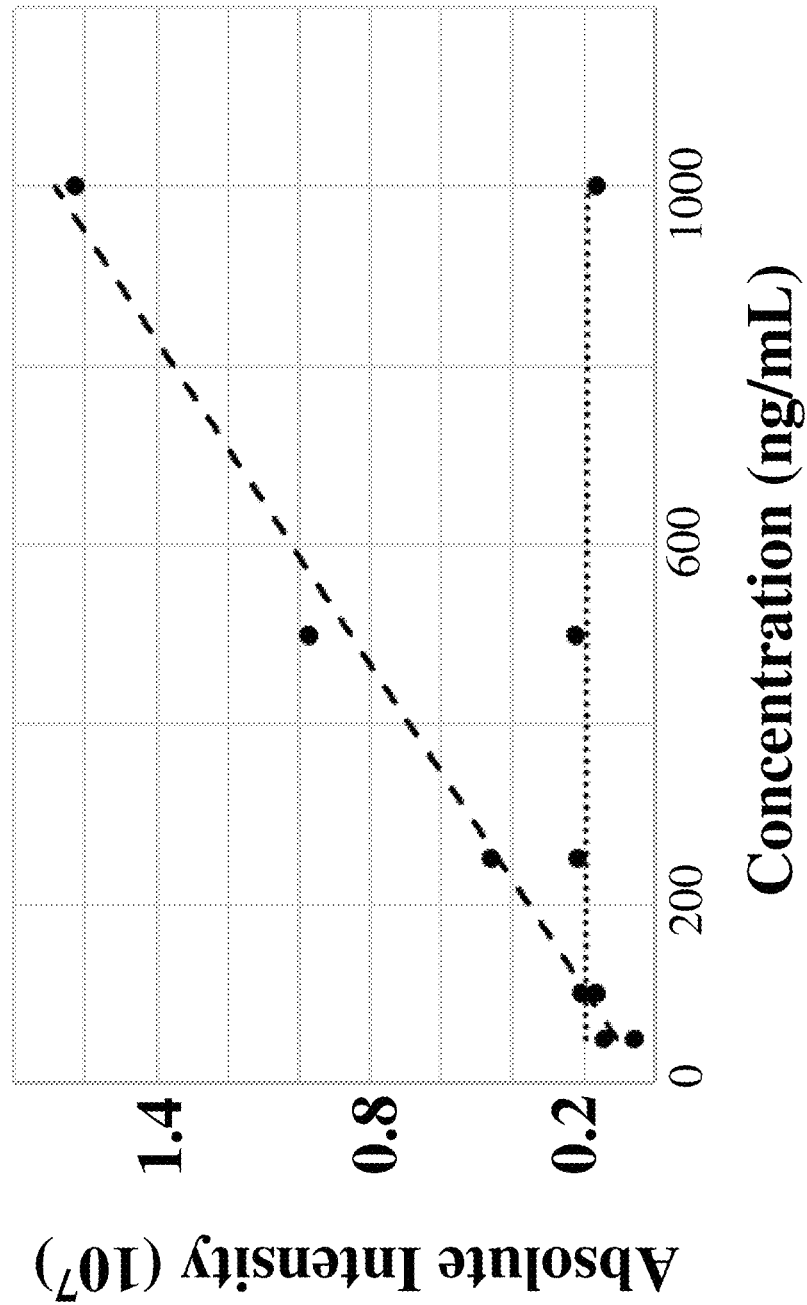
FIG. 9B is a standard calibration curve plot showing the intensity of the cocaine (m/z 304) versus concentration in 200 nL urine (the urine sample was doped with a mixture of varying concentrations of cocaine, varying concentrations of methadone, a constant amount of cocaine-d3 and a constant amount of methadone-d3) spotted by a Mosquito onto a QuickStrip and analyzed by a positive DART API, according to an embodiment of the invention.

The second QuickStrip was then analyzed with a DART API source operated with helium as the ionizing gas set to a temperature of 350° C. for generating precursor ion of the drugs of abuse. A narrow-bore (1 mm) exit cap was used to limit the desorption area. The linear rail speed was set to 2.5 mm/sec which resulted in desorption of a sample every 2 seconds. FIG. 9A is a standard calibration curve plot showing the intensity of the methadone intact species dashed line ( - - - ), m/z 310) and methadone-d3 intact species (dotted line ( . . . ) m/z 313) versus concentration. Table II shows the data for the 1,000 ng/mL methadone and 500 ng/mL methadone-d3 peak samples analyzed. Using the methanone-d3 as an internal standard, the percentage relative standard deviation for the 24 samples analyzed was 1%, with a linear regression co-efficient ($R^2$) of 0.9954. FIG. 9B is a standard calibration curve plot showing the intensity of the cocaine intact species (dashed line ( - - - ), m/z 304) and cocaine-d3 intact species (dotted line ( . . . ) m/z 307) versus concentration. Using the cocaine-d3 as an internal standard for normalization of the data, the percentage relative standard deviation for the twenty four (24) samples analyzed was less than 1%, with a linear regression co-efficient ($R^2$) of 0.988. Based on the results used to generate the data points presented in FIG. 9 the internal standard can be used to generate very accurate standard calibration curve plots.

Example 3

The Mosquito robot was used to deposit a series of samples onto a third QuickStrip wire mesh screen. A synthetic urine sample was spiked with a mixture of three drugs of abuse (lidocaine, cocaine and methadone) present at concentrations of 50 ng/mL, 100 ng/mL, 250 ng/mL, 500 ng/mL and 1,000 ng/mL. A 1000 nL aliquot of each of the samples was deposited on the third mesh. Positive DART API mass spectra of the synthetic urine samples were measured.

Figure 10E:
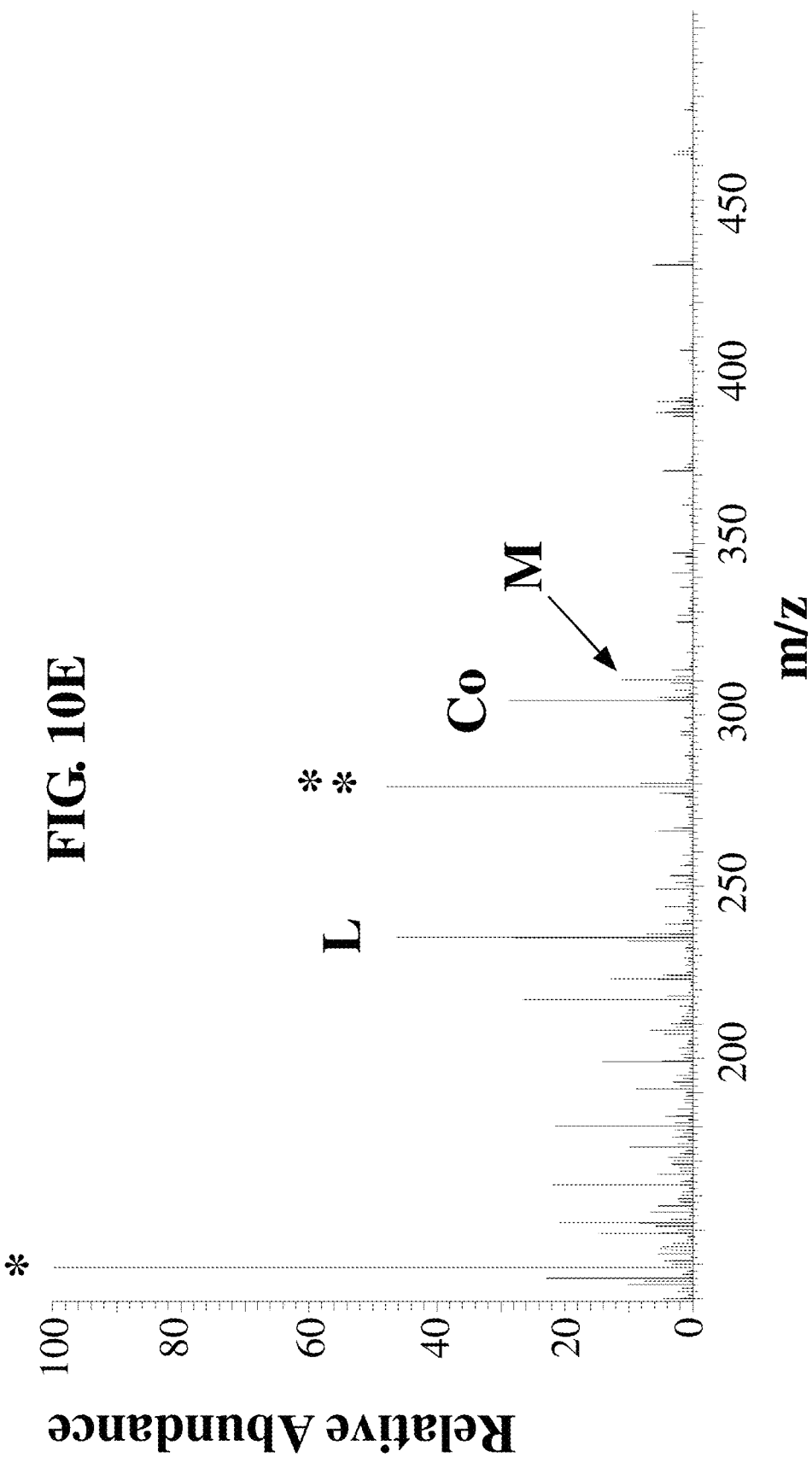
FIG. 10E is a positive DART API mass spectrum of a 1000 nL synthetic urine sample containing a mixture of lidocaine (250 ng/mL), cocaine (250 ng/mL), and methadone (250 ng/mL) spotted by a Mosquito onto a QuickStrip, according to an embodiment of the invention.

DART API mass spectral analysis of the third mesh was performed. Intense species were observed in the DART API mass spectra of the sample containing a mixture of lidocaine (250 ng/mL), cocaine (250 ng/mL), and methadone (250 ng/mL), as shown in FIG. 10E. The intense species observed in FIG. 10E at m/z 235.18, 304.15 and 310.22 correspond to the intact lidocaine (labelled L), cocaine (labelled Co) and methadone (labelled M) protonated molecule. The intense species at m/z 139.054 (labelled with an asterisk) and m/z 279.159 (labelled with a double asterisk) in FIG. 10E correspond with the di-hydroxy-oxo-ammonium methyl urea ($C_2H_8N_3O_4$ with monoisotopic mass 138.0509 Da) and di-isobutyl phthalate ($C_{16}H_{22}O_4$ with monoisotopic mass 278.152 Da) detected as protonated molecules. Accordingly, in an embodiment of the present invention, mixtures of three or more drugs of abuse present at 250 ng in urine samples can be analyzed by DART API.

Example 4

The Mosquito robot was used to deposit a series of samples onto a fourth QuickStrip wire mesh screen. A synthetic urine sample was spiked with a mixture of two drugs of abuse (cocaine and morphine) present at concentrations of 50 ng/mL, 100 ng/mL, 250 ng/mL, 500 ng/mL and 1,000 ng/mL together with a constant concentration (250 ng/mL) of an internal standard for each drug (cocaine-d3 and morphine-d3). A 1000 nL aliquot of each of the samples was deposited on the fourth mesh. Positive DART API mass spectra of the synthetic urine samples were measured.

Figure 10F:
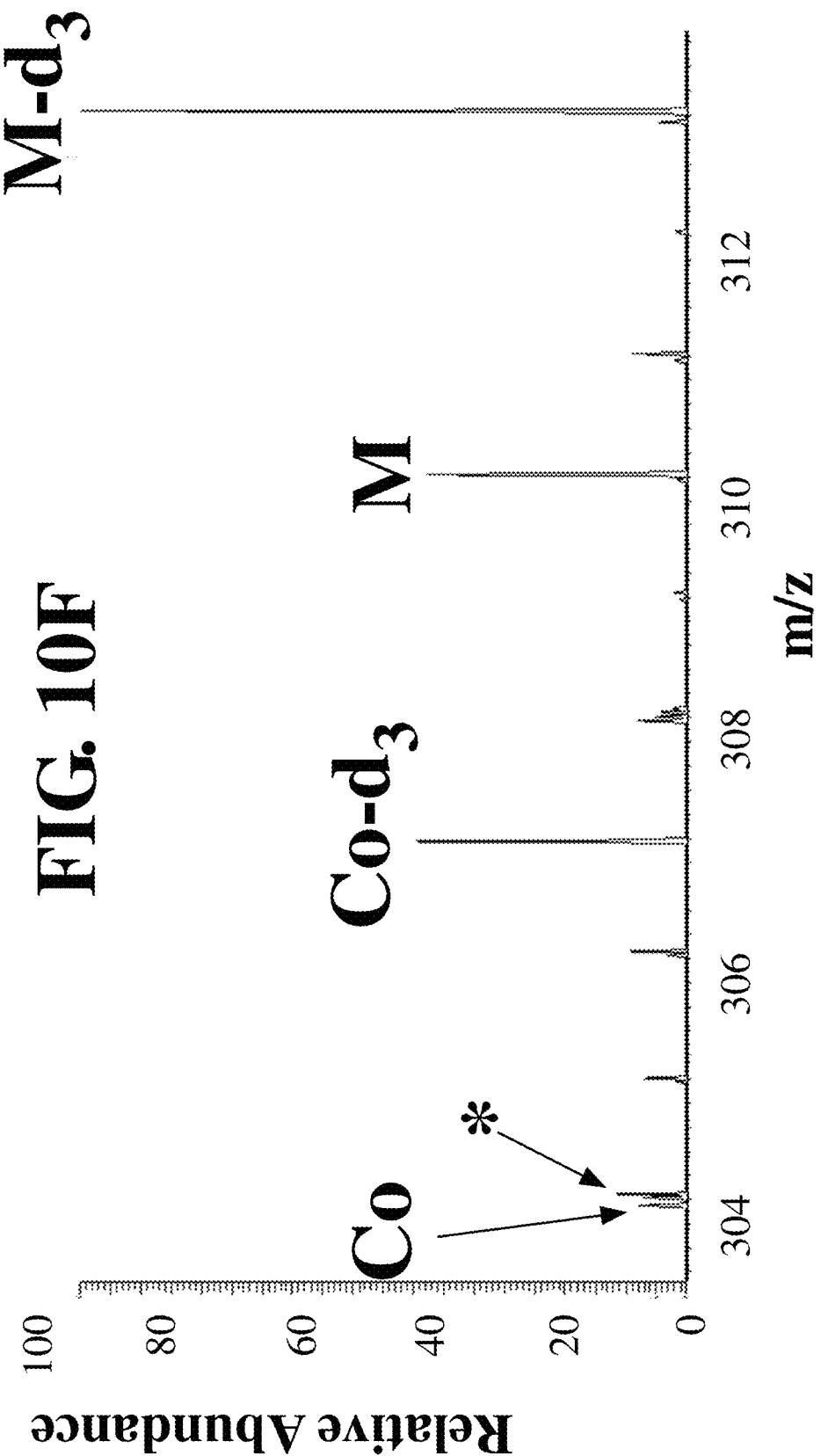
FIG. 10F is a positive DART API mass spectrum of a mixture of a 1000 nL urine sample containing a mixture of cocaine (50 ng/mL), cocaine-$d_3$ (250 ng/mL), morphine (50 ng/mL) and morphine-d$_3$ (250 ng/mL) spotted by a Mosquito onto a QuickStrip, according to an embodiment of the invention.

DART API mass spectral analysis of the fourth mesh was performed. Species were observed in the DART API mass spectra of the sample containing a mixture of cocaine (100 ng/mL), cocaine-$d_3$ (250 ng/mL), morphine (100 ng/mL) and morphine-$d_3$ (250 ng/mL), as shown in FIG. 10F. As the reference compounds are at a higher concentration, the ions generated from the reference compounds are more abundant in the mass spectrum as expected. The species were observed at m/z 304.154, 307.173, 310.218 and 313.236 corresponding to the intact cocaine (labelled Co), cocaine-d3 (labelled Co-d3), methadone (labelled M) and methadone-d3 (labelled M-d3) protonated molecule. The relatively intense species at m/z 304.248 in FIG. 10F (labelled with an asterisk) corresponds with a species observed in the mass spectra of unprocessed urine (see FIG. 2C) and unprocessed saliva (see peak labelled with asterisk at m/z 304.248 in FIG. 2D) indicating that this is likely a background chemical species. Under these conditions 100 ng/mL was the lowest level at which cocaine and morphine each with an internal standard could be clearly identified. Accordingly, in an embodiment of the invention, mixtures of two or more drugs of abuse at varying concentrations each with an internal standard in urine samples can be analyzed by DART API.

In the prior art, analysis of urine, and other biological samples, can be facilitated by using a chemical separation method such as liquid chromatography to separate and isolate the background chemicals such as urea, from the analytes (present in the biological sample) in order to ionize and detect those molecules. In mass spectrometry, urea is commonly the molecule causing the most significant suppression of molecules of interest. Introduction of the sample into the chromatography system results in the urea being selectively separated and isolated from those molecules of interest in time. The prior art experiment is typically referred to as 'dilute and shoot', where the dilution provides the liquid for removing the urea while the chromatography material delays the passage of molecules of interest through the chromatography column by an interval of time sufficient that they are separated from the urea.

In an embodiment of the present invention, the matrix effect can partially be addressed by dilution of sample with water, as in the so called 'dilute and shoot experiment' without the requirement for the chromatography system. However, dilution of urine with water in a 'dilute and shoot experiment' does not address the suppression. In an embodiment of the invention dilution of a sample to reduce the concentration of the suppressing molecules can be utilized to permit detection of molecules of interest.

Example 5

In chemical analysis, the general condition is that the greater the concentration of a molecule of interest in the sample the greater the abundance of signal detected by the analytical instrument (Beer's law). Assuming no matrix effect, as the analysis volume is decreased the signal should decrease by the same proportion. In order to examine whether the matrix behavior was dependent on concentration of urea two sets of different concentrations of cocaine and its internal standard were pipetted onto a wire mesh screen (see 130 in FIG. 2) and analyzed using DART with the same moving stage presentation speed. A first and a second sample were applied on a fifth QuickStrip mesh (see 130 in FIG. 2). The first sample was a 200 nL volume of urine containing 200 ng of cocaine and 200 ng of cocaine-d3 as an internal standard. The second sample was prepared by diluting a 200 nL aliquot of the urine with 800 nL of deionized water containing 200 ng of cocaine and 200 ng of cocaine-d3 as an internal standard. The 1000 nL sample was applied on the fifth mesh.

Figure 5A:
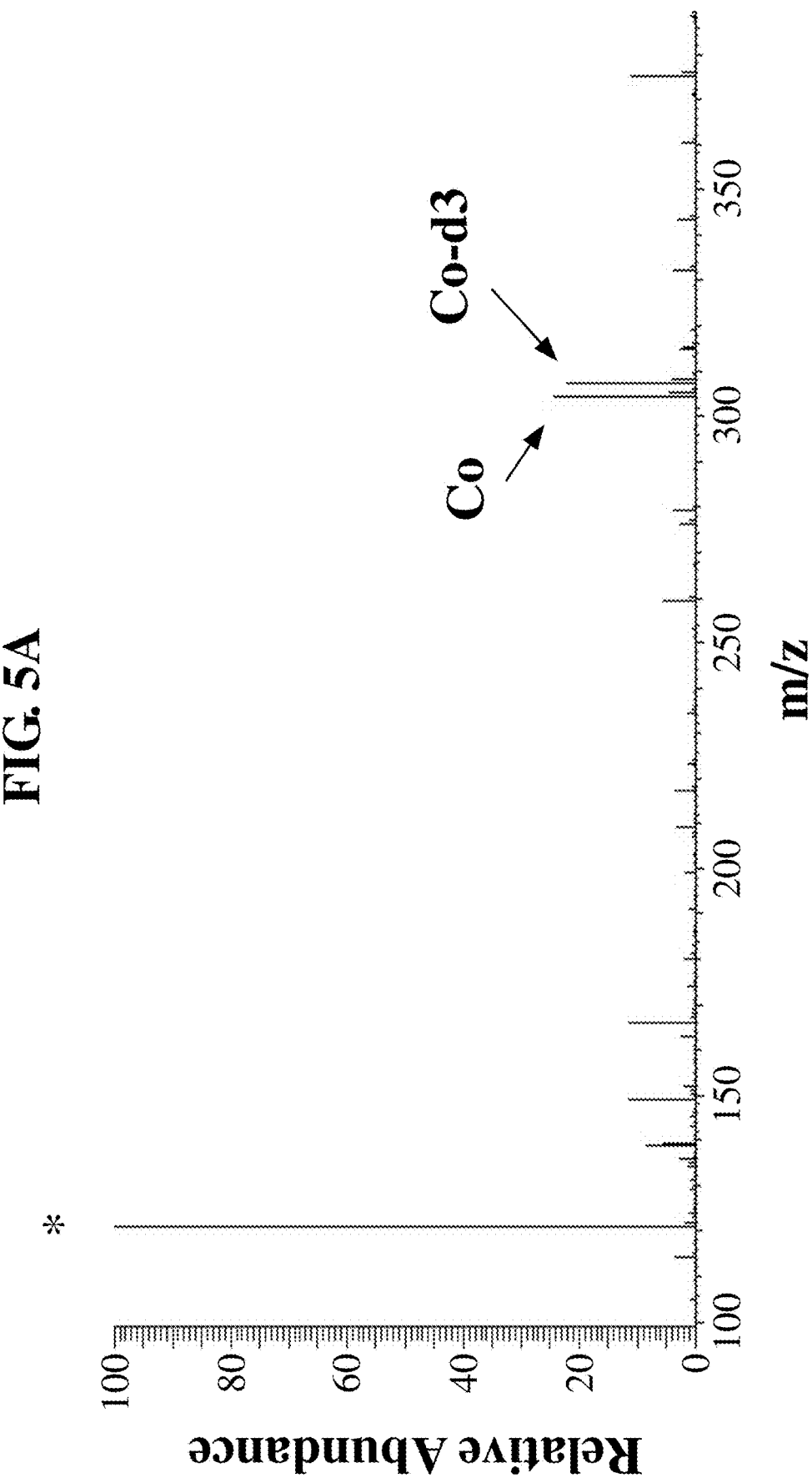
FIG. 5A is a positive DART API mass spectrum (100-400 Da) of 200 nL volume of urine containing cocaine, and cocaine-d3 applied to a mesh, according to an embodiment of the invention.
Figure 5B:
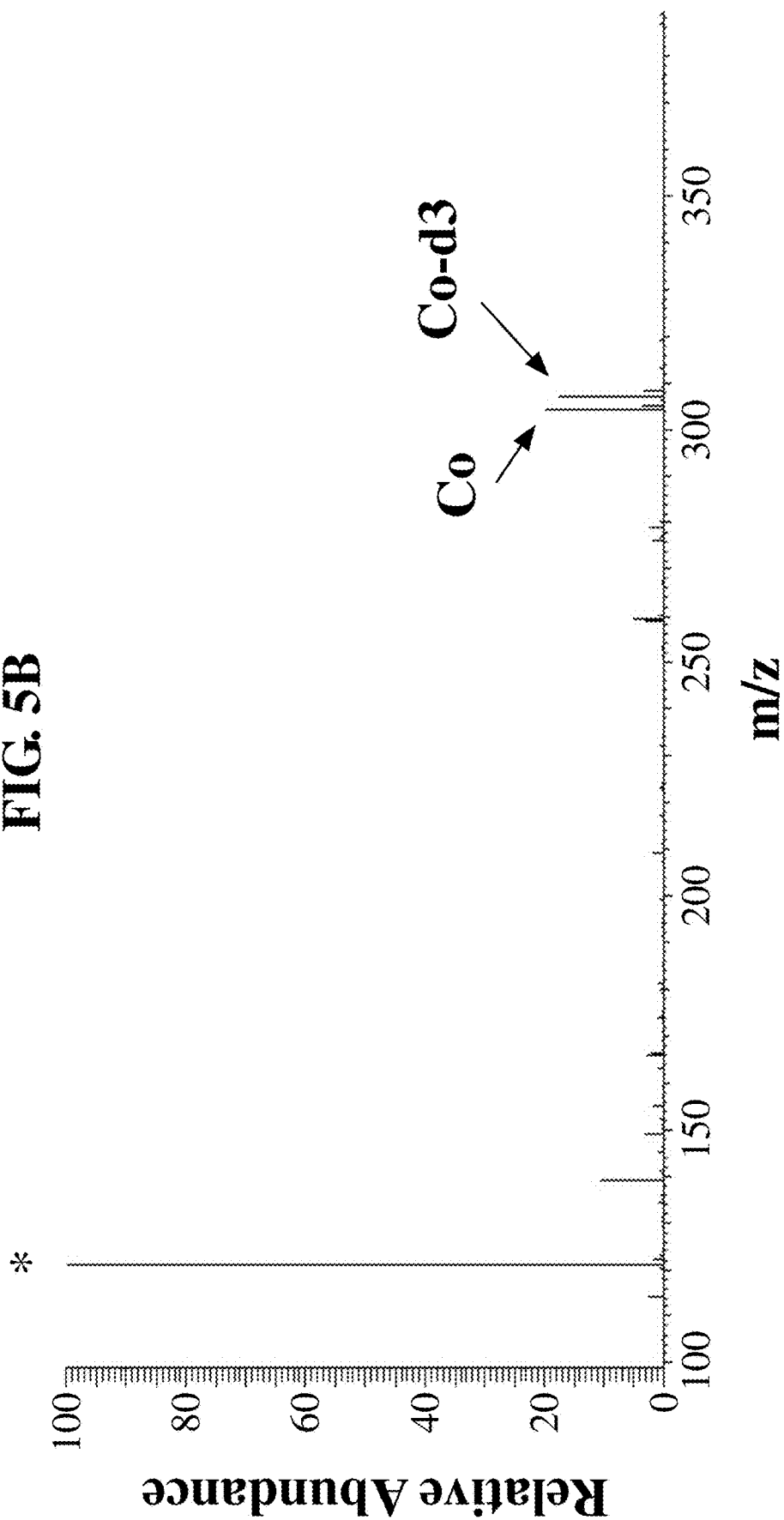
FIG. 5B is a positive DART API mass spectrum (100-400 Da) of 1000 nL volume of 20% urine in water containing cocaine, and cocaine-d3, standard applied to a mesh, according to an embodiment of the invention.

DART API mass spectral analysis of the fifth mesh was performed. Both mass spectra (FIG. 5A and FIG. 5B) have major ions at m/z 121.07, 304.15, and 307.15. The species correspond with an intense protonated urea dimer (m/z 121.07) (indicated with an asterisk) together with the intact cocaine ($C_{17}H_{21}NO_4$ monoisotopic mass 303.147 Da) and the cocaine-d3 protonated species, see FIG. 5A and FIG. 5B. The analysis of the 200 nL sample of the undiluted urine produced the mass spectrum shown in FIG. 5A. The analysis of the 1000 nL sample of the diluted urine (1:5 dilution in deionized water) produced the mass spectrum shown in FIG. 5B. As expected the most abundant ion detected in both samples was the protonated urea-dimer. Unexpectedly, diluting the sample with deionized water did not improve the sensitivity. In fact, normalizing the relative abundance of the cocaine species to the cocaine-d3 internal standard the analysis of the non-diluted sample, indicated that the undiluted sample, produced approximately 25% greater signal than the diluted sample despite the presence of equal quantities of the cocaine and cocaine-d3 molecules in each sample. Further, the dilution is observed to slightly increase the matrix effect. That is, dilution with deionized water did not alleviate the matrix effect where the background species interfered with the analysis of the molecule of interest. We note that the 20% reduction in signal observed correlates with approximately one half of the reduction from 1,000 ng/mL to 500 ng/mL based on the cocaine standard curve from FIG. 9.

Example 6

The Mosquito robot was used to deposit a series of samples onto a sixth QuickStrip wire mesh screen. A urine sample was spiked with a mixture of methadone present at concentrations of 50 ng/mL, 100 ng/mL, 250 ng/mL, 500 ng/mL and 1,000 ng/mL together with a constant concentration (250 ng/mL) of methadone-d3. A 200 nL aliquot of each of the samples was deposited on the sixth mesh. The robot sample positioning speed was set to five (5) mm/second. Positive DART API mass spectra of the urine samples were continually measured as the robot positioned the sixth mesh.

FIGS. 6A-6E presents the results of analysis of the concentrations of 50 ng/mL, 100 ng/mL, 250 ng/mL, 500 ng/mL and 1,000 ng/mL methadone applied to the sixth mesh, respectively. Ionized species are observed at m/z 310.235, 311.242, 312.247, 313.142 and 313.236. The m/z 310.235 species (labelled 'M') corresponds with methadone ($C_{21}H_{27}NO$ monoisotopic mass 309.2093 Da) protonated species. The concentration of methadone increases with increasing concentration of methadone. The m/z 313.236 species (labelled 'M-d3') corresponds with methadone-d3 ($C_{21}{}^1H_{24}{}^2H_3NO$ monoisotopic mass 312.2297 Da) protonated species. The concentration of methadone-d3, an internal standard remains approximately constant in each sample. Background species are observed (see double asterisk (m/z 311.242) and single asterisk species (m/z 313.142). The single asterisk species is fully resolved from the analytically important methadone-d3 (m/z 313.24). FIG. 6A shows the mass spectrum observed from the 200 nL urine sample applied, where 10 pg of methadone and 40 pg of methadone-d3 were present on the sixth mesh. FIG. 6B shows the mass spectrum observed from the 200 nL urine sample applied, where 20 pg of methadone and 40 pg of methadone-d3 were present on the sixth mesh. FIG. 6C shows the mass spectrum observed from the 200 nL urine sample applied, where 50 pg of methadone and 40 pg of methadone-d3 were present on the sixth mesh. FIG. 6D shows the mass spectrum observed from the 200 nL urine sample applied, where 100 pg of methadone and 40 pg of methadone-d3 were present on the sixth mesh. FIG. 6E shows the mass spectrum observed from the 200 nL urine sample applied, where 200 pg of methadone and 40 pg of methadone-d3 were present on the sixth mesh. In FIGS. 6A-6E the concentration of methadone (m/z 310.2) is increasing with each experiment while the concentration of the methadone-d3 internal standard (m/z 313.1) is constant. In FIG. 6A-6E representative spectra from four (4) replicate measurements made are shown. In FIGS. 6A-6C the methadone relative intensity is increasing. In FIG. 6C-FIG. 6E, the methadone relative abundance is approximately constant. As shown in Table I, the intensity of the m/z 310.2 species increased as the concentration of methadone in the sample was increased. There is a background peak observed indicated with a double asterisk (m/z 311.2). We expect that the methadone $C^{13}$ peak will be unresolved from this background species. When the methadone $C^{13}$ species is less intense, (for methadone ($C_{21}H_{27}NO$) the $C^{13}$ species should be approximately 21% of the $C^{12}$ species) the $C^{13}$ species will have little contribution on the shoulder of the background species. However, as the methadone $C^{12}$ species increases in intensity, the $C^{13}$ will be more clearly observed as an unresolved shoulder on the 311.24 background peak (see FIGS. 6C-6D). As shown in FIGS. 6A-6E, the intensity of the methadone-d3 species (m/z 313.2) remained constant until the 1000 ng/mL concentration. The background species indicated with a double asterisk reduces in intensity as the methadone concentration increases, again reflecting the increased competition for the charge as the number of methadone molecules in the sample increases. In an embodiment of the invention these results demonstrate the capability for direct API and detection of a drug of abuse in unprocessed urine where methadone is present at concentrations ranging from 50 to 1000 ng/mL using a sample volume of 200 nL with the sample positioning speed set to five (5) mm/second. In an embodiment of the present invention, the matrix effect has expectantly been reduced by limiting the volume of the sample applied to the wire mesh.

FIG. 6 demonstrates the detection of a low vapor pressure drug compound present in the sample across a clinically relevant concentration range despite the presence of the matrix related ion suppressing molecules in the sample. The reduction in sample volume reduces the area occupied by the sample on the wire mesh influencing the desorption of the sample.

Example 7

A Mosquito robot was used to deposit twenty-four (24) samples onto a seventh QuickStrip wire mesh screen using a 1536 well format. A 200 nL urine sample doped with methadone (1,000 ng/mL) and methadone-$d_3$ (500 ng/mL) in 80% deionized water were deposited in each position. FIG. 11A is a partial display of an EIC trace showing the intensity of the methadone (m/z 310) intact species generated in positive ionization mode with DART from the seventh screen measured at a speed of four (4) seconds per position. FIG. 11B is a partial display of an EIC trace showing the intensity of the methadone-$d_3$ (m/z 313) intact species generated in positive ionization mode with DART from the seventh screen. Each peak in FIG. 11 represents the analysis of a separate deposited sample on the seventh screen. FIG. 11C is a standard calibration curve plot showing the intensity of the methadone (m/z 310) intact ion species analyzed from the seventh mesh. Using the intensity of the methadone-d3 as an internal standard to generate a ratio of the relative intensity and then fitting the data with a linear regression plot, a co-efficient ($R^2$) of 0.97 was obtained. FIG. 11D is a positive ambient ionization DART mass spectrum of one of the spots on the seventh mesh containing a mixture of methadone (200 pg) and methadone-$d_3$ (100 pg). An intense species was observed at m/z 310.216 corresponding to the intact methadone (labelled M) protonated molecule. The methadone-d3 (labelled M-d3) protonated molecule was also prominent. A background species was observed at m/z 332.148 (labelled with an asterisk).

Example 8

A Mosquito robot was used to deposit a series of urine samples onto an eighth QuickStrip wire mesh screen using a 1536 well spacing format (32 rows by 48 columns, where the first row was spotted and sampled). 200 nL aliquots were applied on the eighth mesh. The urine samples (0.9 mL) were added to 0.1 mL of a 50% methanol 50% deionized water solution containing 10 mg/mL of the drug of addiction to generate the 1 mg/mL (i.e., 1 ng/nL) 'test solutions', where the drug of addiction was: (A) cocaine (row 1, columns 1-12); (B) lidocaine (row 1, columns 13-24); (C) caffeine (row 1, columns 25-36) and methadone/methadone d3 (row 1, columns 37-48).

FIGS. 12A-12D are EIC traces showing the intensity of two separate positive ionization mode DART API analysis (i.e., two sequential depositions of 200 nL on the eighth mesh) accumulated at 5 mm/sec (equivalent to 4 positions/1.8 sec) showing baseline separation of each measurement of the intact species. FIG. 12A is the EIC trace showing two separate analyses of row 1, columns 1-12 (i.e., two sequential depositions of 200 nL of 1 mg/mL cocaine on the eighth mesh) showing the intensity of the cocaine (m/z 235) intact species. FIG. 12B is the EIC trace showing two separate analyses of row 1, columns 13-24 (i.e., two sequential depositions of 200 nL of 1 mg/mL lidocaine on the eighth mesh) showing the intensity of the lidocaine (m/z 235) intact species. FIG. 12C is the EIC trace showing two separate analyses of row 1, columns 25-36 (i.e., two sequential depositions of 200 nL of 1 mg/mL caffeine on the eighth mesh) showing the intensity of the caffeine (m/z 195) intact species. FIG. 12D is the EIC trace showing two separate analyses of row 1, columns 37-48 (i.e., two sequential depositions of 200 nL of 1 mg/mL methadone/methadone d3 on the eighth mesh) showing the intensity of the methadone (m/z 310) intact species.

FIGS. 12E-12H are positive ambient ionization DART mass spectra corresponding to one of the separate analysis shown in FIGS. 12A-12D. A relatively intense background ion species at m/z 279.159 (labelled with an asterisk) is observed in all of the spectra and corresponds with the di-isobutyl phthalate (monoisotopic mass 278.152 Da) detected as a protonated molecule. FIG. 12E is one of the separate analysis shown in FIG. 12A (200 nL of 1 mg/mL cocaine on the eighth mesh). An intense species was observed at m/z 304.154 corresponding to the intact protonated cocaine (labelled Co). FIG. 12F is one of the separate analysis shown in FIG. 12B (200 nL of 1 mg/mL lidocaine on the eighth mesh). In FIG. 12F an intense species was observed at m/z 235.180 corresponding to the intact protonated lidocaine (labelled L). FIG. 12G is one of the separate analysis shown in FIG. 12C (200 nL of 1 mg/mL caffeine on the eighth mesh). In FIG. 12G an intense species was observed at m/z 195.087 corresponding to the intact protonated caffeine (labelled C). FIG. 12H is one of the separate analysis shown in FIG. 12D (200 nL of 1 mg/mL methadone/methadone d3 on the eighth mesh). In FIG. 12H an intense species was observed at m/z 310.216 corresponding to the intact protonated methadone (labelled M). Based on the analysis shown in FIG. 12, 200 nL aliquots containing 200 ng of caffeine, lidocaine or cocaine can be analyzed in urine (diluted 20:80 with deionized water).

Example 9

A Mosquito robot was used to deposit a series of saliva samples onto a ninth QuickStrip wire mesh screen using a 1536 well spacing format. The saliva samples were doped with a mixture of equal concentration of caffeine, lidocaine, cocaine, and methadone (varying between 50 ng/mL and 1,000 ng/mL) and a constant amount of methadone-$d_3$ (250 ng/mL) then diluted to 10% using deionized water to generate the 'test solutions'. A 200 nL aliquot of the test solutions was applied to the ninth mesh and analyzed with positive ambient ionization DART (see FIGS. 13A-13E) at a sample positioning speed set to five (5) mm/second.

In FIG. 13A the concentration of caffeine, lidocaine, cocaine, and methadone in the test solutions was 50 ng/mL. Protonated molecule ions for caffeine, lidocaine, cocaine or methadone were not observed under these conditions. The m/z 291.195 is the same species detected in the normal saliva (see TABLE V). In FIG. 13B the concentration of caffeine, lidocaine, cocaine, and methadone in the test solutions was 100 ng/mL. The protonated caffeine (m/z 195.0875) was observed under these conditions, however the lidocaine, cocaine and methadone remained hidden in the background. In FIG. 13C the concentration of caffeine, lidocaine, cocaine, and methadone in the test solutions was 250 ng/mL and the protonated species for each of caffeine (m/z 195.088), lidocaine (m/z 235.181), cocaine (m/z 304.154) and methadone (m/z 310.216) were observed. In FIG. 13D the concentration of caffeine, lidocaine, cocaine, and methadone in the test solutions was 500 ng/mL and the intensity of the protonated caffeine, lidocaine, cocaine, and methadone species each increased compared with FIG. 13C. In FIG. 13E the concentration of caffeine, lidocaine, cocaine, and methadone in the test solutions was 1,000 ng/mL and the intensity of the protonated lidocaine, cocaine, and methadone species increased compared with FIG. 13D. The intensity of the caffeine protonated species remained constant at this highest concentration. Based on the analysis shown in FIG. 13, 200 nL aliquots of containing 50 pg of caffeine, 100 pg lidocaine, 100 pg cocaine or 100 pg methadone can be analyzed in saliva after dilution to 10% volume/volume with deionized water, where the dilution serves to facilitate a less viscous solution for handling by robotic dispensers.

In an embodiment of the invention, the sample can be restricted to an area of 0.01 mm$^2$ where the volume of the biological sample applied to the area is between a lower limit of approximately 1 nL and an upper limit of approximately 10 nL. In an embodiment of the invention, the sample can be restricted to an area of 0.1 mm$^2$ where the volume of the biological sample applied to the area is between a lower limit of approximately 10 nL and an upper limit of approximately 50 nL. In an embodiment of the invention, the sample can be restricted to an area of less than 1 mm$^2$ where the volume of the biological sample applied to the area is between a lower limit of approximately 50 nL and an upper limit of approximately 250 nL. When applying a sample of approximately 1 nL, approximately means plus or minus forty (40) percent (%). When applying a sample of approximately 10 nL, approximately means plus or minus twenty (20) percent (%). When applying a sample of approximately 100 nL, approximately means plus or minus ten (10) percent (%). When applying a sample of approximately 1000 nL, approximately means plus or minus five (5) percent (%). When applying a sample of approximately 1 pg, approximately means plus or minus twenty (20) percent (%). When applying a sample of approximately 10 pg, approximately means plus or minus fifteen (15) percent (%). When applying a sample of approximately 100 pg, approximately means plus or minus ten (10) percent (%). When applying a sample of approximately 1 ng, approximately means plus or minus five (5) percent (%). When applying a sample of approximately 1 pg/mm$^2$, approximately means plus or minus twenty (20) percent (%). When applying a sample of approximately 10 pg/mm$^2$, approximately means plus or minus fifteen (15) percent (%). When applying a sample of approximately 100 pg/mm$^2$, approximately means plus or minus ten (10) percent (%). When applying a sample of approximately 1000 pg/mm$^2$, approximately means plus or minus five (5) percent (%).

Presence of an Ion Intensifier Reagent

In an embodiment of the invention addition of a different matrix suppression chemical is observed to permit detection of targeted compounds in the presence of background chemicals. In these experiments the ion suppression solvent DMSO was added to the volume of untreated urine in varying concentrations.

Example 10

Initially, the sensitivity of DART API was determined for a drug of abuse with an internal standard in an ion intensifier reagent that was a known ion suppressor. A Mosquito robot was used to deposit (4 rows of 24 columns) ninety-six (96) 200 nL samples onto a tenth QuickStrip wire mesh screen using a 384 well spacing format. The ninety six (96) positions were divided into four (4) sections of twenty four (24) to allow four (4) separate analyses. The samples were a mixture of varying concentration of methadone (2,000-40,000 ng/mL) and methadone-d$_3$ (1,000-20,000 ng/mL) in 100% DMSO. The tenth QuickStrip was analyzed with positive ambient ionization DART API (see FIGS. 14A-14H) at a sample positioning speed set to two (2) mm/second.

Figure 1:
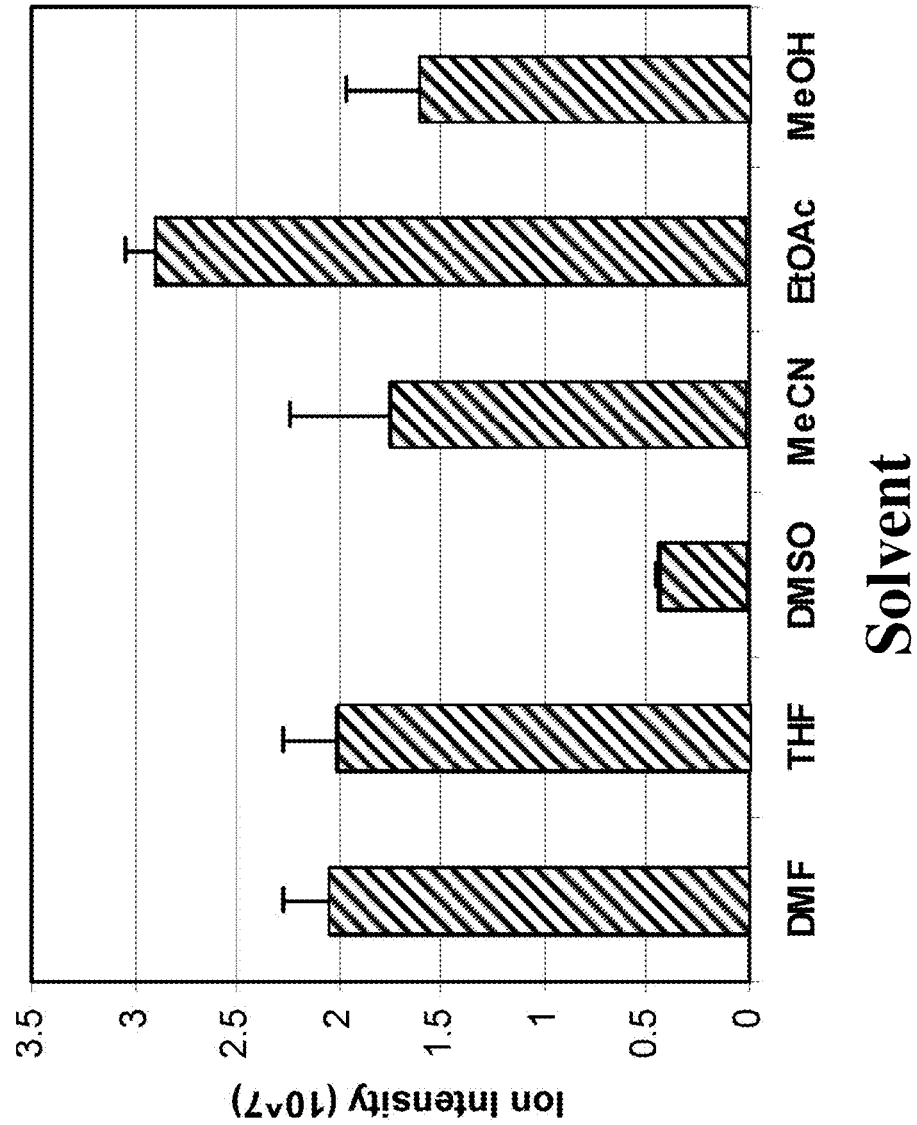
FIG. 1 is a histogram showing a prior art comparison of the intensities of the molecular ion of warfarin, $[M+H]^+$ =309, dissolved in different solvents after positive DART API ionization (reproduced from Petucci et al., Anal. Chem. 79 (2007) 5064-5070)

As shown in FIG. 1, DMSO is a suppressor of ionization. However, even though DMSO is a suppressor of ionization, unexpectedly intense signals were observed for methadone and methadone-d3 in FIGS. 14A-14G. An excellent effect was observed by using a suppressor of background ions to reduce the detection limits. An advantageous effect was found by using a suppressor of ionization to increase the detection of an ion by reducing the contribution of background ions to the mass spectrum. FIGS. 14A-14D are EIC traces showing the intensity of m/z 310 methadone intact species. FIGS. 14E-14H are EIC traces showing the intensity of m/z 313 methadone-d3 intact species. In FIGS. 14A and 14E the methadone concentration was 2,000 ng/mL and the methadone-d3 concentration was 1,000 ng/mL and the relative intensity is increased by a factor of 5 compared with FIGS. 14B-14D and 14F-14H. In FIGS. 14B and 14F the methadone concentration was 10,000 ng/mL and the methadone-d3 concentration was 5,000 ng/mL. In FIGS. 14C and 14G the methadone concentration was 20,000 ng/mL and the methadone-d3 concentration was 10,000 ng/mL. In FIGS. 14D and 14H the methadone concentration was 40,000 ng/mL and the methadone-d3 concentration was 20,000 ng/mL. The analysis in FIGS. 14A and 14E shows that at a minimum 1.3 pmol of methadone and 0.64 pmol of methadone-d3 can be detected. The general appearance of the EIC traces in FIGS. 14A and 14B indicate that area is proportional to concentration, however between 14C and 14E the area does not increase indicating that at those higher concentrations quantitation is not possible due to detector saturation even in the presence of the ionization suppressor.

Example 11

Next, the ion suppression solvent, DMSO, was added to a volume of untreated urine in varying concentrations. The volume of urine applied to an eleventh mesh was held constant while the concentration of a low vapor pressure drug molecule was varied to document the influence of matrix effects on the detection of the low vapor pressure molecule. A Mosquito robot was used to deposit a series of 1000 nL samples onto a eleventh QuickStrip wire mesh screen. The samples were generated by mixing 1000 nL of untreated urine doped with a 1000 nL aliquot of varying concentration of methadone (1,000-20,000 ng/mL) in 100% DMSO. The eleventh QuickStrip was analyzed with positive ambient ionization DART API, 100-500 Da (mass spectra showing 100-350 Da are shown in FIGS. 7A-7D) each spectrum shown represents the average of between 20 and 32 spectra.

FIG. 7A shows the 1,000 ng/mL, FIG. 7B shows the 5,000 ng/mL, FIG. 7C shows the 10,000 ng/mL and FIG. 7D shows the 20,000 ng/mL methadone applied to the eleventh mesh. The methadone intact ion abundance at m/z 310.2 increases with increasing concentration.

FIG. 7A can be compared with FIG. 10E where the urea dimer (m/z 121) has a relative abundance of 100 compared to the methadone species (m/z 310) which has a relative abundance of approximately 10%. Note, the m/z 157.0 species (indicated with an asterisk) in FIG. 7A corresponds with the DMSO dimer (i.e., [2M+H]$^+$). The urea dimer observed as the base peak in FIG. 10E is not observed in FIG. 7A. While the DMSO is presumably decreasing the sensitivity to methadone (based on the documented effect on Warfarin, see FIG. 1), it is inhibiting the ionization of the urea matrix species even more. The urea dimer relative abundance in FIGS. 7A-7D is less than one (1)%. Further, the presence of the DMSO dimer can be used to compare the relative abundance of the methadone, as the methadone concentration is increased in FIGS. 7A-7D.

Unexpectedly, in FIGS. 7A-7D nearly all of the background ions associated with urea and creatine including the protonated urea dimer are of reduced relative intensity while the chemical of interest (methadone) is detected over a wide concentration ranging from a barely detectable signal for the 0.002 mg/mL and increasing to an intense species measured for the 0.004 mg/mL concentration. An excellent effect was observed where all background ions associated with urea and creatine including the protonated urea dimer are of reduced relative intensity while the chemical of interest (methadone) is detected over a wide concentration. An advantageous effect was found reducing background ions associated with urea and creatine including the protonated urea dimer are of reduced relative intensity while the chemical of interest (methadone) is detected over a wide concentration. This is despite the fact that DMSO generally inhibits ion formation of all ions present in a sample with stronger suppression characteristics than most all other solvents used in LC/MS as shown in FIG. 1.

Example 12

A Mosquito robot was used to deposit a series of 1000 nL samples onto a twelfth QuickStrip wire mesh screen. The samples were generated by applying urine doped with methadone 500 ng/mL and cocaine 500 ng/mL in varying amounts of DMSO to generate 0, 0.5, 2.5, 5, 12.5 and 50% DMSO solutions. The twelfth QuickStrip was analyzed with positive ambient ionization DART API, 100-500 Da (mass spectra showing 180-470 Da are shown in FIGS. 8A-8B) each spectrum shown represents the average of between 6 and 7 spectra.

FIG. 8A shows the urine spiked with methadone and cocaine 0% DMSO applied to a twelfth mesh. FIG. 8B shows the urine spiked with methadone and cocaine resulting in a 50% DMSO solution applied to a twelfth mesh. The cocaine protonated species (m/z 304.15) and methadone protonated species m/z 310.216 are labelled as 'Co' and 'M' in FIG. 8A. These species are both present in FIG. 8B. Ions identified as background are labelled in FIG. 8A by the presence of a star above the peak. Unexpectedly, the addition of DMSO significantly changes the appearance of the measured spectrum. Where the expected result of the presence of DMSO in the ionizing region would be suppression of all analyte ions. However, in the situation of small volume sampling presented herein, unexpectedly, the addition of DMSO allowed analysis of the molecule of interest by reducing the presence of other species, e.g., background ions. That is, an excellent effect was observed where the addition of DMSO significantly changed the appearance of the measured spectrum. An advantageous effect was found due to the addition of DMSO which significantly changed the appearance of the measured spectrum. In FIG. 8B the background ions (labelled in FIG. 8A) are of significantly reduced intensity relative to the cocaine protonated species and the methadone protonated species.

Unexpectedly, in FIG. 8B nearly all of the background ions associated with urea and creatine are of reduced relative intensity while the drugs of abuse (methadone and cocaine) are detected at the 500 ng/mL concentration. An excellent effect was observed where the addition of DMSO significantly reduced the relative intensity of the background ions associated with urea and creatine. An advantageous effect was found where addition of DMSO reduced the relative intensity of the background ions associated with urea and creatine. This advantage extends beyond the detection of the drug compounds as it appears in FIG. 8B that detection of other sample related ions, those not originating from the background (labelled with * in FIG. 8A), are generating ion abundances above 10% of the protonated Cocaine (Co) signal now present strong ion abundance. Further, the reduction in intensity of these background ions without background spectrum subtraction reduces the need for additional spectrum processing.

Relationship Between Aliquot Volume and Area of Spot

The dependence of the area of a spot on volume was investigated by using the Mosquito to apply a specific volume of urine spiked with either one, two or three drugs of abuse on a thirteenth QuickStrip wire mesh. In order to load the same amount, 1 ng of material, onto each of the different spots on the QuickStrip 5, 4, 2.5, 1.25, and 1 ng $uL^{-1}$ samples of each drug were prepared in urine and respectively deposited as volumes of 200, 400, 500, 800 and 1000 nL. The thirteenth mesh was then analyzed and the area of each protonated species was determined for each of the different volume spots in replicate.

In urine spiked with codeine the protonated codeine signal increased from less than $10^5$ ions when 1000 nL was applied to $9\times10^5$ ions when 200 nL was applied, see FIG. 15A (where FIGS. 15A-18B depict average area which corresponds with signal intensity). In urine spiked with methadone the protonated methadone signal increased from 1.6 $10^7$ ions when 1000 nL was applied to $3.6\times10^7$ ions when 200 nL was applied, see FIG. 15B.

In urine spiked with heroin and codeine the average area of the protonated heroin ion signal increased from $4\times10^3$ $mm^2$ when 1000 nL was applied to $9\times10^3$ $mm^2$ when 200 nL was applied, see FIG. 16A. In urine spiked with heroin and codeine the average area of the protonated codeine ion signal increased from $2.5\times10^4$ $mm^2$ when 1000 nL was applied to $5.5\times10^4$ $mm^2$ when 200 nL was applied, see FIG. 16B.

In urine spiked with heroin, codeine, and methamphetamine the average area of the protonated heroin ion signal increased from $4\times10^3$ $mm^2$ when 1000 nL was applied to $1.5\times10^4$ $mm^2$ when 200 nL was applied, see FIG. 17A. In urine spiked with heroin, codeine, and methamphetamine the average area of the protonated codeine ion signal increased from $1.2\times10^4$ $mm^2$ when 1000 nL was applied to $3.5\times10^4$ $mm^2$ when 200 nL was applied, see FIG. 17B.

Unexpectedly, the absolute signal intensity for the molecule of interest was observed to increase as the volume of sample applied became smaller. An excellent effect was observed where the signal was observed to increase as the volume became smaller. An advantageous effect was found where the signal was observed to increase as the volume became smaller. In an embodiment of the invention, the average area from which the protonated analyte species is observed is between a lower limit of approximately $10^2$ $mm^2$ and an upper limit of approximately $10^5$ $mm^2$. In an embodiment of the invention, the average area from which the protonated analyte species is observed is between a lower limit of approximately $10^3$ $mm^2$ and an upper limit of approximately $10^6$ $mm^2$. In this range, approximately means plus or minus ten (10) percent. Without wishing to be bound by theory, as the volume is reduced the influence of the biological matrix in inhibiting analyte ion formation is reduced, thereby allowing the protonated analyte ion signal to be observed when desorbed from a smaller volume.

Relationship Between Sample Exposure Time and Area of Spot

The dependence of the area of the spot on sample exposure time was investigated by adjusting the speed that the sample holder moves through the ionization region under control of the linear rail as set by its controller program; faster rail speeds results in lower sample exposure times and using equal volumes of sample for presentation through the DART ionization region where faster rail speed means shorter desorption times than slower rail speeds.

Codeine and methadone were selected for this experiment as they represent drugs of abuse that are respectively difficult and easy to ionize by DART. In separate experiments using sample concentrations of 1.0 and 5.0 ng/µL 1 ng of material was deposit onto multiple positions on the QuickStrip wire mesh in either 200 nL or 1 µL sample volumes. The two solutions were used in order to maintaining the same amount of material deposited in each position. The sample laden QuickStrip wire mesh was positioned in the module attached to a motorized linear rail, which served to push the samples in sequence through the ionizing gas stream exiting the DART source. Two exposure times were examined by setting the sample introduction speed to either 1.0 mm per second or 3.0 mm per second. The average area for the protonated molecule was determined by averaging the results from multiple sample analysis. FIG. 18A shows a plot of the average area vs aliquot volume for the protonated codeine with the rail speed set to either 1 mm/second (dashed-line) or 3 mm/second (solid line). The speed of sampling is observed to be critical factor where the slower speed is observed to permit detection of more abundant signals from the same amount of sample. The effect of speed is nearly eliminated as it increases. FIG. 18B shows a plot of the average area vs aliquot volume for the protonated methadone with the rail speed set to either 1 mm/second (dashed-line) or 3 mm/second (solid line). For the methadone the speed of sampling was observed to favor the use of slower speed for detection, however the effect is not as significant as for the codeine. Once again the effect of speed on detection is nearly eliminated as it increases.

Table I shows the intensity of the methadone (m/z 310.2) ion normalized to the intensity of the methadone-d3 (m/z 313.2) ion. The measurements comprise four (4) replicate spectra taken at the five (5) concentrations.

TABLE I

| Concentration (ng/mL) | m/z 310.2 | m/z 313.2 |
|---|---|---|
| 50 | 70 ± 4 | 100 |
| 100 | 102 ± 8 | 100 |
| 250 | 183 ± 6 | 100 |
| 500 | 335 ± 18 | 100 |
| 1000 | 636 ± 19 | 100 |

Table II shows the results for twenty four (24) 1,000 nL spotted urine samples doped with 1000 ng/mL methadone and 500 ng/mL methadone-d3, showing the absolute methadone (m/z 310.2) ion peak area, the absolute methadone-d3 (m/z 313.2) ion peak area, and the ratio of the methadone ion peak area to the methadone-d3 ion peak area.

TABLE II

| Spot# | Methadone Area | Methadone-d3 Area | Ratio |
|---|---|---|---|
| 1 | 9192477 | 4726356 | 1.94 |
| 2 | 13028064 | 6749966 | 1.93 |
| 3 | 14941131 | 7774225 | 1.92 |
| 4 | 15509356 | 8041628 | 1.93 |
| 5 | 11757203 | 6139805 | 1.91 |
| 6 | 10719603 | 5645525 | 1.90 |
| 7 | 14423181 | 7510870 | 1.92 |
| 8 | 13923088 | 7310156 | 1.90 |
| 9 | 15124953 | 7831709 | 1.93 |
| 10 | 10997691 | 5706301 | 1.93 |
| 11 | 7235249 | 3758329 | 1.93 |
| 12 | 8623697 | 4513035 | 1.91 |
| 13 | 14441789 | 7552207 | 1.91 |
| 14 | 19970879 | 10523812 | 1.90 |
| 15 | 21354895 | 11123363 | 1.92 |
| 16 | 13833300 | 7208351 | 1.92 |
| 17 | 11805493 | 6105707 | 1.93 |
| 18 | 10768935 | 5668568 | 1.90 |
| 19 | 20385612 | 10633185 | 1.92 |
| 20 | 18965875 | 9801654 | 1.93 |
| 21 | 20347835 | 10523441 | 1.93 |
| 22 | 15675004 | 8142748 | 1.93 |
| 23 | 15658559 | 8088413 | 1.94 |
| 24 | 16790430 | 8661522 | 1.94 |
| Average | 14394762 | 7489203 | 1.92 |
| RSD | 27% | 27% | 1% |

Table III shows the m/z and intensity (relative intensity normalized to the m/z 121.072 protonated urea-dimer) for a positive DART API mass spectrum of unprocessed urine.

| m/z | Absolute Intensity | Relative Intensity |
|---|---|---|
| 114.066 | 2652328 | 8.3 |
| 114.091 | 1015861.1 | 3.18 |
| 121.072 | 31954404 | 100 |
| 122.075 | 726610.8 | 2.27 |
| 136.021 | 1088338.6 | 3.41 |
| 149.117 | 909876.4 | 2.85 |
| 150.149 | 1168645.9 | 3.66 |
| 152.128 | 1382675.6 | 4.33 |
| 163.133 | 2223222.3 | 6.96 |
| 166.144 | 971065.6 | 3.04 |
| 180.159 | 2207300 | 6.91 |
| 185.128 | 942133.1 | 2.95 |
| 191.164 | 779468.2 | 2.44 |
| 199.169 | 1068143.9 | 3.34 |
| 208.19 | 685751.2 | 2.15 |
| 217.18 | 1950798.6 | 6.1 |
| 234.206 | 782721.5 | 2.45 |
| 371.101 | 774788.5 | 2.42 |
| 388.128 | 1266131.6 | 3.96 |
| 462.146 | 837991.8 | 2.62 |

Table IV shows the m/z and relative intensity (normalized to the m/z 152.1279 ion) for a positive DART API mass spectrum of un-spiked saliva.

| m/z | Absolute Intensity | Relative Intensity |
|---|---|---|
| 114.0915 | 2466049.3 | 48.07 |
| 124.0969 | 1589700.6 | 30.99 |
| 135.1015 | 1686938.3 | 32.89 |
| 136.0215 | 3442486 | 67.11 |
| 152.1279 | 5129630 | 100 |
| 163.1327 | 3227664.8 | 62.92 |
| 166.1437 | 1083786.3 | 21.13 |
| 180.1595 | 3617096.5 | 70.51 |
| 191.164 | 1243755.8 | 24.25 |
| 199.169 | 1864704.6 | 36.35 |
| 208.1905 | 1297434.5 | 25.29 |
| 217.1796 | 4670281.5 | 91.05 |
| 223.0965 | 1507127 | 29.38 |
| 234.2063 | 2907347.8 | 56.68 |
| 279.1588 | 2235396.5 | 43.58 |
| 304.248 | 1070993.4 | 20.88 |
| 332.1491 | 4676338 | 91.16 |
| 360.1805 | 2817485.8 | 54.93 |
| 388.1277 | 1537772.4 | 29.98 |
| 462.1467 | 1443147.6 | 28.13 |

Embodiment 1

A sampler comprising: a mesh adapted to restrict a volume of a biological sample to a first area on the mesh; a device to receive the biological sample, where the device is adapted to deliver the volume of the biological sample to the first area; and a supply located a distance from the mesh, where the supply is adapted to direct a plurality of ionizing species formed at atmosphere at a second area on the mesh generating a plurality of sample ions formed by the plurality of ionizing species interacting with the biological sample.

Embodiment 2

The sampler of Embodiment 1, where the biological sample is one or more of adsorbed, absorbed, bound and contained on the first area on the mesh.

Embodiment 3

The sampler of Embodiment 1, further comprising means for positioning the first area on the mesh to interact with the second area.

Embodiment 4

The sampler of Embodiment 1, where the volume of the biological sample applied to the first area is between: a lower limit of approximately 25 nL; and an upper limit of approximately 250 nL.

Embodiment 5

The sampler of Embodiment 1, where the density of the molecule of interest in the biological sample applied to the first area is between: a lower limit of approximately 1 $pg/mm^2$; and an upper limit of approximately 100 $ng/mm^2$.

Embodiment 6

The sampler of Embodiment 1, further comprising a cap, where when the distance is between: a lower limit of approximately 1 mm; and an upper limit of approximately 2 mm, then the second area is between: a lower limit of approximately 0.5 $mm^2$; and an upper limit of approximately 2 $mm^2$.

Embodiment 7

The sampler of Embodiment 6, further comprising a spectrometer and a gas ion separator, where the plurality of sample ions are analyzed with the spectrometer, where the gas ion separator is introduced after the plurality of ionizing species interact with the biological sample and before the plurality of sample ions enter the spectrometer.

Embodiment 8

The sampler of Embodiment 1, where the mesh is a grid with filaments spaced between: a lower limit of approximately 120/inch; and an upper limit of approximately 60/inch.

Embodiment 9

An ionizer for atmospheric ionization comprising: a surface adapted to restrict a volume of a sample present in a biological matrix to a first area on the surface; a robot programmed to receive a sample, where the robot is further programmed to deliver the volume of the sample to the first area, where a sample density on the first area is less than approximately 1 $ng/mm^2$; and a supply located a first distance from the surface, the supply adapted to direct an ionizing species formed from an atmospheric ionizing source at a second area on the surface generating a plurality of sample ions formed by the ionizing species interacting with the sample, where the ionizing species are formed from a gas.

Embodiment 10

The ionizer of Embodiment 9, where the surface is a mesh with filaments spaced between: a lower limit of approximately 120/inch; and an upper limit of approximately 60/inch.

Embodiment 11

The ionizer of Embodiment 9, further comprising means for positioning the second area such that the ionizing species interact with the first area.

Embodiment 12

The ionizer of Embodiment 9, further comprising analyzing the plurality of sample ions with a spectrometer and a gas ion separator, where the gas ion separator is introduced after the ionizing species interact with the sample and before the plurality of sample ions enter the spectrometer.

Embodiment 13

The ionizer of Embodiment 9, further comprising a means for moving the surface relative to the ionizing species to adjust the second area.

Embodiment 14

The ionizer of Embodiment 9, where the surface supports depositing multiple samples, where the multiple samples are separated by a second distance, where the diameter of the second area is less than the second distance such that the ionizing species do not simultaneously desorb sample ions from an adjacent sample.

Embodiment 15

The ionizer of Embodiment 14, where the surface is mounted on a movable stage with a stage speed, where the stage speed is controlled to move the surface through the ionizing species at a speed such that rate of change of the diameter of the second area with time is less than the rate of change of the second distance with time such that the ionizing species do not simultaneously desorb sample material from an adjacent sample.

Embodiment 16

The ionizer of Embodiment 15, where the stage speed is decreased to reduce matrix effects.

Embodiment 17

A method of ionizing a biological sample comprising: receiving a biological sample; applying the biological sample to a mesh having a first area, where a volume of the biological sample is between: a lower limit of approximately 25 nL; and an upper limit of approximately 100 nL; and passing the biological sample on the mesh in front of an atmospheric pressure ionization source positioned a distance between: a lower limit of approximately 1 mm; and an upper limit of approximately 2 mm; to generate ionizing species which impact a second area between: a lower limit of approximately 0.5 $mm^2$; and an upper limit of approximately 2 $mm^2$, to generate ions of the biological sample.

Embodiment 18

The method of Embodiment 17, further comprising means for positioning one or both the first area to interact with the second area and the second area to interact with the first area.

Embodiment 19

The method of Embodiment 17, where the mesh is cut or etched to restrict the biological sample to the first area.

Embodiment 20

The method of Embodiment 17, where the mesh is mounted on a moving stage and passed in front of the atmospheric pressure ionization source at a regulated speed.

Embodiment 21

The method of Embodiment 20, where the regulated speed is decreased to reduce matrix effects.

Embodiment 22

A method of ionizing a sample comprising: receiving a sample; diluting the sample with an ion intensifier; applying the diluted sample to a first area on a mesh; and passing the first area in front of an atmospheric pressure ionization source positioned a distance between: a lower limit of approximately 1 mm; and an upper limit of approximately 2 mm; to generate ionizing species which impact a second area on the mesh between: a lower limit of approximately 0.5 mm$^2$; and an upper limit of approximately 2 mm$^2$, to generate ions of the sample.

Embodiment 23

The method of Embodiment 22, where the ion intensifier is DMSO.

Embodiment 24

A method of ionizing a biological sample comprising: receiving a biological sample; diluting the biological sample with DMSO; applying to a first area of a mesh the diluted biological sample between: a lower limit of approximately 25 nL; and an upper limit of approximately 250 nL; and passing the first area in front of an atmospheric pressure ionization source to generate ionizing species, where the ionizing species interact with a second area on the mesh to generate ions of the biological sample.

Embodiment 25

The method of Embodiment 24, further comprising means for positioning one or both the first area to interact with the second area and the second area to interact with the first area.

Embodiment 26

A method of ionizing a biological sample comprising: receiving a biological sample; diluting the biological sample with DMSO; applying to a first area of a mesh the diluted biological sample; and passing the first area in front of an atmospheric pressure ionization source to generate ionizing species, where the ionizing species interact with a second area on the mesh to generate ions of the biological sample.

Embodiment 27

A method of ionizing a sample comprising: receiving a sample; diluting the sample with an ion intensifier; applying the diluted sample to a first area on a mesh; and passing the first area in front of an atmospheric pressure ionization source adapted to generate ionizing species comprising a cap to restrict the spread of the ionizing species, where the cap is positioned a distance from the mesh; generating ionizing species which impact a second area on the mesh, where the second area interacts with the first area to generate ions of the sample.

Embodiment 28

The method of Embodiment 27, where the sample is one or more of adsorbed, absorbed, bound and contained on the first area on the mesh.

Embodiment 29

The method of Embodiment 27, further comprising means for positioning the first area on the mesh to interact with the second area.

Embodiment 30

The method of Embodiment 27, where the volume of the sample applied to the first area is between: a lower limit of approximately 25 nL; and an upper limit of approximately 250 nL.

Embodiment 31

The method of Embodiment 27, where the density of the sample applied to the first area is between: a lower limit of approximately 1 pg/mm$^2$; and an upper limit of approximately 1 ng/mm$^2$.

Embodiment 32

The method of Embodiment 27, where the distance is between: a lower limit of approximately 1 mm; and an upper limit of approximately 2 mm.

Embodiment 33

The method of Embodiment 32, where the second area is between: a lower limit of approximately 0.5 mm$^2$; and an upper limit of approximately 2 mm$^2$.

Embodiment 34

The method of Embodiment 27, further comprising a spectrometer and a gas ion separator, where the ions are analyzed with the spectrometer, where the gas ion separator is positioned after the ionizing species interact with the sample and before the ions enter the spectrometer.

Embodiment 35

The method of Embodiment 27, where the mesh is a grid with filaments spaced between: a lower limit of approximately 120/inch; and an upper limit of approximately 60/inch.

Embodiment 36

The method of Embodiment 27, where the ion intensifier is DMSO.

Embodiment 37

A sampler comprising: a mesh adapted to restrict a volume of a biological sample to a first area on the mesh; a device to receive the biological sample, where the device is adapted to deliver the volume of the biological sample to the first area; a supply adapted to generate a plurality of ionizing species formed at atmosphere; and a cap, where the cap is adapted to restrict the spread of ionizing species and is located a distance from the mesh, where the plurality of ionizing species impact a second area on the mesh, where a plurality of sample ions are formed by the plurality of ionizing species when the first area intersects with the second area.

Embodiment 38

The sampler of Embodiment 37, where the biological sample is one or more of adsorbed, absorbed, bound and contained on the first area on the mesh.

Embodiment 39

The sampler of Embodiment 37, further comprising means for positioning the first area on the mesh to interact with the second area.

Embodiment 40

The sampler of Embodiment 37, where the volume of the biological sample applied to the first area is between: a lower limit of approximately 25 nL; and an upper limit of approximately 250 nL.

Embodiment 41

The sampler of Embodiment 37, where the density of the biological sample applied to the first area is between: a lower limit of approximately 1 $pg/mm^2$; and an upper limit of approximately 1 $ng/mm^2$.

Embodiment 42

The sampler of Embodiment 37, where the distance is between: a lower limit of approximately 1 mm; and an upper limit of approximately 2 mm.

Embodiment 43

The sampler of Embodiment 42, where the second area is between: a lower limit of approximately 0.5 $mm^2$; and an upper limit of approximately 2 $mm^2$.

Embodiment 44

The sampler of Embodiment 37, further comprising a spectrometer and a gas ion separator, where the plurality of sample ions are analyzed with the spectrometer, where the gas ion separator is positioned between the biological sample and the spectrometer.

Embodiment 45

The sampler of Embodiment 37, where the mesh is a grid with filaments spaced between: a lower limit of approximately 120/inch; and an upper limit of approximately 60/inch.

Embodiment 46

An ionizer for atmospheric ionization comprising: a surface adapted to restrict a volume of a sample present in a biological matrix to a first area on the surface; a robot programmed to receive a sample, where the robot is further programmed to deliver the volume of the sample to the first area, where a sample density on the first area is less than approximately 1 $ng/mm^2$; and a supply located a first distance from the surface, the supply adapted to direct an ionizing species formed from an atmospheric ionizing source at a second area on the surface generating a plurality of sample ions formed by the ionizing species interacting with the sample, where the ionizing species are formed from a gas.

Embodiment 47

The sampler of Embodiment 46, further comprising means for positioning the second area such that the ionizing species interact with the first area.

Embodiment 48

The sampler of Embodiment 46, further comprising a means for moving the surface relative to the ionizing species to adjust the second area.

Embodiment 49

The sampler of Embodiment 46, where the surface supports depositing a plurality of samples, where the plurality of samples are separated by a second distance, where a diameter of the second area is less than the second distance.

Embodiment 50

The sampler of Embodiment 49, where the surface is mounted on a movable stage with a stage speed, where the stage speed is controlled to move the surface through the ionizing species at a speed such that rate of change of the diameter with time is less than the rate of change of the second distance with time.

Embodiment 51

The sampler of Embodiment 50, where the stage speed is decreased to reduce matrix effects.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

What is claimed is:
1. A method of ionizing a sample comprising:
   receiving a sample;
   diluting the sample with an ion intensifier;
   applying the diluted sample to a first area on a mesh; and
   passing the first area in front of an atmospheric pressure ionization source adapted to generate ionizing species comprising a cap to restrict the spread of the ionizing species, where the cap is positioned a distance from the mesh;

generating ionizing species which impact a second area on the mesh, where the second area interacts with the first area to generate ions of the sample.

2. The method of claim 1, where the ion intensifier is dimethyl sulfoxide (DMSO).

3. The method of claim 1, further comprising means for positioning the first area on the mesh to interact with the second area.

4. The method of claim 1, where the volume of the sample applied to the first area is between:
a lower limit of approximately 25 nL; and
an upper limit of approximately 250 nL.

5. The method of claim 1, further comprising a spectrometer and a gas ion separator, where the ions are analyzed with the spectrometer, where the gas ion separator is positioned after the ionizing species interact with the sample and before the ions enter the spectrometer.

6. The method of claim 1, where the distance is between:
a lower limit of approximately 1 mm; and
an upper limit of approximately 2 mm.

7. The method of claim 6, where the second area is between:
a lower limit of approximately 0.5 $mm^2$; and
an upper limit of approximately 2 $mm^2$.

8. A sampler comprising:
a mesh adapted to restrict a volume of a biological sample to a first area on the mesh;
a device to receive the biological sample, where the device is adapted to deliver the volume of the biological sample to the first area;
a supply adapted to generate a plurality of ionizing species formed at atmosphere; and
a cap, where the cap is adapted to restrict the spread of ionizing species and is located a distance from the mesh, where the plurality of ionizing species impact a second area on the mesh, where a plurality of sample ions are formed by the plurality of ionizing species when the first area intersects with the second area.

9. The sampler of claim 8, further comprising means for positioning the first area on the mesh to interact with the second area.

10. The sampler of claim 8, where the volume of the biological sample applied to the first area is between:
a lower limit of approximately 25 nL; and
an upper limit of approximately 250 nL.

11. The sampler of claim 8, where the distance is between:
a lower limit of approximately 1 mm; and
an upper limit of approximately 2 mm.

12. The sampler of claim 11, where the second area is between:
a lower limit of approximately 0.5 $mm^2$; and
an upper limit of approximately 2 $mm^2$.

13. The sampler of claim 8, further comprising a spectrometer and a gas ion separator, where the plurality of sample ions are analyzed with the spectrometer, where the gas ion separator is positioned between the biological sample and the spectrometer.

14. The sampler of claim 8, where the mesh is a grid with filaments spaced between:
a lower limit of approximately 120/inch; and
an upper limit of approximately 60/inch.

15. An ionizer for atmospheric ionization comprising:
a surface adapted to restrict a volume of a sample present in a biological matrix to a first area on the surface;
a robot programmed to receive a sample, where the robot is further programmed to deliver the volume of the sample to the first area, where a sample density of a molecule of interest on the first area is less than approximately 100 ng/$mm^2$; and
a supply located a first distance from the surface, the supply adapted to direct an ionizing species formed from an atmospheric ionizing source at a second area on the surface generating a plurality of sample ions formed by the ionizing species interacting with the sample, where the ionizing species are formed from a gas.

16. The ionizer of claim 15, further comprising means for positioning the second area such that the ionizing species interact with the first area.

17. The ionizer of claim 15, further comprising a means for moving the surface relative to the ionizing species to adjust the second area.

18. The ionizer of claim 15, where the surface supports depositing a plurality of samples, where the plurality of samples are separated by a second distance, where a diameter of the second area is less than the second distance.

19. The ionizer of claim 18, where the surface is mounted on a movable stage with a stage speed, where the stage speed is controlled to move the surface through the ionizing species at a speed such that rate of change of the diameter with time is less than the rate of change of the second distance with time.

20. The ionizer of claim 19, where the stage speed is decreased to reduce matrix effects.

\* \* \* \* \*